United States Patent
Dai et al.

(10) Patent No.: US 11,014,936 B2
(45) Date of Patent: May 25, 2021

(54) SELECTIVE ESTROGEN RECEPTOR DEGRADERS AND USES THEREOF

(71) Applicant: INVENTISBIO INC., Grand Cayman (KY)

(72) Inventors: Xing Dai, Short Hills, NJ (US); Yaolin Wang, Short Hills, NJ (US)

(73) Assignee: INVENTISBIO LLC, Florham Park, NJ (US)

( * ) Notice: Subject to any disclaimer, the term of this patent is extended or adjusted under 35 U.S.C. 154(b) by 0 days.

(21) Appl. No.: 16/655,689

(22) Filed: Oct. 17, 2019

(65) Prior Publication Data

US 2020/0048250 A1    Feb. 13, 2020

Related U.S. Application Data

(63) Continuation of application No. 16/073,673, filed as application No. PCT/US2017/016452 on Feb. 3, 2017, now Pat. No. 10,647,724.

(60) Provisional application No. 62/291,921, filed on Feb. 5, 2016.

(51) Int. Cl.
| | |
|---|---|
| C07D 471/04 | (2006.01) |
| A61K 31/437 | (2006.01) |
| C07D 495/04 | (2006.01) |
| A61P 35/00 | (2006.01) |
| A61P 5/32 | (2006.01) |
| C07D 471/14 | (2006.01) |
| C07D 491/048 | (2006.01) |

(52) U.S. Cl.
CPC ............ *C07D 495/04* (2013.01); *A61P 5/32* (2018.01); *A61P 35/00* (2018.01); *C07D 471/04* (2013.01); *C07D 471/14* (2013.01); *C07D 491/048* (2013.01)

(58) Field of Classification Search
CPC .......... C07D 471/04; C07D 471/14; C07D 491/048; A61K 31/437; A61K 31/4355; A61P 35/00
USPC ............ 546/85, 82, 89; 514/292, 291, 293
See application file for complete search history.

(56) References Cited

U.S. PATENT DOCUMENTS

| | | | |
|---|---|---|---|
| 9,980,947 B2 * | 5/2018 | Labadie | A61K 45/06 |
| 2003/0225132 A1 | 12/2003 | DiNinno et al. | |
| 2014/0107095 A1 | 4/2014 | Kahraman et al. | |
| 2014/0357661 A1 | 12/2014 | Bradbury et al. | |
| 2015/0005286 A1 | 1/2015 | Smith et al. | |
| 2015/0258099 A1 | 9/2015 | Hager et al. | |
| 2017/0362228 A1 | 12/2017 | Labadie et al. | |
| 2018/0002344 A1 | 1/2018 | Labadie et al. | |
| 2018/0021316 A1 | 1/2018 | Scott et al. | |

FOREIGN PATENT DOCUMENTS

| | | |
|---|---|---|
| CN | 105229004 A | 1/2016 |
| EP | 3312184 A1 | 4/2018 |
| EP | 3378861 A1 | 9/2018 |
| WO | WO 2003/059346 A1 | 7/2003 |
| WO | WO 2004/091488 A2 | 10/2004 |
| WO | WO 2009/064251 A1 | 5/2009 |
| WO | WO-2010138706 A1 | 12/2010 |
| WO | WO 2014/151899 A1 | 9/2014 |
| WO | WO 2014/205136 A1 | 12/2014 |
| WO | WO-2014191726 A1 | 12/2014 |

(Continued)

OTHER PUBLICATIONS

Extended European Search Report for European Application No. 17748247.8, Munich, Germany, dated Jul. 25, 2019, 11 pages.

(Continued)

*Primary Examiner* — Charanjit Aulakh
(74) *Attorney, Agent, or Firm* — Nixon & Vanderhye P.C.

(57) ABSTRACT

The present disclosure provides compounds of Formula (I) and Formula (II). The compounds described herein may be useful in treating proliferative diseases (e.g., cancer). Also provided in the present disclosure are pharmaceutical compositions, kits, methods, and uses including or using a compound described herein.

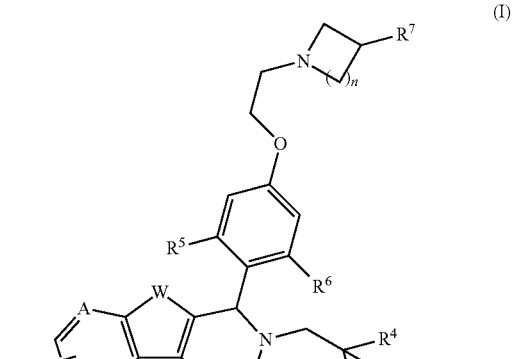

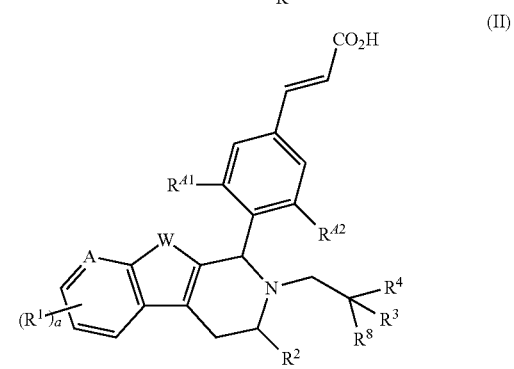

18 Claims, 3 Drawing Sheets

(56) References Cited

FOREIGN PATENT DOCUMENTS

| WO | WO-2015190568 A1 | 12/2015 |
| WO | WO-2016097072 A1 | 6/2016 |
| WO | WO-2016202161 A1 | 12/2016 |
| WO | WO-2017059139 A1 | 4/2017 |
| WO | WO-2017080338 A1 | 5/2017 |
| WO | WO-2017172957 A1 | 10/2017 |
| WO | WO-2017216279 A1 | 12/2017 |
| WO | WO-2017216280 A1 | 12/2017 |
| WO | WO-2018019793 A1 | 2/2018 |
| WO | WO-2018077260 A1 | 5/2018 |
| WO | WO-2018130124 A1 | 7/2018 |
| WO | WO-2018138303 A1 | 8/2018 |

OTHER PUBLICATIONS

International Preliminary Report on Patentability for International Application No. PCT/US2017/016452, Commissioner for Patents, Virginia dated Aug. 16, 2018, 6 pages.

McDonnell, D.P., et al., "Oral Selective Estrogen Receptor Downregulators (SERDs), a Breakthrough Endocrine Therapy for Breast Cancer," Journal of Medicinal Chemistry, 58(12):4883-4887, American Chemical Society, United States (Jun. 2015).

Scott, J.S., et al., "Building Bridges in a Series of Estrogen Receptor Degraders: An Application of Metathesis in Medicinal Chemistry," ACS Medicinal Chemistry Letters, 10(10):1492-1497, American Chemical Society, United States (Sep. 2019).

Written Opinion for International Application No. PCT/US2017/016452, Commissioner for Patents, Virginia dated Apr. 25, 2017, 4 pages.

De Savi et al., "Optimization of a Novel Binding Motif to (E)-3-(3,5-Difluoro-4-((1R,3R)-2-(2-fluoro-2-methylpropyl)-3-methyl-2,3,4,9-tetrahydro-1H-pyrido[3,4-b]indol-1-yl)phenyl)acrylic Acid (AZD9496), a Potent and Orally Bioavailable Selective Estrogen Receptor Downregulator and Antagonist," Journal of Medicinal Chemistry 58:8128-8140 (2015).

International Search Report of PCT/US2017/016452 dated Apr. 25, 2017, WIPO.

* cited by examiner

SELECTIVE ESTROGEN RECEPTOR DEGRADERS AND USES THEREOF

RELATED APPLICATION

This application is a continuation of U.S. application Ser. No. 16/073,673, which is the U.S. national phase of International Application No. PCT/US2017/016452, filed Feb. 3, 2017, which claims priority under 35 U.S.C. § 119(e) to U.S. Provisional Application, U.S. Ser. No. 62/291,921, filed Feb. 5, 2016, the content of each of which is incorporated herein by reference in its entirety.

BACKGROUND OF THE INVENTION

Breast cancer is the most common cause of death for women worldwide. Majority of breast cancer (~80%) depends on the signaling pathway mediated by the estrogen receptor (ER) for growth. Therefore, targeting the ER or its signaling pathway remains to be the key in development of drug for treating breast cancer. Estrogen receptors (including ERα and ERβ) are a group of receptors that are activated by the hormone estrogen (17β-estradiol). Current therapy for ER positive (ER+) breast cancer including agents that inhibit the ER activity through direct binding to the ligand binding domain of the receptor (e.g., tamoxifen); blocking the synthesis of estrogen (e.g., aromatase inhibitor such as anastrozole and letrozole); or inducing the degradation of ER (e.g., fulvestrant).

Drugs that inhibit estrogen receptor or block the production of estrogens are commonly used in the treatment and management of ER+ breast cancer and other hormone-dependent cancers. However, drug resistance remains a challenge in breast cancer treatment, particularly treatment of cancers in advanced stages. Selective Estrogen Receptor Degraders (SERD) are a class of small molecules that bind to the estrogen receptor, resulting in degradation of the estrogen receptor. Studies showed that SERDs are specifically useful in treating cancers that are resistant to other drugs such as tamoxifen and/or aromatase inhibitors (McDonnell et al., J. Med. Chem. 2015, 58, 4883-4887). Fulvestrant is a SERD that has been approved for treatment of ER+ breast cancer. However, fulvestrant is a metabolized quickly and administered by intramuscular injection monthly, which limit the effective degradation of ER (~50% ER degradation in clinical samples) compared to the complete ER degradation seen in vitro study. Recently, ER mutations have been detected in biopsy samples from breast cancer patients who have developed resistance to treatment of aromatase inhibitor. These mutations are mostly frequently occurring at amino acid 537 and 538 within the ligand binding domain of ER. Interestingly, these mutated ER still bind to and inhibited by both tamoxifen and fulvestrant to some degree (Li et al., 2013 Cell Reports 4, 1116-1130; Toy et al., 2013, 45, 1439-1445; Robinson et al., Nature Genetics 2013, 45, 1446-1451). It has also been shown that fulvestrant can still effectively degrade the mutated Try537Ser ER protein. This presents an opportunity that compound targeting the ER degradation similar to fulvestrant could effectively degraded the mutated ER protein as well and useful in treating breast cancer patients that developed resistance to aromatase inhibitor. Therefore, it is of great importance to develop new and non-steroidal SERDs for use in breast cancer and other ER related disease therapy.

SUMMARY OF THE INVENTION

The present disclosure provides compounds, such as compounds of Formula (I) and Formula (II), that are Selective Estrogen Receptor Degraders (SERD). The compounds described herein may be useful in treating breast cancer, particularly ER+ breast cancer, and diseases associated with ER. Also provided are pharmaceutical compositions, kits, methods, and uses of any of the compounds described herein.

In one aspect, the present disclosure provides compounds of Formula (I):

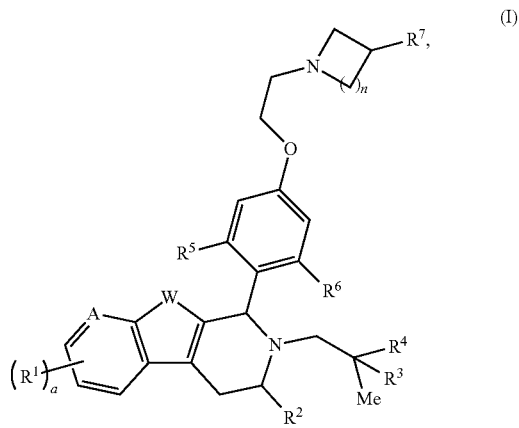

or pharmaceutically acceptable salts, wherein A is —$CR^4$= or —N=, as valency permits; W is —NH—, —O—, or —S—; a is 1, 2, or 3; and n is 1, 2, 3, or 4. In addition, each instance of $R^1$ is independently hydrogen, halogen, substituted or unsubstituted alkyl, —$OR^A$, or —CN;

$R^2$ is hydrogen, substituted or unsubstituted alkyl, substituted or unsubstituted carbocyclyl;

$R^3$ is hydrogen, halogen, substituted or unsubstituted alkyl, substituted or unsubstituted carbocyclyl, substituted or unsubstituted heterocyclyl, substituted or unsubstituted aryl, or substituted or unsubstituted heteroaryl, —$OR^A$, or —$N(R^B)_2$;

$R^4$ is hydrogen, halogen, substituted or unsubstituted alkyl, substituted or unsubstituted carbocyclyl, substituted or unsubstituted heterocyclyl, substituted or unsubstituted aryl, or substituted or unsubstituted heteroaryl, —$OR^A$ or —$N(R^B)_2$;

$R^5$ is hydrogen, halogen, substituted or unsubstituted alkyl;

$R^6$ is hydrogen, halogen, substituted or unsubstituted alkyl;

$R^7$ is hydrogen, halogen, substituted or unsubstituted alkyl, —$OR^A$ or —$N(R^B)_2$;

$R^A$ is hydrogen or substituted or unsubstituted alkyl, or oxygen protecting group; and $R^B$ is hydrogen or substituted or unsubstituted alkyl, nitrogen protecting group, or optionally two $R^B$ are taken together with the intervening atoms to form substituted or unsubstituted heterocyclyl or substituted or unsubstituted heteroaryl.

In certain embodiments, a compound of Formula (I) is of the formula:
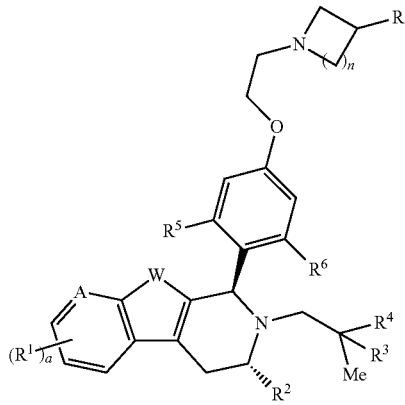
wherein $R^1$, $R^2$, $R^3$, $R^4$, $R^5$, $R^6$, $R^7$, A, W, a, and n are as described herein.
Exemplary compounds of Formula (I) include, but are not limited to:
1
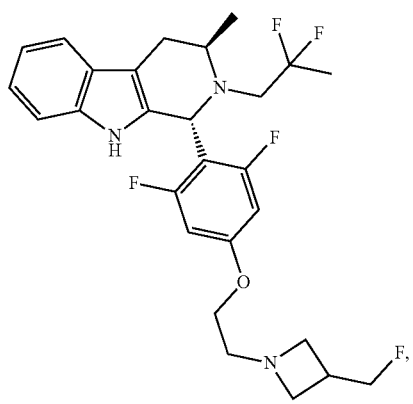
2
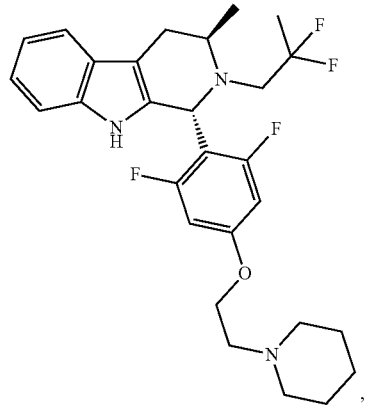
3
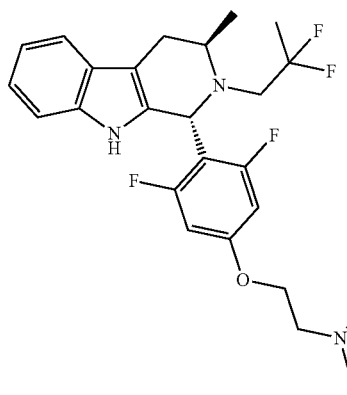
4
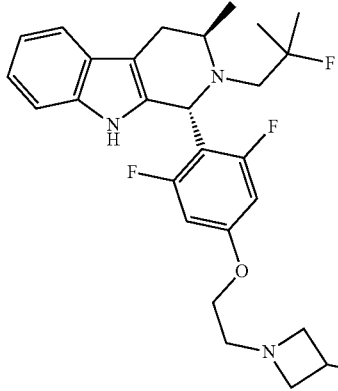
5
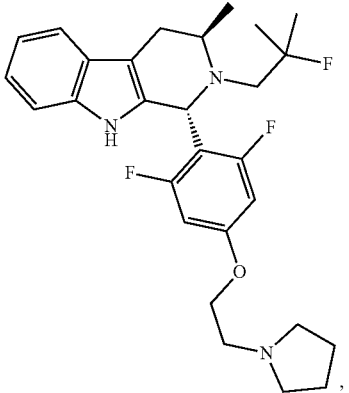
6

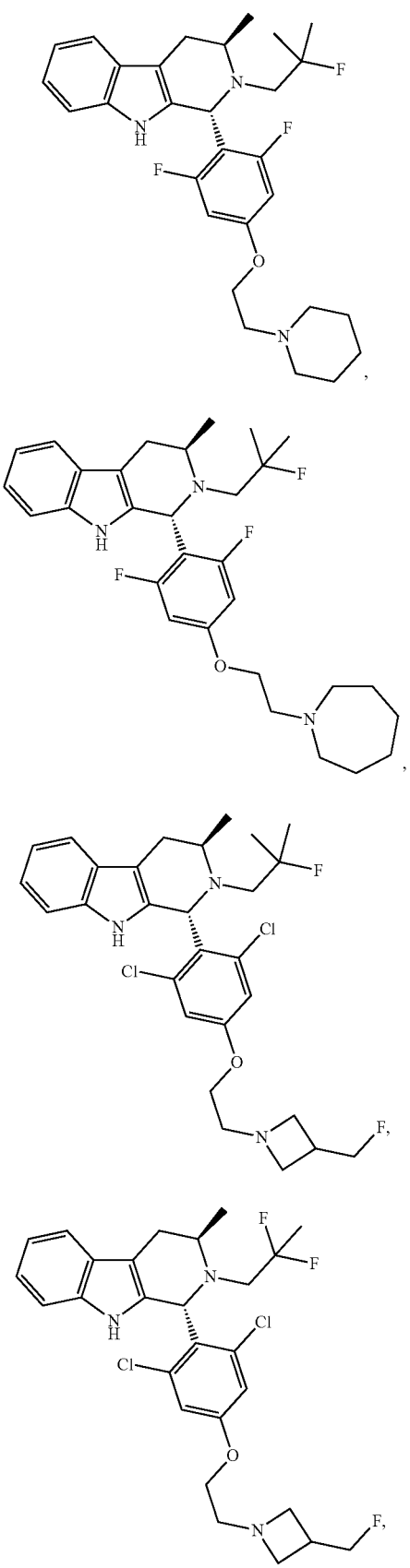
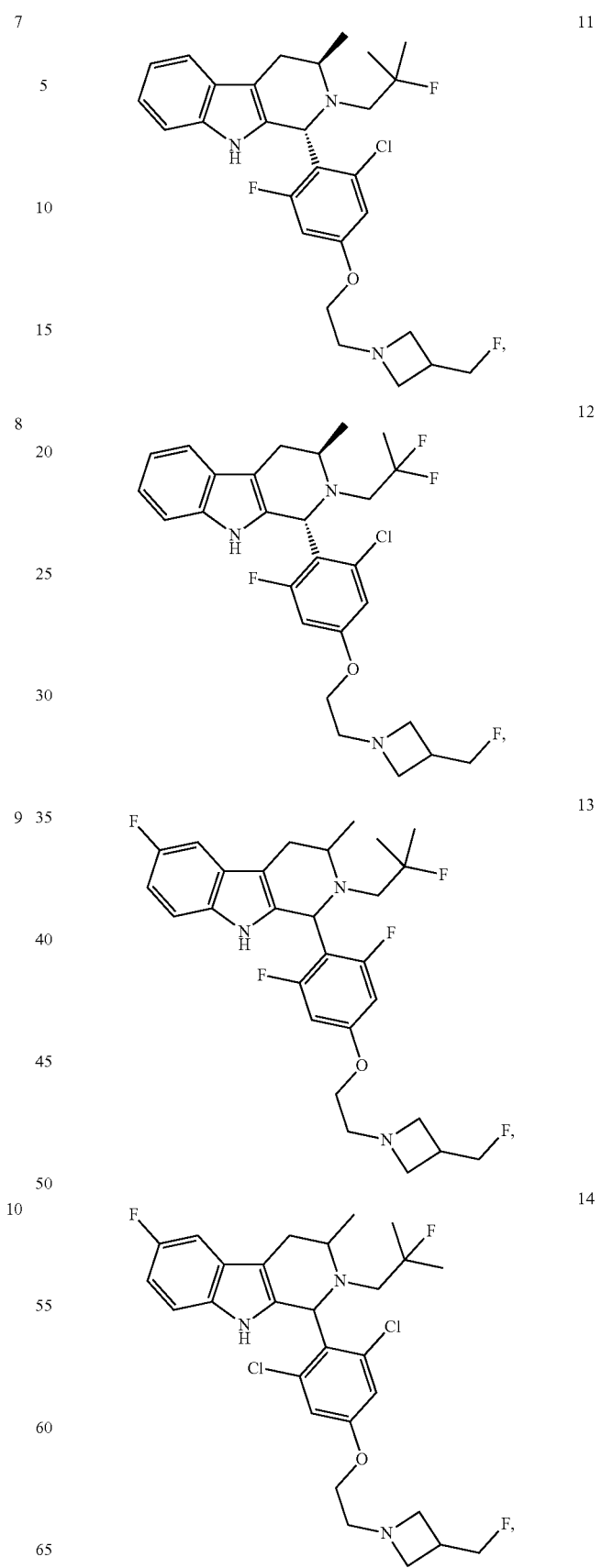

15 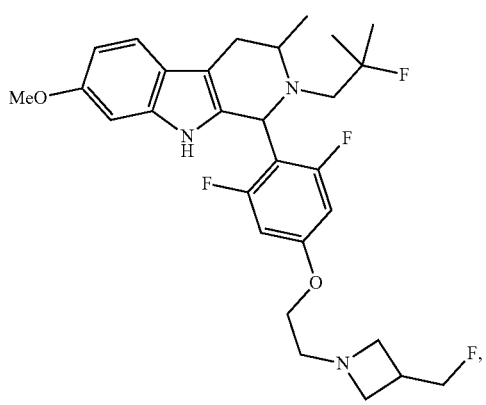

16 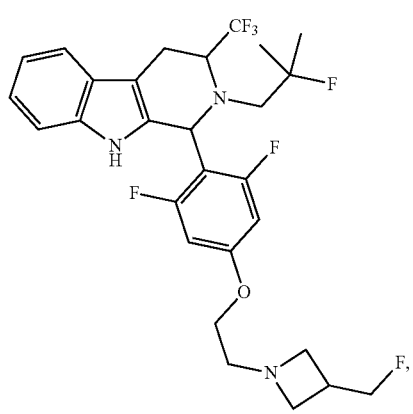

17 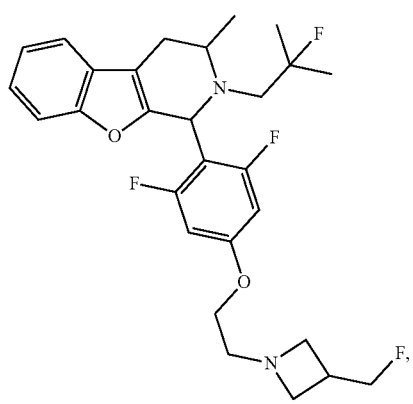

18 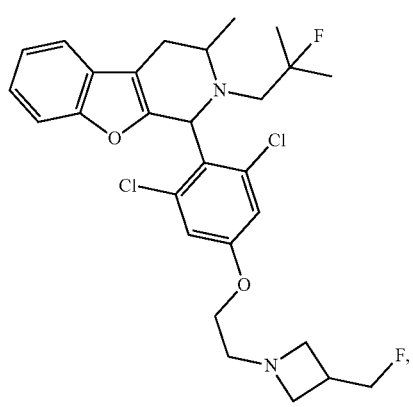

19 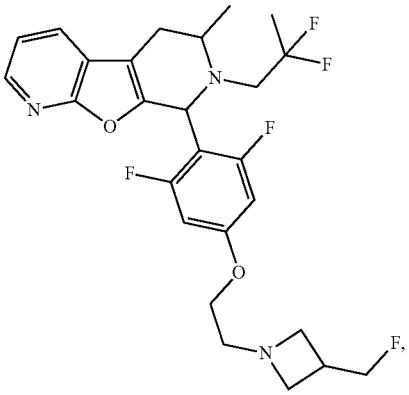

or pharmaceutically acceptable salts.

In another aspect, the present disclosure provides compounds of Formula (II):

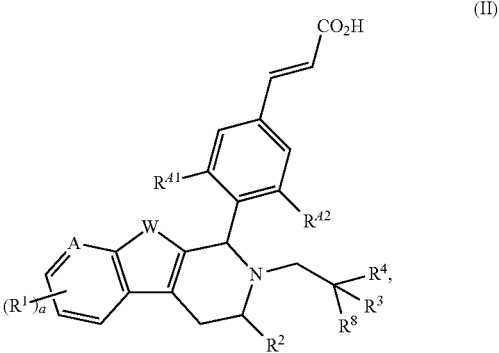

(II)

or pharmaceutically acceptable salts, wherein A is —CR$^4$= or —N=, as valency permits; W is —NH—, —O—, or —S—; and a is 1, 2, or 3. In addition, each instance of R$^1$ is independently hydrogen, halogen, substituted or unsubstituted alkyl, —OR$^A$, or —CN;

R$^2$ is hydrogen, substituted or unsubstituted alkyl, substituted or unsubstituted carbocyclyl;

R$^3$ is hydrogen, halogen, substituted or unsubstituted alkyl, substituted or unsubstituted carbocyclyl, substituted or unsubstituted heterocyclyl, substituted or unsubstituted aryl, or substituted or unsubstituted heteroaryl, —OR$^A$ or —N(R$^B$)$_2$;

R$^4$ is hydrogen, halogen, substituted or unsubstituted alkyl, substituted or unsubstituted carbocyclyl, substituted or unsubstituted heterocyclyl, substituted or unsubstituted aryl, or substituted or unsubstituted heteroaryl, —OR$^A$ or —N(R$^B$)$_2$, Or R$^3$ and R$^4$ are taken together with the intervening atoms to form substituted or unsubstituted carbocyclyl or substituted or unsubstituted heterocyclyl;

R$^8$ is hydrogen, halogen, or substituted or unsubstituted methyl (e.g., methyl);

R$^{A1}$ is substituted or unsubstituted alkyl, chlorine, or fluorine; and

R$^{A2}$ is substituted or unsubstituted alkyl, chlorine, or fluorine, wherein: (i) either R$^{A1}$ or R$^{A2}$ is chlorine; or (ii) one of R$^{A1}$ and R$^{A2}$ is fluorine, and the other one of R$^{A1}$ and R$^{A2}$ is selected from the group consisting of substituted or unsubstituted alkyl, chlorine, and fluorine $R^A$ is hydrogen or substituted or unsubstituted alkyl, or oxygen protecting group; and $R^B$ is hydrogen or substituted or unsubstituted alkyl, nitrogen protecting group, or optionally two $R^B$ are taken together with the intervening atoms to form substituted or unsubstituted heterocyclyl or substituted or unsubstituted heteroaryl.

In certain embodiments, a compound of Formula (II) is of the formula:

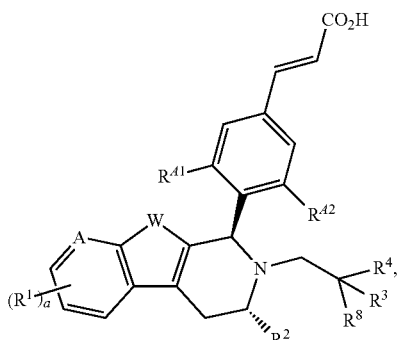

or a pharmaceutically acceptable salt, wherein $R^1$, $R^2$, $R^3$, $R^4$, $R^8$, $R^{A1}$, $R^{A2}$, A, W, and a are as described herein.

In some embodiments, at least one of $R^{A1}$ and $R^{A2}$ of Formula (II) can be chlorine. In some embodiments, both $R^{A1}$ and $R^{A2}$ of Formula (II) can be chlorine. Such exemplary compounds of Formula (II) include, but are not limited to:

20

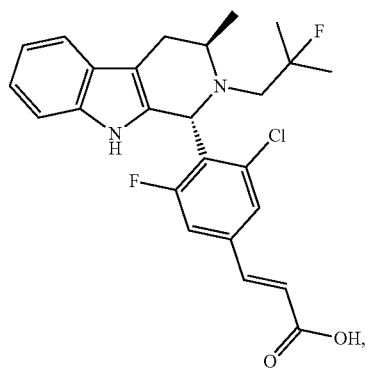

21

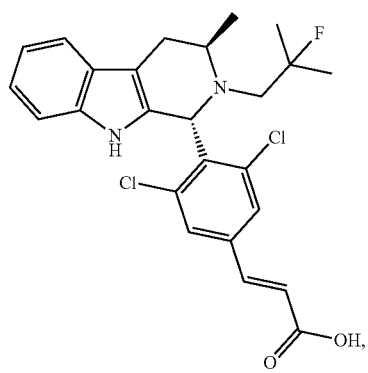

25

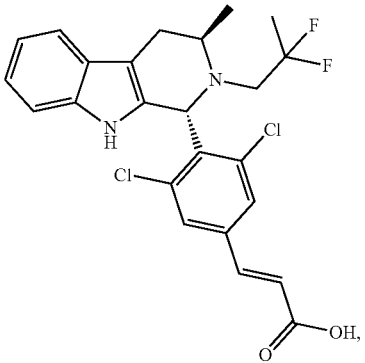

26

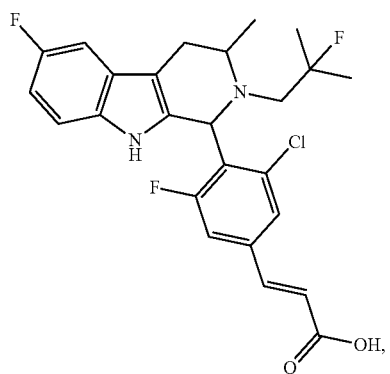

27

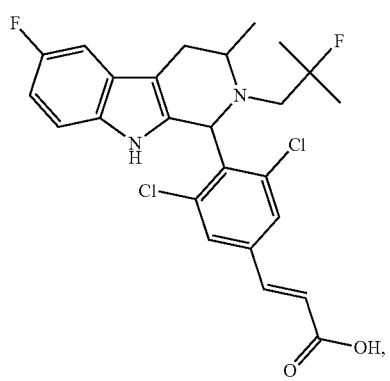

28

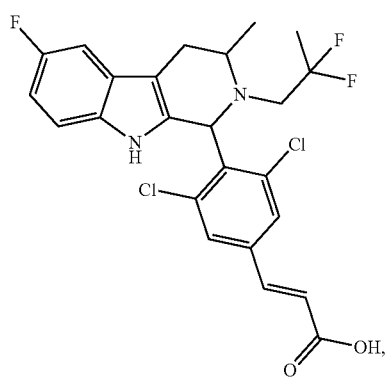

-continued

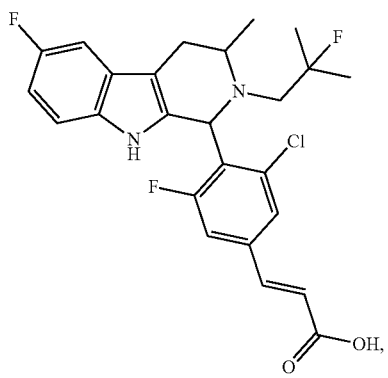
38

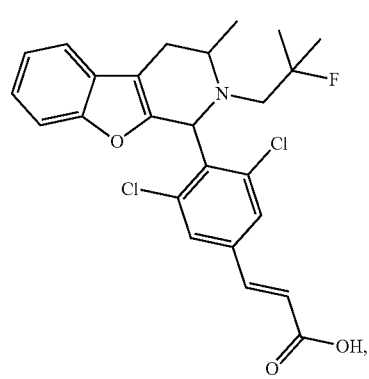

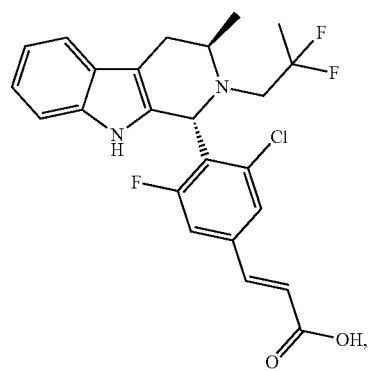
49 and pharmaceutically acceptable salts thereof.

In some embodiments, $R^{A1}$ of Formula (II) can be fluorine and $R^{A2}$ can be methyl, for example, compound 41 shown below:

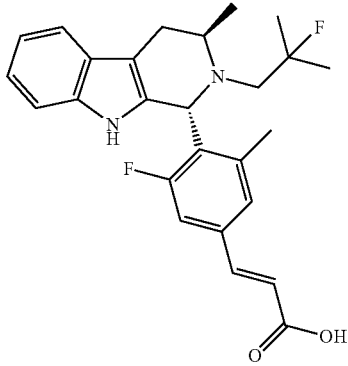
41

In some embodiments, when both $R^{A1}$ and $R^{A2}$ of Formula (II) are fluorine, the compound further satisfies at least one of the following conditions:
W is O or S;
at least one of $R^1$ is not hydrogen;
$R^2$ is not hydrogen or methyl;
A is —N or —$CR^A$, wherein $R^A$ is substituted or unsubstituted alkyl, or oxygen protecting group;
$R^3$ and $R^4$ are taken together with the intervening atoms to form substituted or unsubstituted carbocyclyl or substituted or unsubstituted heterocyclyl; or
at least two of $R^3$, $R^4$, and $R^8$ are each independently halogen.

Examples of such compounds of Formula (II) include, but are not limited to:

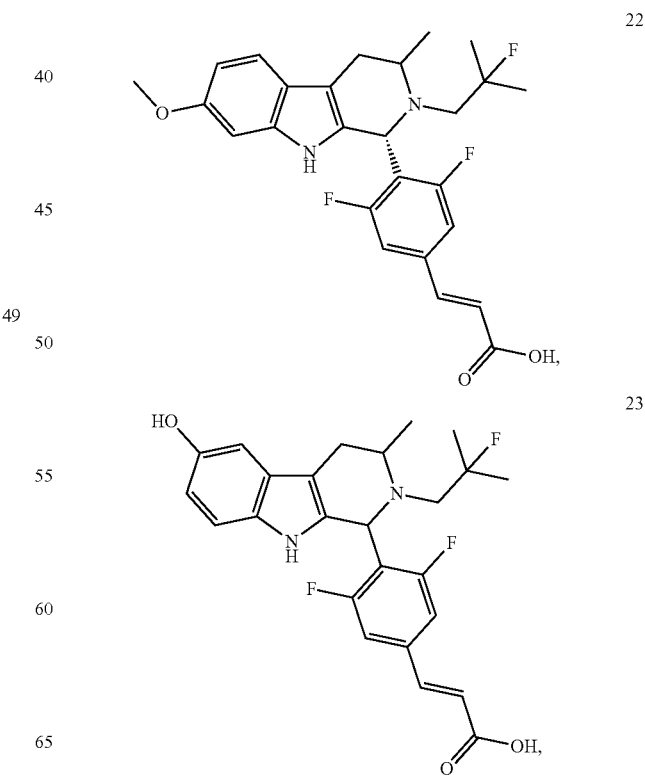

24
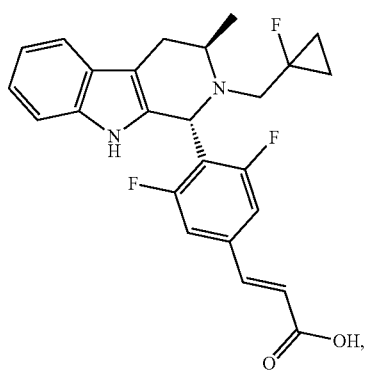
29
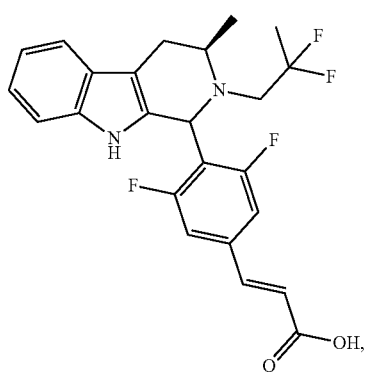
30
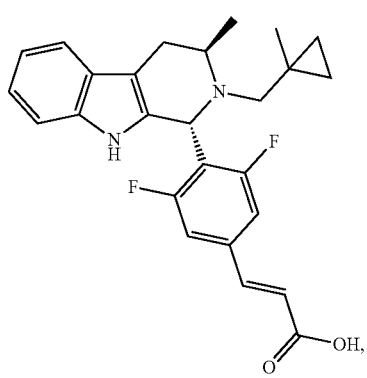
31
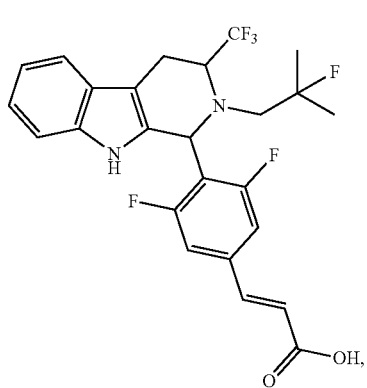
32
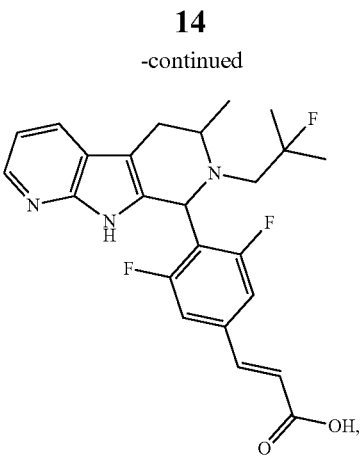
33
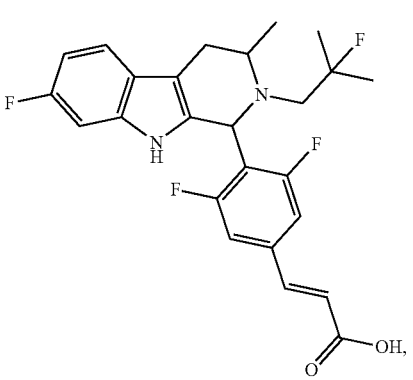
34
35

36
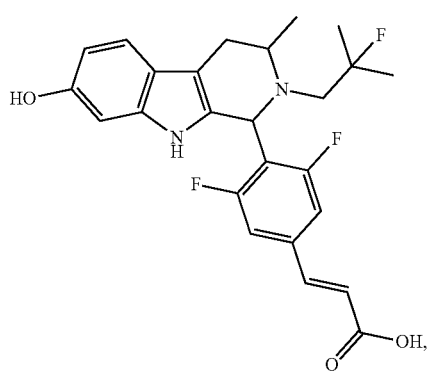
37
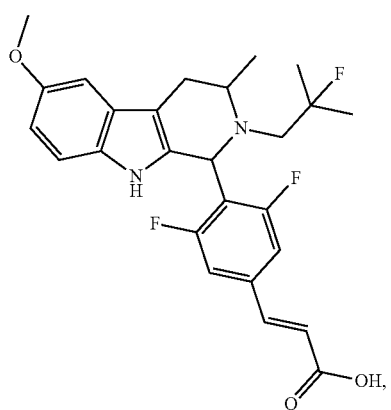
39
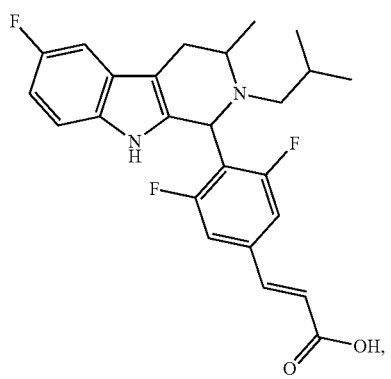
40
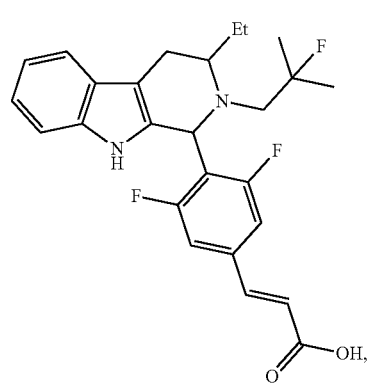
42
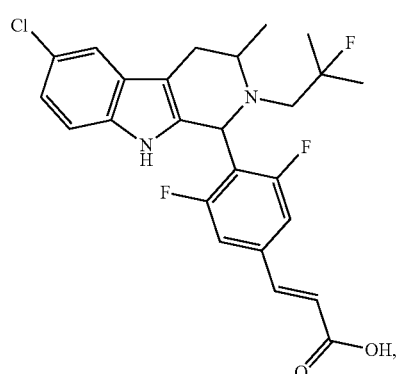
43
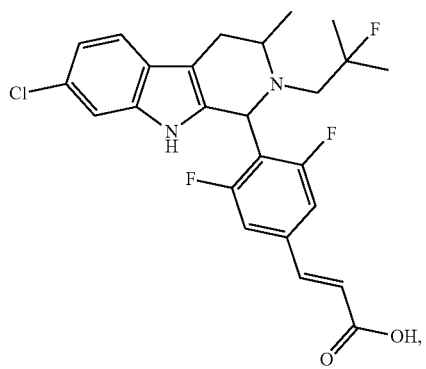
44
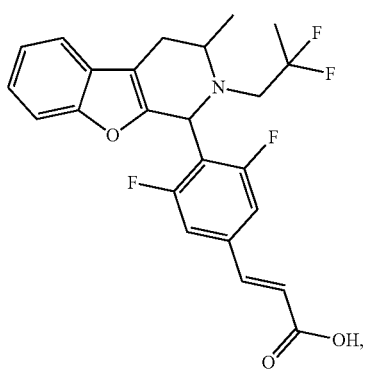
46
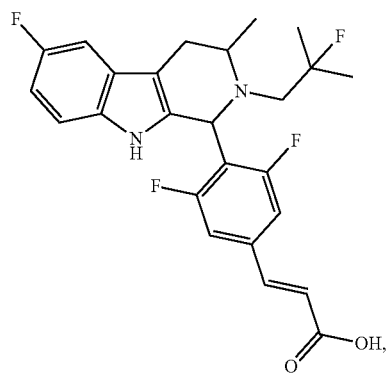

-continued

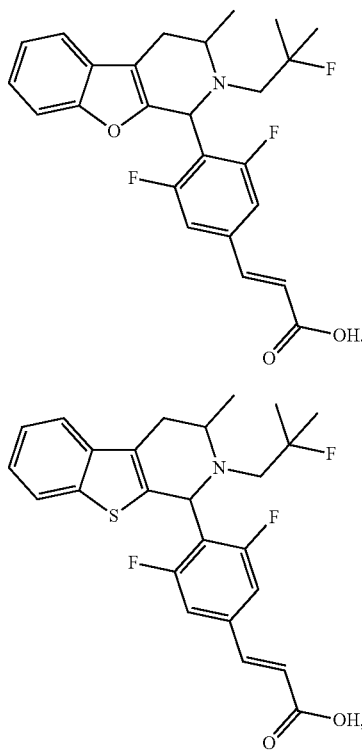

and pharmaceutically acceptable salts.

In another aspect, the present disclosure provides pharmaceutical compositions including one or more of the compounds described herein, and a pharmaceutically acceptable excipient. In certain embodiments, the pharmaceutical compositions described herein include an effective amount of a SERD compound as described herein. An effective amount described herein may be a therapeutically effective amount or prophylactically effective amount.

In yet another aspect, the present disclosure provides methods for treating a proliferative disease (e.g., ER+ breast cancer, which may have wildtype or mutated ER), the method comprising administering to a subject in need of the treatment an effective amount of any of the pharmaceutical compositions described herein.

In certain embodiments, a target proliferative disease can be cancer, including, but not limited to, ER+ breast cancer or cancers driven by either wildtype-ER or mutant-ER.

In certain embodiments, the subject being treated is a mammal (e.g., human or non-human mammal).

Another aspect of the present disclosure relates to kits comprising a container with a compound, or pharmaceutical composition thereof, as described herein. The kits described herein may include a single dose or multiple doses of the compound or pharmaceutical composition. The kits may be useful in a method of the disclosure. In certain embodiments, the kit further includes instructions for using the compound or pharmaceutical composition.

In yet another aspect, the present disclosure provides compounds and pharmaceutical compositions described herein for use in treating a proliferative disease such as cancer as described herein and/or for manufacturing a medicament for use in treating the target disease.

The details of one or more embodiments of the disclosure are set forth herein. Other features, objects, and advantages of the disclosure will be apparent from the Detailed Description, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("C$_{1-10}$ alkyl"). In some embodiments, an alkyl group has 1 to 9 carbon atoms ("C$_{1-9}$ alkyl"). In some embodiments, an alkyl group has 1 to 8 carbon atoms ("C$_{1-8}$ alkyl"). In some embodiments, an alkyl group has 1 to 7 carbon atoms ("C$_{1-7}$ alkyl"). In some embodiments, an alkyl group has 1 to 6 carbon atoms ("C$_{1-6}$ alkyl"). In some embodiments, an alkyl group has 1 to 5 carbon atoms ("C$_{1-5}$ alkyl"). In some embodiments, an alkyl group has 1 to 4 carbon atoms ("C$_{1-4}$ alkyl"). In some embodiments, an alkyl group has 1 to 3 carbon atoms ("C$_{1-3}$ alkyl"). In some embodiments, an alkyl group has 1 to 2 carbon atoms ("C$_{1-2}$ alkyl"). In some embodiments, an alkyl group has 1 carbon atom ("C$_1$ alkyl"). In some embodiments, an alkyl group has 2 to 6 carbon atoms ("C$_{2-6}$ alkyl"). Examples of C$_{1-6}$ alkyl groups include methyl (C$_1$), ethyl (C$_2$), propyl (C$_3$) (e.g., n-propyl, isopropyl), butyl (C$_4$) (e.g., n-butyl, tert-butyl, sec-butyl, iso-butyl), pentyl (C$_5$) (e.g., n-pentyl, 3-pentanyl, amyl, neopentyl, 3-methyl-2-butanyl, tertiary amyl), and hexyl (C$_6$) (e.g., n-hexyl). Additional examples of alkyl groups include n-heptyl (C$_7$), n-octyl (C$_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted C$_{1-10}$ alkyl (such as unsubstituted C$_{1-6}$ alkyl, e.g., —CH$_3$). In certain embodiments, the alkyl group is a substituted C$_{1-10}$ alkyl (such as substituted C$_{1-6}$ alkyl, e.g., —CF$_3$).

"Alkenyl" refers to a radical of a straight-chain or branched hydrocarbon group having from 2 to 20 carbon atoms, one or more carbon-carbon double bonds, and no triple bonds ("C$_{2-20}$ alkenyl"). In some embodiments, an alkenyl group has 2 to 10 carbon atoms ("C$_{2-10}$ alkenyl"). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted C$_{2-10}$ alkenyl. In certain embodiments, the alkenyl group is substituted C$_{2-10}$ alkenyl. In an alkenyl group, a C═C double bond for which the stereochemistry is not specified (e.g., —CH═CHCH$_3$ or

)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("C$_{2-20}$ alkynyl"). In some embodiments, an alkynyl group has 2 to 10 carbon atoms ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted C$_{2-10}$ alkynyl. In certain embodiments, the alkynyl group is substituted C$_{2-10}$ alkynyl.

"Carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted C$_{3-10}$ carbocyclyl. In certain embodiments, the carbocyclyl group is substituted C$_{3-10}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted C$_{3-10}$ cycloalkyl. In certain embodiments, the cycloalkyl group is substituted C$_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a C$_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(OR$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR)N(R$^{ff}$)$_2$, —OC(=NR)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^f$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4$$^-$, PF$_4$$^-$, PF$_6$$^-$, AsF$_6$$^-$, SbF$_6$$^-$, B[3,5-(CF$_3$)$_2$C$_6$H$_3$]$_4$]$^-$, BPh$_4$$^-$, Al(OC(CF$_3$)$_3$)$_4$$^-$, and a carborane anion (e.g., CB$_{11}$H$_{12}$ or (HCB$_{11}$Me$_5$Br$_6$$^-$)). Exemplary counterions which may be multivalent include CO$_3$$^{2-}$, HPO$_4$$^{2-}$, PO$_4$$^{3-}$, B$_4$O$_7$$^{2-}$, SO$_4$$^{2-}$, S$_2$O$_3$$^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R, —SO$_2$OR, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_1$-10 alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethylcarbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include, but are not limited to, —R$^{aa}$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O) (OR$^{cc}$)$_2$, and —P(=O)(N(R$^{bb}$)$_2$)$_2$, wherein X, R$^{aa}$, R$^{bb}$, and R$^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris (levulinoyloxyphenyl)methyl, 4,4',4''-tris (benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Exemplary sulfur atom substituents include, but are not limited to, —R$^{aa}$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O) (OR$^{cc}$)$_2$, and —P(=O)(N(R$^{bb}$) 2)$_2$, wherein R$^{aa}$, R$^{bb}$, and R$^{cc}$ are as defined herein.

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms" or "carbon units") and does not include hydrogen atoms or heteroatoms. However, a non-chain substituent of a hydrocarbon chain may include any atoms, including hydrogen atoms, carbon atoms, and heteroatoms. For example, hydrocarbon chain —C$^A$H(C$^B$H$_2$CCH$_3$)— includes one chain atom C$^A$, one hydrogen atom on C$^A$, and non-chain substituent —(C$^B$H$_2$C$^C$H$_3$). The term "C$_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —CH(C$_2$H$_5$)— is a C$_1$ hydrocarbon chain, and

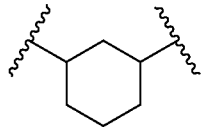 [SMILES: *C1CCCC(*)C1]

is a C$_3$ hydrocarbon chain. When a range of values is used, the meaning of the range is as described herein. For example, a C$_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —(CH$_2$)$_4$—). A hydrocarbon chain may also be unsaturated and include one or more C=C and/or C≡C bonds anywhere in the hydrocarbon chain. For instance, —CH=CH—(CH$_2$)$_2$—, —CH$_2$—C≡C—CH$_2$—, and —C≡C—CH=CH— are all examples of a unsubstituted and unsaturated hydrocarbon chain. In certain embodiments, the hydrocarbon chain is unsubstituted (e.g., —C≡C— or —(CH$_2$)$_4$—). In certain embodiments, the hydrocarbon chain is substituted (e.g., —CH(C$_2$H$_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring. For instance,

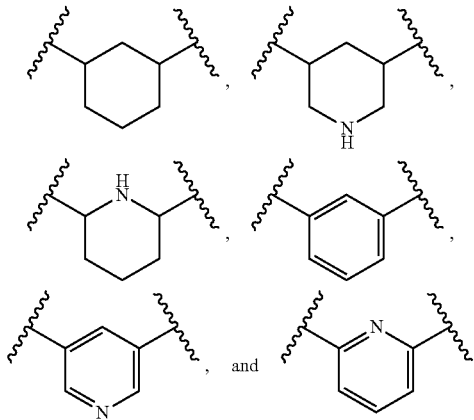

are all examples of a hydrocarbon chain. In contrast, in certain embodiments,

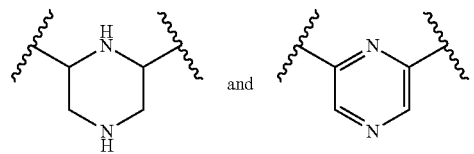 [SMILES: *C1CNCC(*)N1 ; *c1cncc(*)n1]

H and N are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

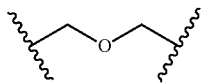

hydrocarbon chain wherein one chain atom is replaced with an oxygen atom.

The term "leaving group" is given its ordinary meaning in the art of synthetic organic chemistry and refers to an atom or a group capable of being displaced by a nucleophile. See, for example, Smith, *March Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is an activated substituted hydroxyl group (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein). In some cases, the leaving group is a sulfonic acid ester, such as toluenesulfonate (tosylate, —OTs), methanesulfonate (mesylate, —OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5$H_2O$)), and polyhydrates (x is a number greater than 1, e.g., dihydrates (R.2$H_2O$) and hexahydrates (R.6$H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, and a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "inhibition", "inhibiting", "inhibit," or "inhibitor" refer to the ability of a compound to reduce, slow, halt or prevent activity of a particular biological process in a cell relative to vehicle.

When a compound, pharmaceutical composition, method, use, or kit is referred to as "selectively," "specifically," or "competitively" binding a first protein, the compound binds the first protein with a higher binding affinity (e.g., not less than about 2-fold, not less than about 5-fold, not less than about 10-fold, not less than about 30-fold, not less than about 100-fold, not less than about 1,000-fold, or not less than about 10,000-fold) than binding a second protein or that is different from the first protein. When a compound is referred to as "selectively," "specifically," or "competitively" modulating (e.g., increasing or inhibiting) the activity of a protein, the compound modulates the activity of the protein to a greater extent (e.g., not less than about 2-fold, not less than about 5-fold, not less than about 10-fold, not less than about 30-fold, not less than about 100-fold, not less than about 1,000-fold, or not less than about 10,000-fold) than the activity of at least one protein that is different from the first protein.

The term "aberrant activity" refers to activity deviating from normal activity. The term "increased activity" refers to activity higher than normal activity.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. A "patient" refers to a human subject in need of treatment of a disease.

The terms "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen) to delay or prevent disease occurrence. Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of mutated gene (e.g., p53, Ras, and EGFR); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a breast cancer that has migrated to lung, liver and bone is said to be metastasized breast cancer and includes cancerous breast cancer cells growing in the lung, liver and bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, hematological malignancies. Exemplary cancers include, but are not limited to, bladder cancer; breast cancer (e.g., adenocarcinoma of the breast, papillary carcinoma of the breast, mammary cancer, medullary carcinoma of the breast); cervical cancer; urethral cancer; vaginal cancer; and vulvar cancer (e.g., Paget's disease of the vulva).

BRIEF DESCRIPTION OF THE DRAWINGS

Non-limiting embodiments of the present disclosure will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION

Figure 1:
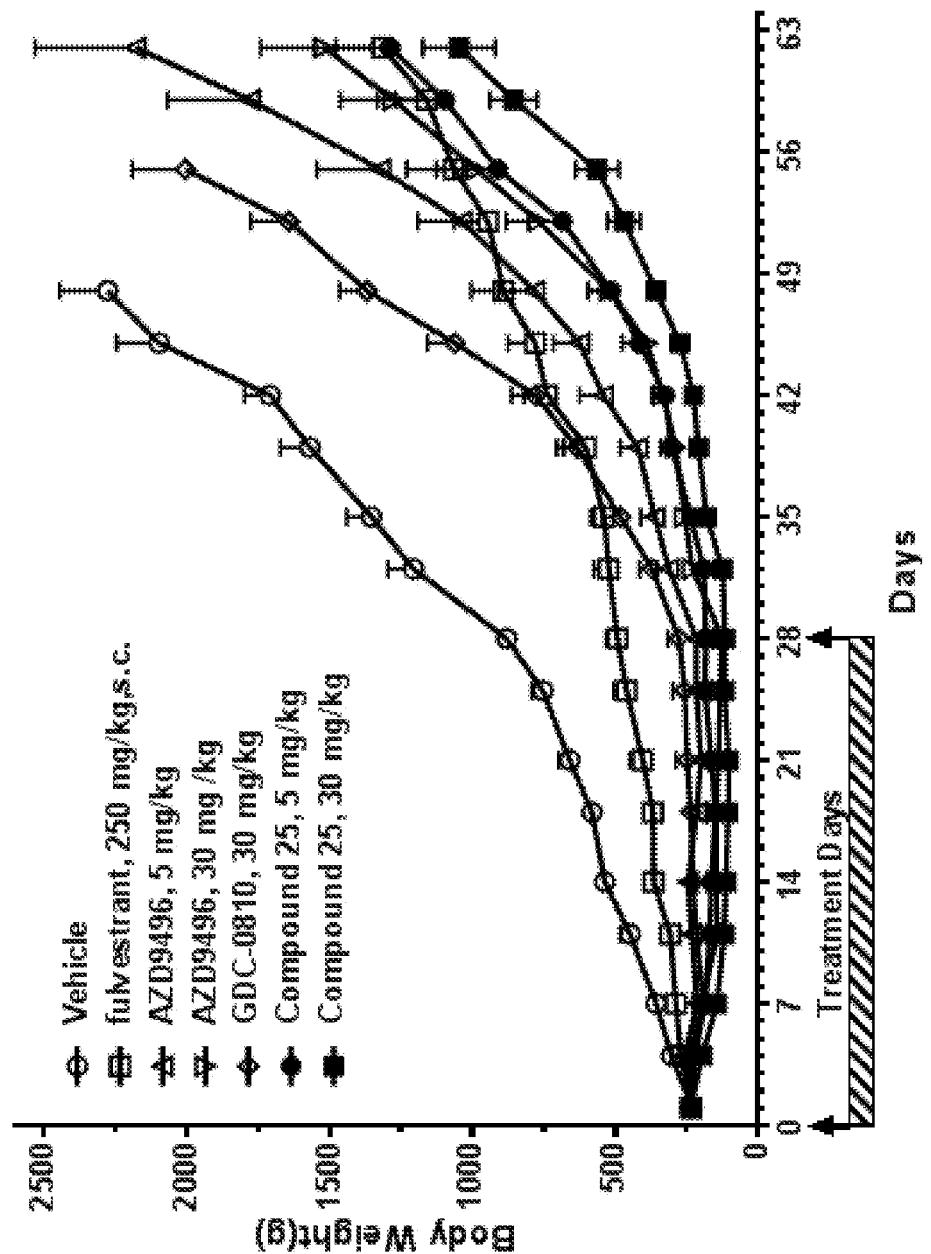
FIG. 1 is a chart showing the tumor volume change in a human breast cancer xMCF-7 xenograph efficacy study in a mouse model, under treatment by exemplary compound 25, compared with fulvestrant, GDC-0810 and AZD9496.

The present disclosure provides Selective Estrogen Receptor Degrader (SERD) compounds, for example, the compounds of Formula (I), which selectively binds an estrogen receptor and lead to the degradation of the receptor. The compounds described herein are useful in reducing the level of an estrogen receptor (wildtype or mutated) and treating a disease associated with a steroid hormone such as estrogen (e.g., breast cancer such as ER+ breast cancer). For example, the exemplary SERD compounds disclosed herein successfully induce degradation of ER and inhibit the growth of MCF-7 cancer cell, an ER+ human breast cancer cell line. Also provided in the present disclosure are pharmaceutical compositions, kits, methods of using the SERD compounds described herein for treating any of the target diseases described herein.

Selective Estrogen Receptor Degraders

One aspect of the present disclosure relates to the SERD compounds as described herein, as well as their pharmaceutically acceptable salts, solvates, hydrates, polymorphs, co-crystals, tautomers, stereoisomers, isotopically labeled derivatives, or prodrugs. These compounds are useful in treating and/or preventing proliferative diseases (such as ER+ breast cancer) or diseases associated with ER in a subject.

In certain embodiments, a compound described herein is of Formula (I):

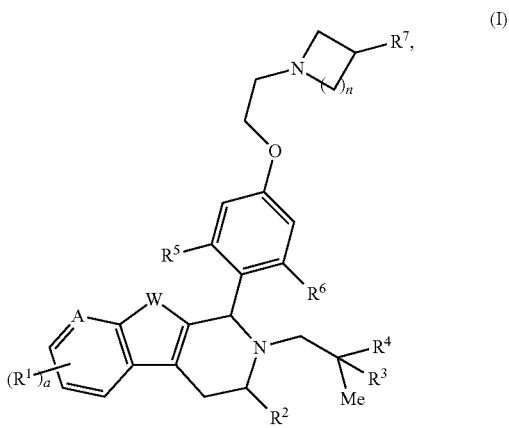

(I)

in which $R^1$-$R^7$, A, W, a, and n are as described herein, or pharmaceutically acceptable salt, solvate, hydrate, polymorph, co-crystal, tautomer, stereoisomer, isotopically labeled derivative, or prodrug thereof.

In Formula (I), A and W are in a tricyclic ring. In some embodiments, A can be $-CR^A=$ or $-N=$. In some embodiments, A can be $-CR^A=$, in which $R^A$ is as defined herein. In some embodiments, $R^A$ can be hydrogen. In some embodiments, $R^A$ can be substituted or unsubstituted $C_{1-6}$ alkyl (e.g., methyl, ethyl, or propyl). In one example, A can be $-CH=$. In another example, A can be $-CMe=$. In another embodiments, A can be $-NH=$.

In some embodiments, W can be $-NH-$. In some embodiments, W can be $-O-$. In some embodiments, W can be $-S-$.

Formula (I) includes one or more instances of $R^1$. In some embodiments, a can be 1. In some embodiments, a can be 2. In some embodiments, a can be 3. In some embodiments, at least one instance of $R^1$ can be hydrogen. In some embodiments, at least one instance of $R^1$ can be halogen (e.g., F, Cl, Br, or I). In some embodiments, at least one instance of $R^1$ can be fluorine. In some embodiments, at least one instance of $R^1$ can be chlorine. In some embodiments, at least one instance of $R^1$ can be substituted or unsubstituted $C_{1-6}$ alkyl (e.g., methyl, ethyl, or propyl). In some embodiments, at least one instance of $R^1$ can be $-CF_3$. In some embodiments, at least one instance of $R^1$ can be $-OR^A$, in which $R^A$ is as defined herein. In some embodiments, at least one instance of $R^1$ can be $-OMe$. In some embodiments, at least one instance of $R^1$ can be $-OEt$. In some embodiments, at least one instance of $R^1$ can be $-CN$.

In Formula (I), in some embodiments, $R^2$ can be hydrogen. In some embodiments, $R^2$ can be substituted or unsubstituted $C_{1-6}$ alkyl (e.g., methyl, ethyl, or propyl). In some embodiments, $R^2$ can be methyl. In some embodiments, $R^2$ can be ethyl. In some embodiments, $R^2$ can be propyl. In some embodiments, $R^2$ can be $-CF_3$. In some embodiments, $R^2$ can be substituted or unsubstituted carbocyclyl (e.g., substituted or unsubstituted, 3- to 7-membered, monocyclic carbocyclyl comprising zero, one, or two double bonds in the carbocyclic ring system). In some embodiments, $R^2$ can be cyclopropyl. In some embodiments, $R^2$ can be cyclobutyl.

In Formula (I), in some embodiments, $R^3$ and/or $R^4$ can be hydrogen. In some embodiments, $R^3$ and/or $R^4$ can be halogen (e.g., F, Cl, Br, or I). In some embodiments, $R^3$ and/or $R^4$ can be fluorine. In some embodiments, $R^3$ and/or $R^4$ can be substituted or unsubstituted $C_{1-6}$ alkyl (e.g., methyl, ethyl, or propyl). In some embodiments, $R^3$ and/or $R^4$ can be methyl. In some embodiments, $R^3$ and/or $R^4$ can be ethyl. In some embodiments, $R^3$ and/or $R^4$ can be propyl. In some embodiments, one of $R^3$ and $R^4$ can be fluorine, and the other of $R^3$ and $R^4$ can be substituted or unsubstituted $C_{1-6}$ alkyl (e.g., methyl). In some embodiments, one of $R^3$ and $R^4$ can be fluorine, and the other of $R^3$ and $R^4$ can be methyl. In some embodiments, both $R^3$ and $R^4$ can be fluorine. In some embodiments, both $R^3$ and $R^4$ can be methyl. In some embodiments, $R^3$ and/or $R^4$ can be substituted or unsubstituted carbocyclyl (e.g., substituted or unsubstituted, 3- to 7-membered, monocyclic carbocyclyl comprising zero, one, or two double bonds in the carbocyclic ring system). In some embodiments, $R^3$ and/or $R^4$ can be substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In some embodiments, $R^3$ and/or $R^4$ can be substituted or unsubstituted aryl (e.g., phenyl, or benzyl). In some embodiments, $R^3$ and/or $R^4$ can be substituted or unsubstituted 5- to 7-membered monocyclic heteroaryl, wherein one, two, three, or four atoms in the heteroaryl ring system are independently nitrogen, oxygen, or sulfur. In some embodiments, $R^3$ and/or $R^4$ can be $-OR^A$, in which $R^A$ is as defined herein (e.g., $-OH$, $-O$(substituted or unsubstituted $C_{1-6}$ alkyl) (e.g., $-OMe$)). In some embodiments, $R^3$ and/or $R^4$ can be $-N(R^B)_2$, in which $R^B$ is as defined herein (e.g., $-NH_2$).

In Formula (I), in some embodiments, $R^5$ and/or $R^6$ can be hydrogen. In some embodiments, $R^5$ and/or $R^6$ can be halogen (e.g., F, Cl, Br, or I). In some embodiments, $R^5$ and/or $R^6$ can be chlorine. In some embodiments, $R^5$ and/or $R^6$ can be substituted or unsubstituted $C_{1-6}$ alkyl (e.g., methyl, ethyl, or propyl). In some embodiments, $R^5$ and $R^6$ can both be halogen. In some embodiments, $R^5$ and $R^6$ can both be fluorine. In some embodiments, $R^5$ and $R^6$ can both be chlorine. In some embodiments, one of $R^5$ and $R^6$ can be chlorine, and the other one can be fluorine. In some embodiments, one of $R^5$ and $R^6$ can be fluorine, and the other one can be substituted or unsubstituted $C_{1-6}$ alkyl. In some embodiments, one of $R^5$ and $R^6$ can be chlorine, and the other one can be substituted or unsubstituted $C_{1-6}$ alkyl.

In Formula (I), in some embodiments, $R^7$ can be hydrogen. In some embodiments, $R^7$ can be halogen (e.g., F, Cl, Br, or I). In some embodiments, $R^7$ can be substituted or unsubstituted $C_{1-6}$ alkyl (e.g., methyl, ethyl, or propyl). In some embodiments, $R^7$ can be of the formula: —$CH_2R^a$, in which $R^a$ is halogen. In some embodiments, $R^7$ can be —$CH_2F$. In some embodiments, $R^7$ can be —$OR^A$, in which $R^A$ is as defined herein (e.g., —OH, —O (substituted or unsubstituted $C_{1-6}$ alkyl) (e.g., —OMe)). In some embodiments, $R^7$ can be —$N(R^B)_2$, in which $R^B$ is as defined herein (e.g., —$NH_2$).

In Formula (I), in some embodiments, n can be 1. In some embodiments, n can be 2. In some embodiments, n can be 3. In some embodiments, n can be 4.

In certain embodiments, a compound described herein is of Formula (II):

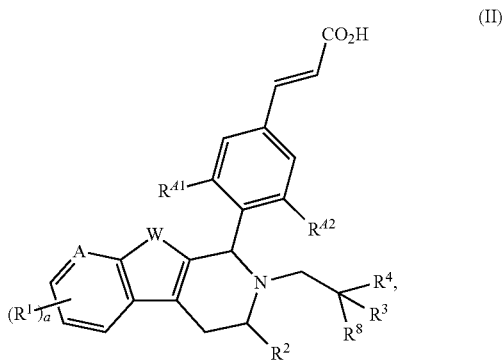

(II)

in which $R^1$-$R^4$, $R^8$, $R^{A1}$, $R^{A2}$, A, W, and a are as described herein, or pharmaceutically acceptable salt, solvate, hydrate, polymorph, co-crystal, tautomer, stereoisomer, isotopically labeled derivative, or prodrug thereof.

In Formula (II), A and W are in a tricyclic ring. In some embodiments, A can be —$CR^A$= or —N=. In some embodiments, A can be —$CR^A$=, in which $R^A$ is as defined herein. In some embodiments, $R^A$ can be hydrogen. In some embodiments, $R^A$ can be substituted or unsubstituted $C_{1-6}$ alkyl (e.g., methyl, ethyl, or propyl). In one example, A can be —CH=. In one example, A can be —CMe=. In another embodiments, A can be —NH=.

In some embodiments, W can be —NH—. In some embodiments, W can be —O—. In some embodiments, W can be —S—.

Formula (II) includes one or more instances of $R^1$. In some embodiments, a can be 1. In some embodiments, a can be 2. In some embodiments, a can be 3. In some embodiments, at least one instance of $R^1$ can be hydrogen. In some embodiments, at least one instance of $R^1$ can be halogen (e.g., F, Cl, Br, or I). In some embodiments, at least one instance of $R^1$ can be fluorine. In some embodiments, at least one instance of $R^1$ can be chlorine. In some embodiments, at least one instance of $R^1$ can be substituted or unsubstituted $C_{1-6}$ alkyl (e.g., methyl, ethyl, or propyl). In some embodiments, at least one instance of $R^1$ can be substituted or unsubstituted methyl. In some embodiments, at least one instance of $R^1$ can be —$CF_3$. In some embodiments, at least one instance of $R^1$ can be substituted or unsubstituted ethyl. In some embodiments, at least one instance of $R^1$ can be substituted or unsubstituted propyl. In some embodiments, at least one instance of $R^1$ can be —$OR^A$, in which $R^A$ is as defined herein. In some embodiments, at least one instance of $R^1$ can be —OH. In some embodiments, at least one instance of $R^A$ can be substituted or unsubstituted $C_{1-6}$ alkyl. In some embodiments, at least one instance of $R^1$ can be —OMe. In some embodiments, at least one instance of $R^1$ can be —CN.

In Formula (II), in some embodiments, $R^2$ can be hydrogen. In some embodiments, $R^2$ can be substituted or unsubstituted $C_{1-6}$ alkyl (e.g., methyl, ethyl, or propyl). In some embodiments, $R^2$ can be substituted or unsubstituted methyl. In some embodiments, $R^2$ can be —$CF_3$. In some embodiments, $R^2$ can be substituted or unsubstituted ethyl. In some embodiments, $R^2$ can be substituted or unsubstituted propyl. In some embodiments, $R^2$ can be substituted or unsubstituted carbocyclyl (e.g., substituted or unsubstituted, 3- to 7-membered, monocyclic carbocyclyl comprising zero, one, or two double bonds in the carbocyclic ring system). In some embodiments, $R^2$ can be substituted or unsubstituted cyclopropyl.

In Formula (II), in some embodiments, $R^3$ and/or $R^4$ can be hydrogen. In some embodiments, $R^3$ and/or $R^4$ can be halogen (e.g., F, Cl, Br, or I). In some embodiments, $R^3$ and/or $R^4$ can be fluorine. In some embodiments, $R^3$ and $R^4$ can both be fluorine. In some embodiments, $R^3$ and/or $R^4$ can be substituted or unsubstituted $C_{1-6}$ alkyl (e.g., methyl, ethyl, or propyl). In some embodiments, $R^3$ and/or $R^4$ can be methyl. In some embodiments, one of $R^3$ and $R^4$ can be fluorine, and the other can be methyl. In some embodiments, one of $R^3$ and $R^4$ can be fluorine, and the other can be hydrogen. In some embodiments, one of $R^3$ and $R^4$ can be methyl, and the other can be hydrogen. In some embodiments, $R^3$ and/or $R^4$ can be substituted or unsubstituted carbocyclyl (e.g., substituted or unsubstituted, 3- to 7-membered, monocyclic carbocyclyl comprising zero, one, or two double bonds in the carbocyclic ring system). In some embodiments, $R^3$ and/or $R^4$ can be substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In some embodiments, $R^3$ and/or $R^4$ can be substituted or unsubstituted aryl (e.g., phenyl, or benzyl). In some embodiments, $R^3$ and/or $R^4$ can be substituted or unsubstituted 5- to 7-membered monocyclic heteroaryl, wherein one, two, three, or four atoms in the heteroaryl ring system are independently nitrogen, oxygen, or sulfur. In some embodiments, $R^3$ and/or $R^4$ can be —$OR^A$, in which $R^A$ is as defined herein (e.g., —OH, —O(substituted or unsubstituted $C_{1-6}$ alkyl) (e.g., —OMe)). In some embodiments, $R^3$ and/or $R^4$ can be —$N(R^B)_2$, in which $R^B$ is as defined herein (e.g., —$NH_2$). In some embodiments, $R^3$ and $R^4$ can be taken together with the intervening atoms to form substituted or unsubstituted carbocyclyl (e.g., substituted or unsubstituted, 3- to 7-membered, monocyclic carbocyclyl comprising zero, one, or two double bonds in the carbocyclic ring system). In some embodiments, $R^3$ and $R^4$ can be taken together with the intervening atoms to form substituted or unsubstituted cyclopropyl. In some embodiments, $R^3$ and $R^4$ can be taken together with the intervening atoms to form unsubstituted cyclopropyl, and $R^8$ can be fluorine. In some embodiments, $R^3$ and $R^4$ can be taken together with the intervening atoms to form unsubstituted cyclopropyl, and $R^8$ can be methyl. In some embodiments, $R^3$ and $R^4$ can be taken together with the intervening atoms to form substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur).

In Formula (II), in some embodiments, $R^8$ can be hydrogen. In some embodiments, $R^8$ can be halogen (e.g., F, Cl, Br, or I). In some embodiments, $R^8$ can be fluorine. In some embodiments, $R^8$ can be substituted or unsubstituted methyl. In some embodiments, $R^8$ can be methyl.

In Formula (II), in some embodiments, $R^{A1}$ and/or $R^{A2}$ can be substituted or unsubstituted $C_{1-6}$ alkyl (e.g., methyl, ethyl, or propyl). In some embodiments, $R^{A1}$ and/or $R^{A2}$ can be substituted or unsubstituted methyl. In some embodiments, $R^{A1}$ and/or $R^{A2}$ can be substituted or unsubstituted ethyl. In some embodiments, $R^{A1}$ and/or $R^{A2}$ can be substituted or unsubstituted propyl. In some embodiments, $R^{A1}$ and/or $R^{A2}$ can be chlorine. In some embodiments, $R^{A1}$ and/or $R^{A2}$ can be fluorine. In some embodiments, either $R^{A1}$ or $R^{A2}$ can be chlorine. In some embodiments, both $R^{A1}$ and $R^{A2}$ can be chlorine. In some embodiments, one of $R^{A1}$ or $R^{A2}$ can be fluorine, and the other one of $R^{A1}$ and $R^{A2}$ can be selected from the group consisting of substituted or unsubstituted alkyl, chlorine, and fluorine. In some embodiments, one of $R^{A1}$ or $R^{A2}$ can be fluorine, and the other one of $R^{A1}$ and $R^{A2}$ can be substituted or unsubstituted $C_{1-6}$ alkyl (e.g., methyl, ethyl, or propyl). In some embodiments, one of $R^{A1}$ or $R^{A2}$ can be fluorine, and the other one of $R^{A1}$ and $R^{A2}$ can be methyl. In some embodiments, one of $R^{A1}$ or $R^{A2}$ can be fluorine, and the other one of $R^{A1}$ and $R^{A2}$ can be chlorine. In some embodiments, both $R^{A1}$ and $R^{A2}$ can be fluorine.

In some embodiments, the compound of Formula (I) can be of the formula of the compounds described herein, or a pharmaceutically acceptable salt, solvate, hydrate, polymorph, co-crystal, tautomer, stereoisomer, isotopically labeled derivative, or prodrug thereof.

In some embodiments, the compound of Formula (II) can be of the formula of the compounds described herein, or a pharmaceutically acceptable salt, solvate, hydrate, polymorph, co-crystal, tautomer, stereoisomer, isotopically labeled derivative, or prodrug thereof.

The compounds described herein can be prepared from readily available starting materials using methods known in the art. It will be appreciated that where typical or preferred process conditions (i.e., reaction temperatures, times, mole ratios of reactants, solvents, and pressures, etc.) are given, other process conditions can also be used unless otherwise stated. Optimum reaction conditions may vary with the particular reactants or solvents used, but such conditions can be determined by those skilled in the art by routine optimization procedures. The chemicals used in the above-described synthetic routes may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the compounds. In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The compounds of Formula (I) and Formula (II) provided herein can be prepared from readily available starting materials using the following general methods and procedures. Exemplary schematic illustrations for synthesizing the compounds of the invention described herein are provided below. Where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

The compounds described herein, e.g., compounds of formula (I), may be prepared according to the general Scheme A. Compounds A1, are commercially available or can be synthesized via standard transformations known to those of ordinary skill in the art of organic/medicinal chemistry. Compounds A3 can be prepared by Pictet-Spengler reaction of A1 with aldehyde A2 (X═I, Br, or Cl). Alkylation of A3 with A4 could produce compound A5. Alternatively, A5 could be prepared by alkylation of A1 with A4, followed by Pictet-Spengler reaction of A6 with aldehyde A2. Copper or palladium promoted C—O bond formation of compound A5 with ethylene glycol could provide compound A7. Derivatization of the OH group of A7 to a leaving group, followed by displacement with amine A8, could afford (I).

Scheme A. Exemplary Scheme for Preparation of Compounds of Formula (I)

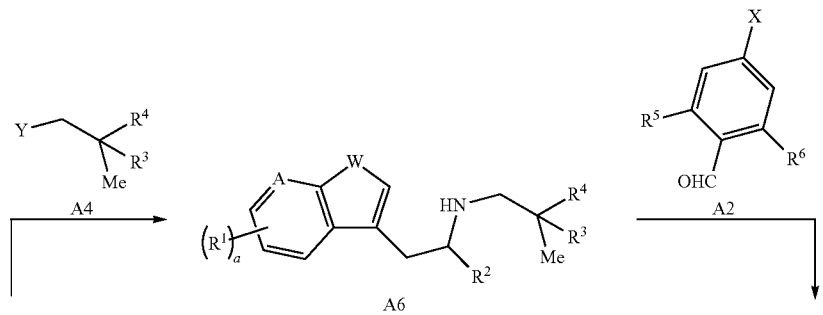

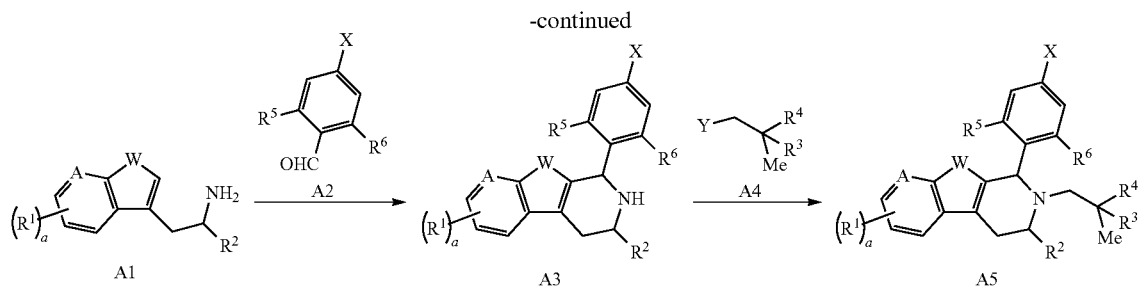

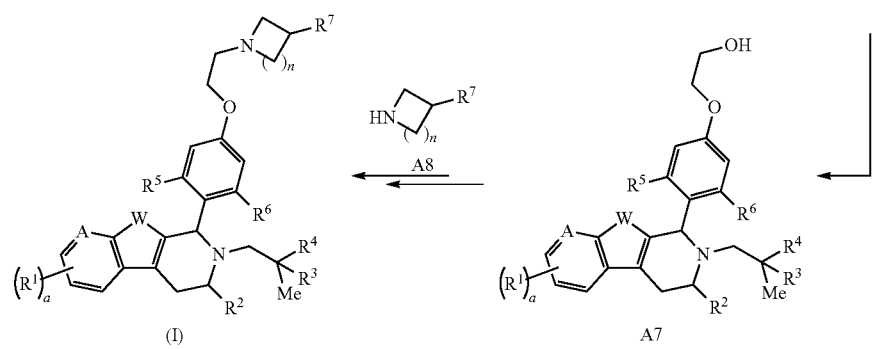

The compounds of formula (II) may be prepared according to the general Scheme B. Compounds B3, are commercially available or can be assembled via standard transformations known to those of ordinary proficiency in the art of organic/medicinal chemistry. Compounds B2 could be prepared by alkylation of A1 with B1. Pictet-Spengler reaction of B2 with aldehyde B3 could produce B4. The saponification of B4 to (II) could be generally accomplished by the use of an alkali metal hydroxide in aqueous or mixed aqueous/organic solvents.

Scheme B. Exemplary Scheme for Preparation of compounds of Formu;a (II)

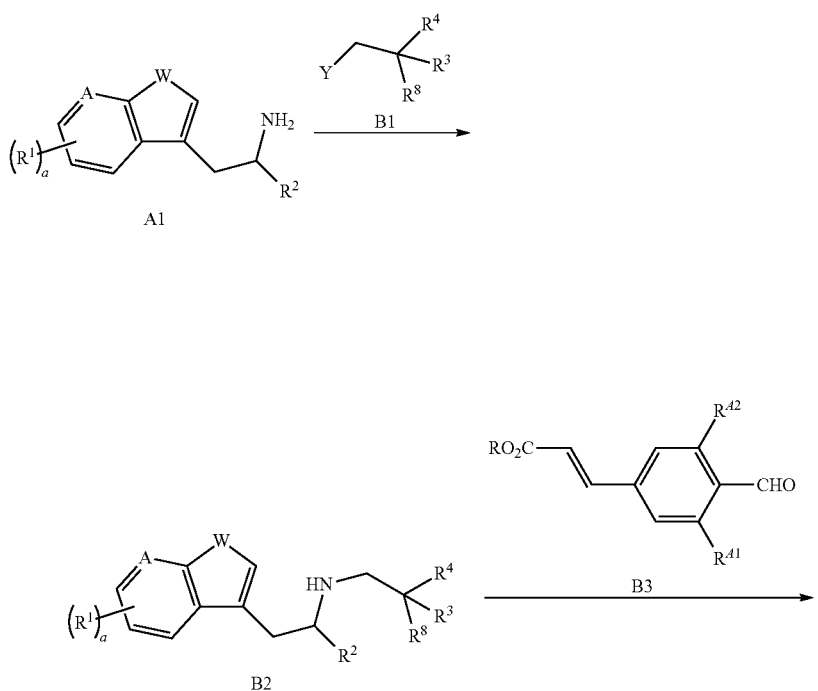

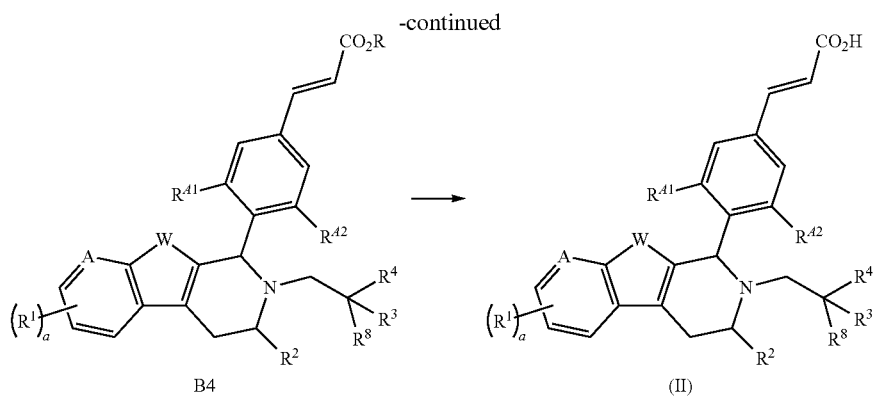

B4 → (II)

Alternatively, the compounds of formula (II) may be prepared according to the general Scheme C. Pictet-Spengler reaction of B2 with aldehyde C1 (X=I, Br, or Cl) could produce C2. Compounds C4 could be prepared by palladium mediated Heck reaction of C2 with C3. The saponification of C4 to (II) could be generally accomplished by the use of an alkali metal hydroxide in aqueous or mixed aqueous/organic solvents Scheme C.
Exemplary Scheme for Preparation of compounds of Formula (II)

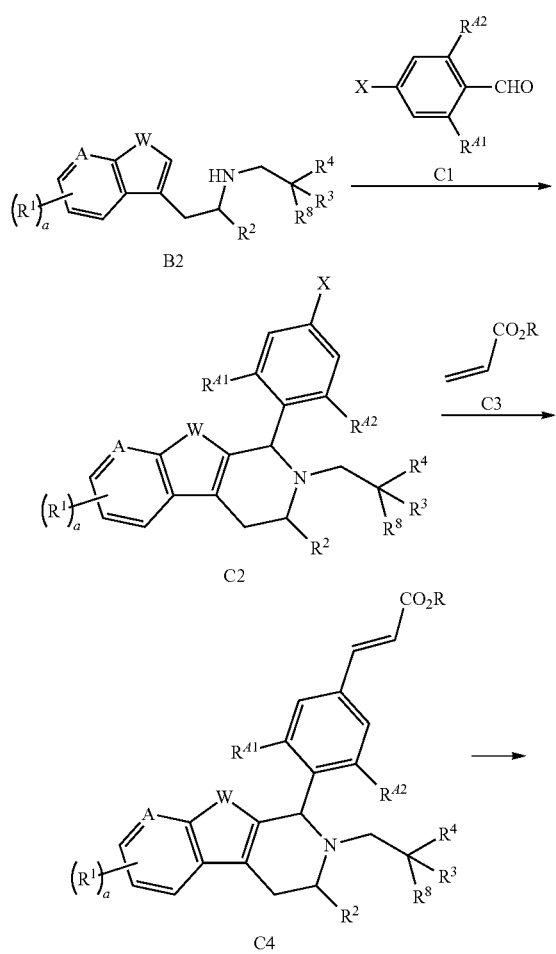

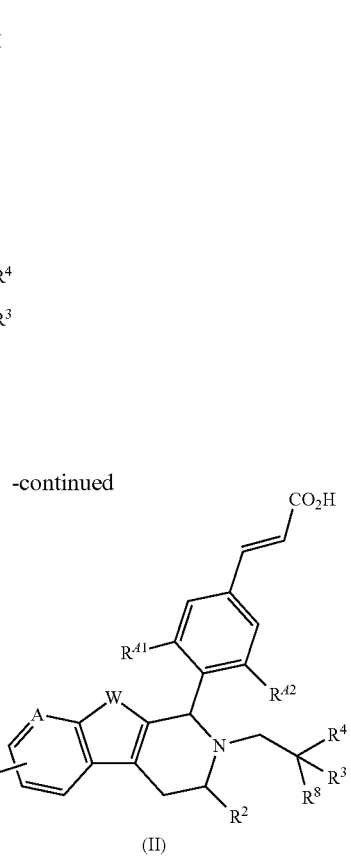

(II)

Pharmaceutical Compositions and Kits

The present disclosure provides pharmaceutical compositions comprising a compound described herein, or a pharmaceutically acceptable salt thereof, and optionally a pharmaceutically acceptable excipient. In certain embodiments, a pharmaceutical composition described herein comprises a compound described herein, or a pharmaceutically acceptable salt thereof, and a pharmaceutically acceptable excipient. The pharmaceutical compositions described herein are useful in treating and/or preventing proliferative diseases (e.g., ER+ breast cancer) or diseases associated with ER.

In certain embodiments, the cell contacted with an effective amount of a compound or pharmaceutical composition described herein is in vitro. In certain embodiments, the contacted cell is ex vivo. In certain embodiments, the cell described herein is in vivo. In certain embodiments, the cell described herein is a malignant cell (e.g., malignant breast cancer cell).

In certain embodiments, the compound described herein is provided in an effective amount in the pharmaceutical composition. In certain embodiments, the effective amount is a therapeutically effective amount (e.g., amount effective for treating a proliferative disease in a subject in need thereof). In certain embodiments, the proliferative disease is cancer, e.g., ER+ breast cancer. In certain embodiments, the effective amount is a prophylactically effective amount (e.g., amount effective for preventing a proliferative disease in a subject in need thereof and/or for keeping a subject in need thereof in remission of a proliferative disease).

Pharmaceutical compositions described herein can be prepared by any method known in the art of pharmacology. In general, such preparatory methods include bringing the compound described herein (i.e., the "active ingredient")

into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Although the descriptions of pharmaceutical compositions provided herein are mainly directed to pharmaceutical compositions which are suitable for administration to humans, such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

In certain embodiments, a kit described herein includes a first container comprising a compound or pharmaceutical composition described herein. In certain embodiments, a kit described herein is useful in treating a proliferative disease (e.g., ER+ breast cancer) in a subject in need thereof, and/or preventing a proliferative disease in a subject in need thereof. In some embodiments, the SERDs described herein are useful in treating diseases and/or disorders associated with a steroid hormone such as estrogen.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a proliferative disease in a subject in need thereof, and/or preventing a proliferative disease in a subject in need thereof. A kit described herein may include one or more additional pharmaceutical agents described herein as a separate composition.

Methods of Treatment

As shown in the Examples below, exemplary SERD compounds described herein successfully induced degradation of ER and inhibited the growth of ER+ breast cancer cells and exhibited better human hepatocyte clearance than drug of the same class such as fulvestrant, as well as those currently in clinical trials such as GDC-0810 and AZD9496. In mouse studies, these compounds also showed superior pharmacokinetic profiles (e.g., clearance, half life, and AUC) than drugs currently in clinical uses or clinical trials.

Accordingly, the present disclosure provides methods of treating a proliferative disease and/or a disease associated with a steroid hormone such as estrogen, in a subject in need thereof, the methods comprising administering to the subject an effective amount (e.g., therapeutically effective amount) of a compound, or pharmaceutical composition thereof, described herein.

Another aspect of the present disclosure relates to methods of preventing proliferative disease in a subject in need thereof, the methods comprising administering to the subject an effective amount (e.g., prophylactically effective amount) of a compound, or pharmaceutical composition thereof, described herein.

The compounds and pharmaceutical compositions described herein are useful in treating and/or preventing proliferative diseases. In certain embodiments, the proliferative disease is cancer. In certain embodiments, the proliferative disease is breast cancer. In certain embodiments, the proliferative disease is gynecological disease or cancer associated with ER such as cancer of the ovary, cervix or endometrium and breast cancer, particularly ER+ breast cancer.

In certain embodiments, the method described herein further includes administering to the subject an additional pharmaceutical agent. In certain embodiments, the method described herein further includes contacting the biological sample with an additional pharmaceutical agent. In certain embodiments, the method described herein further includes contacting the tissue with an additional pharmaceutical agent. In certain embodiments, the method described herein further includes contacting the cell with an additional pharmaceutical agent. In certain embodiments, the method described herein further includes radiotherapy, immunotherapy, and/or transplantation (e.g., bone marrow transplantation).

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops). Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the tissue or cell is three doses a day, two doses a day, one dose a day, one dose every other day, one dose every third day, or one dose every week. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, biological sample, tissue, or cell. In certain embodiments, the duration between the first dose and last dose of the multiple doses is three months, six months, or one year. In certain embodiments, the duration between the first dose and last dose of the multiple doses is the lifetime of the subject, biological sample, tissue, or cell. In certain embodiments, a dose (e.g., a single dose, or any dose of multiple doses) described herein includes independently between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein. In certain embodiments, a dose described herein includes independently between 100 mg and 300 mg, inclusive, of a compound as described herein. In certain embodiments, a dose described herein includes independently between 300 mg and 1000 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents) useful in treating and/or preventing a proliferative disease. The compounds or compositions can be administered in combination with additional pharmaceutical agents that improve their activity (e.g., activity (e.g., potency and/or efficacy) in treating a proliferative disease in a subject in need thereof, and/or in preventing a proliferative disease in a subject in need thereof), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies in treating and/or preventing a proliferative disease. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, antibodies, small molecules linked to proteins such as antibodies, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful in treating a proliferative disease. In certain embodiments, the additional pharmaceutical agent is a pharmaceutical agent useful in preventing a proliferative disease. In certain embodiments, the additional pharmaceutical agent is a pharmaceutical agent approved by a regulatory agency (e.g., the US FDA) for treating and/or preventing a proliferative disease. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the additional pharmaceutical agent is an anti-proliferative agent (e.g., anti-cancer agent, for example, an immune-oncology agents (e.g., anti-PD-1 antibody) or cells (e.g., CAR-T cells)). In certain embodiments, the additional pharmaceutical agent is an anti-angiogenesis agent, anti-inflammatory agent, immunosuppressant, anti-bacterial agent, anti-viral agent, cardiovascular agent, cholesterol-lowering agent, anti-diabetic agent, anti-allergic agent, pain-relieving agent, or a combination thereof. In certain embodiments, the compounds described herein or pharmaceutical compositions can be administered in combination with an anti-cancer therapy including, but not limited to, targeted therapy (e.g., mTOR signaling pathway inhibitor), cell therapy, surgery, radiation therapy, immunotherapy, and chemotherapy (e.g., docetaxel, doxorubicin).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Example 1: Synthesis of Compound 1 and Derivatives Thereof

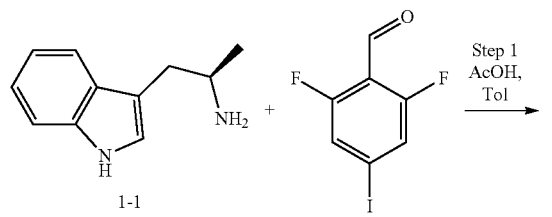

1-1

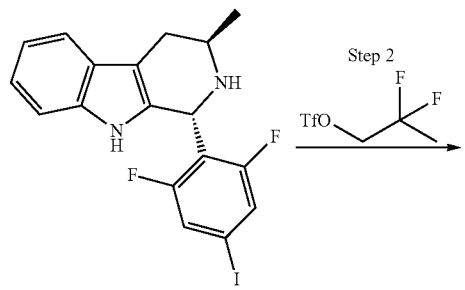

1-2

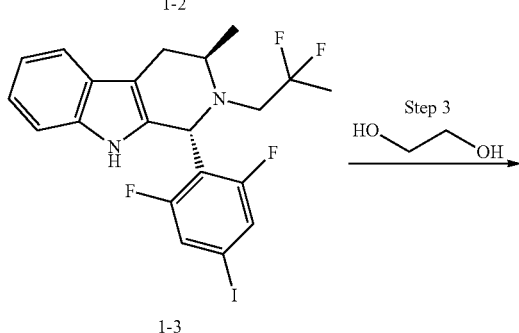

1-3

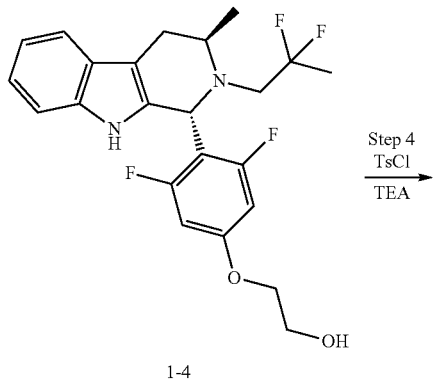

1-4

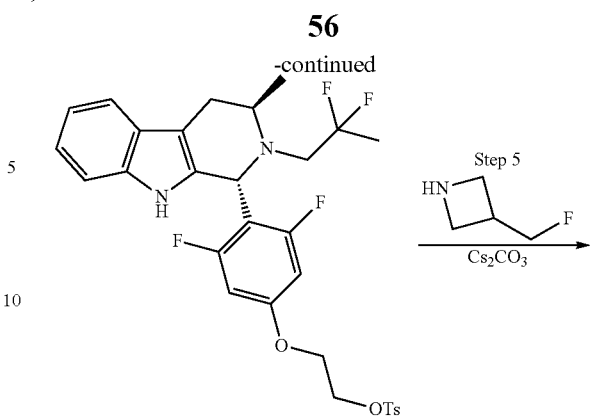

1-5

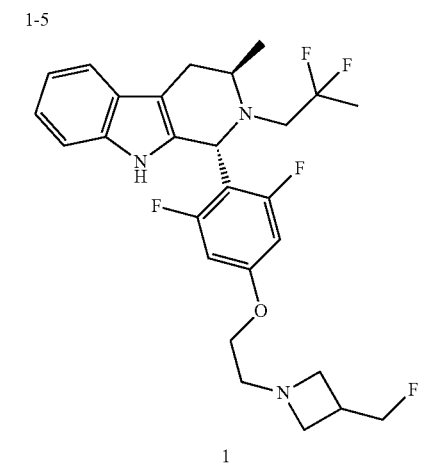

1

Step 1. Synthesis of 1-2

A solution of (2R)-1-(1H-indol-3-yl)propan-2-amine (2 g, 11.48 mmol), acetic acid (1 mL) and 2,6-difluoro-4-iodo-benzaldehyde (3 g, 11.19 mmol) in Toluene (20 mL) was stirred at 80° C. for 12 h. The resulting mixture was then cooled to room temperature and concentrated under vacuum. The residue was purified by a silica gel column with ethyl acetate/petroleum ether (1/100-1/10) as the eluent to afford the desired product (2 g, 42% yield).

Step 2. Synthesis of 1-3

To a solution of 1-2 (2 g, 4.71 mmol) in 1,4-dioxane (20 mL) were added N,N-diisopropylethylamine (920 mg, 7.08 mmol) and 2,2-difluoropropyl trifluoromethanesulfonate (1.61 g, 7.06 mmol). The resulting solution was stirred at 100° C. for 12 h. The reaction was cooled down to room temperature and then quenched with water (50 mL). The mixture was extracted with ethyl acetate (50 mL×3). The organic phase was washed with brine (50 mL) and concentrated under vacuum to afford the desired product (1.5 g, crude).

Step 3. Synthesis of 1-4

To a solution of 1-3 (500 mg, 1.00 mmol) in ethane-1,2-diol (5 mL) were added copper iodide (94.6 mg, 0.50 mmol), 1,10-phenanthroline (18 mg, 0.10 mmol) and cesium carbonate (649 mg, 1.99 mmol). The resulting mixture was then stirred at 100° C. for 2 h. After cooling to room temperature, the mixture was diluted with water (20 mL), and extracted with ethyl acetate (30 mL×3). The organic phase was washed with brine (20 mL) and concentrated under vacuum. The residue was purified by silica gel column eluting with ethyl acetate/petroleum ether (1/100-1/10) to afford the desired product (200 mg, 46% yield).

Step 4. Synthesis of 1-5

To a solution of 1-4 (50 mg, 0.11 mmol) in tetrahydrofuran (2 mL), were added triethylamine (13.9 mg, 0.14 mmol) and 4-methylbenzene-1-sulfonyl chloride (26 mg, 0.14 mmol). The resulting mixture was then stirred at room temperature for 3 h. The mixture was diluted with water (10 mL), and extracted with ethyl acetate (10 mL×3). The organic phase was dried over anhydrous sodium sulfate and concentrated under vacuum to afford the desired product (50 mg, 74% yield).

Step 5. Synthesis of 1

A solution of 1-5 (50 mg, 0.08 mmol), 3-(fluoromethyl) azetidine (20.47 mg, 0.23 mmol), and cesium carbonate (41.5 mg, 0.13 mmol) in acetonitrile (2 mL) was stirred at 80° C. for 12 h. After cooling to room temperature, the mixture was diluted with water (10 mL), and extracted with ethyl acetate (10 mL×3). The organic phase was concentrated under vacuum. The residue was purified by silica gel column eluting with ethyl acetate/petroleum ether (1/100-1/5) to afford the desired product (19.7 mg, 46%). LCMS (ES, m/z): 508.4. $^1$HNMR (300 MHz, CDCl$_3$, ppm): δ 7.41 (d, J=6.9 Hz, 1H), 7.19-7.17 (d, J=7.2 Hz, 1H), 7.03-6.95 (m, 2H) 6.64-6.59 (m, 2H), 5.24 (s, 1H), 4.61 (d, J=3.9 Hz, 1H), 4.46 (d, J=3.9 Hz, 1H), 4.18-4.10 (m, 4H), 3.96-3.90 (m, 2H), 3.57-3.55 (m, 1H), 3.44-3.41 (m, 2H), 3.31-3.10 (m, 1H), 3.10-2.95 (m, 2H), 2.65-2.60 (m, 2H), 1.42 (t, J=18.9 Hz, 3H), 1.13 (d, J=6.6 Hz, 3H).

Using the similar procedures described above, the following additional compounds of the invention were prepared.

TABLE 1

Exemplary Derivatives of Compound 1

| Example No. | Compound | [M + H]$^+$ | HNMR |
|---|---|---|---|
| 2 | 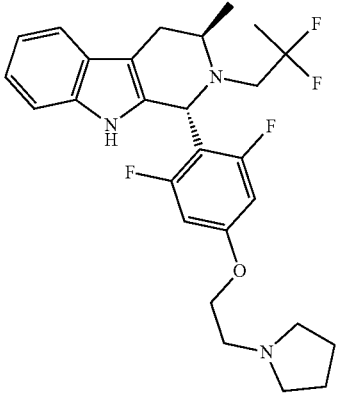 [SMILES: C[C@@H]1Cc2c([nH]c3ccccc23)[C@@H](c2c(F)cc(OCCN3CCCC3)cc2F)N1CC(C)(F)F] | 490.3 | $^1$HNMR (300 MHz, CD$_3$OD, ppm): δ 7.44 (d, J = 6.9 Hz, 1H), 7.22 (d, J = 7.2 Hz, 1H), 7.07-6.97 (m, 2H), 6.64-6.59 (m, 2H), 5.27 (s, 1H), 4.16 (t, J = 5.4 Hz, 2H), 3.65-3.59 (m, 1H), 3.11-3.01 (m, 2H), 2.96 (t, J = 5.4 Hz, 2H), 2.75-2.61 (m, 6H), 2.00-1.85 (m, 4H), 1.45 (t, J = 18.6 Hz, 3H), 1.18 (d, J = 6.6 Hz, 3H). |
| 3 | 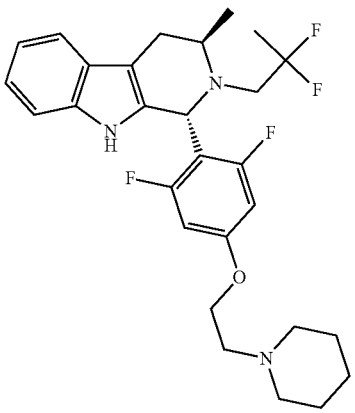 [SMILES: C[C@@H]1Cc2c([nH]c3ccccc23)[C@@H](c2c(F)cc(OCCN3CCCCC3)cc2F)N1CC(C)(F)F] | 540.3 | $^1$HNMR (300 MHz, CDCl$_3$, ppm): δ 7.43 (d, J = 7.2 Hz, 1H), 7.11 (d, J = 8.1 Hz, 1H), 7.06-6.95 (m, 2H), 6.62-6.57 9m, 2H), 5.25 (s, 1H), 4.15 (t, J = 5.4 Hz, 2H), 3.63-3.57 (m, 1H), 3.10-3.00 (m, 2H), 2.90 (t, J = 5.4 Hz, 2H), 2.69-2.56 (m, 6H), 1.69-1.68 (m, 4H), 1.52-1.46 (m, 2H), 1.43 (t, J = 18.9 Hz, 3H), 1.16 (d, J = 6.6 Hz, 3H). |

TABLE 1-continued

Exemplary Derivatives of Compound 1

| Example No. | Compound | [M + H]+ | HNMR |
|---|---|---|---|
| 4 | | 518.3 | ¹HNMR (300 MHz, CD₃OD, ppm): δ 7.43 (d, J = 8.4 Hz, 1H), 7.19 (d, J = 7.2 Hz, 1H), 7.06-6.96 (m, 2 H), 6.62-6.57 (m, 2H), 5.25 (s, 1H), 4.13 (t, J = 5.7 Hz, 2H), 3.66-3.56 (m, 1H), 3.13-2.96 (m, 4H), 2.85-2.8 1m, 4H), 2.69-2.59 (m, 2H), 1.72-1.67 (m, 8H), 1.43 (t, J = 18.6 Hz, 3 H) 1.16 (d, J = 6.6 Hz, 3 H). |
| 5 | | 504.4 | ¹HNMR (300 MHz, CD₃OD, ppm): δ 7.40 (d, J = 1.8 Hz, 1 H), 7.38-7.37 (m, 1 H), 7.19-6.94 (m, 2 H), 6.51 (d, J = 10.5 Hz, 2 H), 5.18 (s, 1 H), 4.55 (d, J = 5.4 Hz, 1 H), 4.39 (d, J = 5.4 Hz, 1 H), 4.00 (t, J = 6.3 Hz, 2 H), 3.70-3.58 (m, 1 H), 3.51 (t, J = 7.5 Hz, 2 H), 3.20 (t, J = 6.9. Hz, 2 H), 3.01-2.95 (m, 1 H), 2.90-2.84 (m, 4 H), 2.62-2.55 (m, 1 H), 2.45-2.37 (m, 1 H), 1.20-1.08 (m, 9 H). |
| 6 | | 486.4 | ¹HNMR (300 MHz, CD₃OD, ppm): δ 7.40 (d, J = 1.8 Hz, 1 H), 7.38-7.37 (m, 1 H), 7.18-6.94 (m, 2 H), 6.57 (d, J = 10.5 Hz, 2 H), 5.18 (s, 1 H), 4.12 (t, J = 5.4 Hz, 2 H), 3.70-3.58 (m, 1 H), 3.07-2.84 (m, 4 H), 2.70-2.55 (m, 5 H), 2.46-2.32 (m, 1 H), 1.84 (m, 4 H), 1.20-1.08 (m, 9 H). |

TABLE 1-continued

Exemplary Derivatives of Compound 1

| Example No. | Compound | [M + H]⁺ | HNMR |
|---|---|---|---|
| 7 | | 500.5 | ¹HNMR (300 MHz, CD₃OD, ppm): δ7.43-7.40 (m, 1 H), 7.21-7.18 (m, 1H), 7.06-6.95 (m, 2H), 6.60-6.54 (m, 2H), 5.21 (s, 1H), 4.12 (t, J = 5.4 Hz, 2 H), 3.70-3.58 (m, 1 H), 3.07-2.80 (m, 4 H), 2.76-2.57 (m, 5 H), 2.46-2.32 (m, 1 H), 1.65-1.62 (m, 4 H), 1.50-1.48 (m, 2 H), 1.20-1.08 (m, 9 H). |
| 8 | | 514.5 | ¹HNMR (300 MHz, CD₃OD, ppm): δ 7.42 (d, J = 6.9 Hz, 1 H), 7.20 (d, J = 7.8 Hz, 1 H), 7.04-6.95 (m, 2 H), 6.56 (d, J = 10.8 Hz, 2 H), 5.20 (s, 1H), 4.12 (t, J = 5.4 Hz, 2 H), 3.73-3.66 (m, 1 H), 3.09-2.90 (m, 1 H), 2.84-2.81 (m, 3H), 2.87-2.71 (m, 4 H), 2.61 (d, J = 14.7 Hz, 1H), 2.49-2.35 (m, 1 H), 1.69-1.64 (m, 8H), 1.23-1.11 (m, 9 H). |
| 9 | | 536.2 | ¹HNMR (300 MHz, CD₃OD, ppm) δ 7.39 (d, J = 6.9 Hz, 1H), 7.17 (d, J = 6.3 Hz, 1H), 7.05 (s, 1H), 7.05-6.93 (m, 2H), 6.85 (s, 1H), 5.61 (s, 1H), 4.54 (d, J = 5.7 Hz, 1H), 4.38 (d, J = 5.4 Hz, 1 H), 3.98 (t, J = 5.1 Hz, 2 H), 3.85-3.75 (m, 1H), 3.50 (t, J = 7.8 Hz, 2H), 3.21-3.13 (m, 3H), 2.97 (t, J = 14.4 Hz, 1H), 2.86-2.83 (m, 3H), 2.63 (d, J = 14.7 Hz, 1H), 2.37-2.22 (m, 1H), 1.21-1.06 (m, 9 H). |

TABLE 1-continued

Exemplary Derivatives of Compound 1

| Example No. | Compound | [M + H]+ | HNMR |
|---|---|---|---|
| 10 | 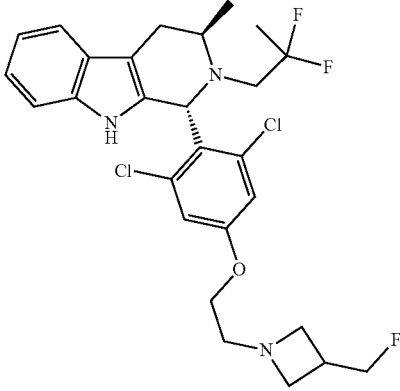 [SMILES: C[C@@H]1Cc2c([nH]c3ccccc23)[C@@H](c2c(Cl)cc(OCCN3CC(CF)C3)cc2Cl)N1CC(C)(F)F] | 540.4 | ¹HNMR (300 MHz, CDCl₃, ppm) δ 7.54-7.51 (m, 1 H), 7.26-7.20 (m, 2 H), 7.16-7.09 (m, 2 H), 6.97 (s, 1 H), 6.84 (s, 1 H), 5.66 (s, 1H), 4.62 (d, J = 7.2 Hz, 1 H), 4.46 (d, J = 7.2 Hz, 1 H), 4.02 (t, J = 4.5 Hz, 2 H), 3.78-3.69 (m, 1 H), 3.62 (s, 2 H), 3.28-3.05 (m, 4 H), 2.93 (s, 3H), 2.73-2.64 (m, 1H), 2.60-2.48 (m, 1H), 1.45 (t, J = 18.9 Hz, 3H), 1.16 (d, J = 6.3 Hz, 3H). |
| 11 | 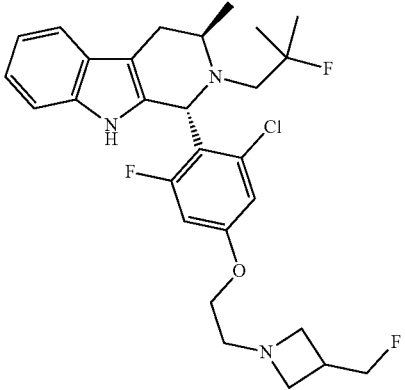 [SMILES: C[C@@H]1Cc2c([nH]c3ccccc23)[C@@H](c2c(F)cc(OCCN3CC(CF)C3)cc2Cl)N1CC(C)(C)F] | 520.2 | ¹HNMR (300 MHz, CD₃OD, ppm): δ 7.38 (dd, J₁ = 6.3 Hz, J₂ = 2.1 Hz, 1H), 7.16 (dd, J₁ = 6.3 Hz, J₂ = 2.1 Hz, 1 H), 6.98-6.93 (m, 2H) 6.83 (d, J = 2.1 Hz, 1 H), 6.64 (dd, J₁ = 12.0 Hz, J₂ = 2.1 Hz, 1 H), 5.35 (s, 1 H), 4.55 (d, J = 5.4 Hz, 1H), 4.39 (d, J = 5.4 Hz, 1 H), 3.99 (t, J = 5.4 Hz, 2 H), 3.80-3.72 (m, 1 H), 3.54-3.52 (m, 2 H), 3.20-3.10 (m, 3 H), 2.95-2.84 (m, 4 H), 2.60 (d, J = 14.4 Hz, 1 H), 2.40-2.25 (m, 1H), 1.14-1.06 (m, 9 H). |
| 12 | 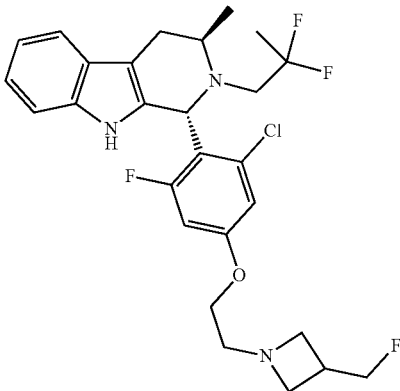 | 524.2 | ¹HNMR (300 MHz, CDCl₃, ppm): δ7.55-7.52 (m, 1 H), 7.45 (s, 1 H), 7.25-7.22 (m, 1 H), 7.16-7.09 (m, 2 H), 6.79 (t, J = 1.5 Hz, 1 H), 6.53 (dd, J = 3 Hz, J = 12 Hz, 1H), 5.41 (s, 1 H), 4.61 (d, J = 5.7 Hz, 1 H), 4.45(d, J = 5.7 Hz, 1 H), 3.95 (t, J = 5.4 Hz, 2 H), 3.74-3.67 (m, 1 H), 3.52(t, J = 7.5 Hz, 2 H), 3.18 (t, J = 6.9 Hz, 3 H), 3.12-3.04 (m, 1H), 2.85 (t, J = 5.4 Hz, 3 H), 2.70-2.53 (m, 2 H), 1.42 (t, J = 18.9 Hz, 3 H), 1.15(d, J = 6.6 Hz, 3 H). |

Example 2: Synthesis of Compounds 13B and Derivatives Thereof

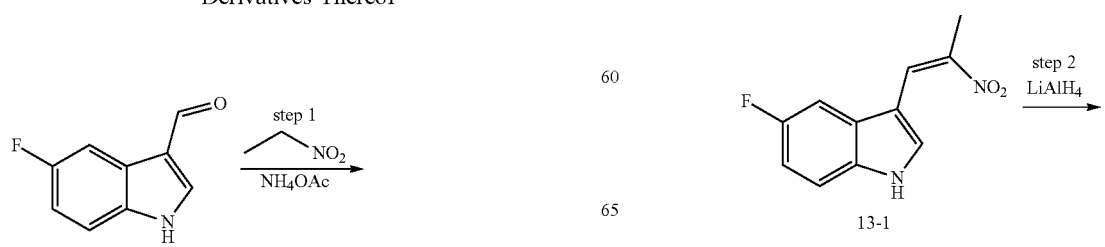

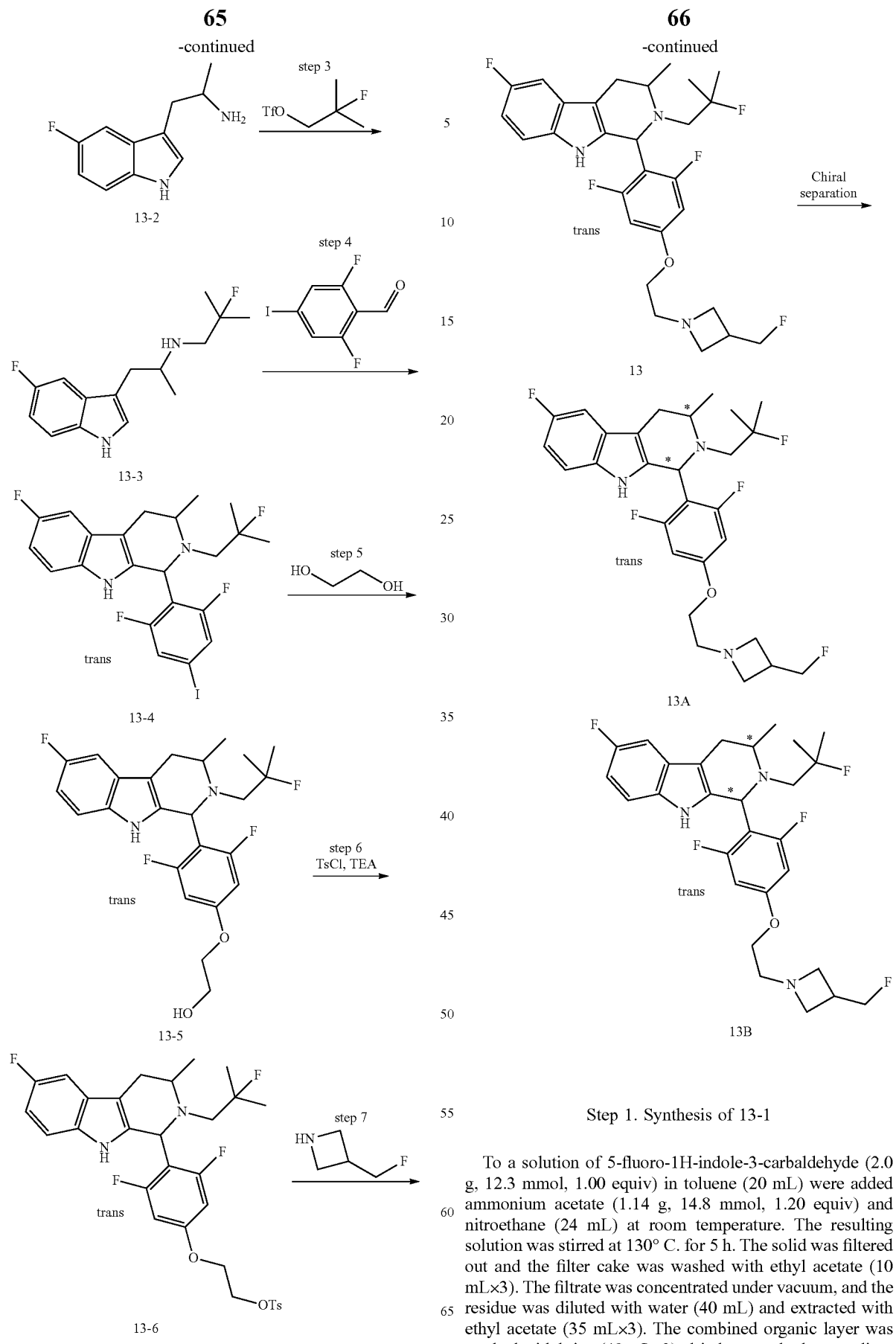

Step 1. Synthesis of 13-1

To a solution of 5-fluoro-1H-indole-3-carbaldehyde (2.0 g, 12.3 mmol, 1.00 equiv) in toluene (20 mL) were added ammonium acetate (1.14 g, 14.8 mmol, 1.20 equiv) and nitroethane (24 mL) at room temperature. The resulting solution was stirred at 130° C. for 5 h. The solid was filtered out and the filter cake was washed with ethyl acetate (10 mL×3). The filtrate was concentrated under vacuum, and the residue was diluted with water (40 mL) and extracted with ethyl acetate (35 mL×3). The combined organic layer was washed with brine (40 mL×3), dried over anhydrous sodium sulfate and concentrated under vacuum to afford 5-fluoro-3-[(1Z)-2-nitroprop-1-en-1-yl]-1H-indole (2.23 g, 83%) as a yellow solid.

Step 2. Synthesis of 13-2

To a solution of 5-fluoro-3-[(1Z)-2-nitroprop-1-en-1-yl]-1H-indole (2.0 g, 9.1 mmol, 1.00 equiv) in tetrahydrofuran (50 mL) was added lithium aluminum hydride (1.37 g, 36.0 mmol, 4.00 equiv) at 0° C. and the reaction mixture was stirred at 65° C. for 1 hour. After cooling to room temperature, the reaction was quenched by the addition of water (1.4 mL), sodium hydroxide aqueous solution (4.2 mL, 10%). The solid was filtered out, and the filter cake was washed with tetrahydrofuran (15 mL×3). The filtrate was concentrated under vacuum to afford 1-(5-fluoro-1H-indol-3-yl)propan-2-amine (1.8 g, 102%) as a brown oil.

Step 3. Synthesis of 13-3

To a solution of 1-(5-fluoro-1H-indol-3-yl)propan-2-amine (1.0 g, 5.2 mmol, 1.00 equiv) in 1,4-dioxane (24 mL) were added N,N-diisopropylethylamine (1.01 g, 7.8 mmol, 1.50 equiv) and 2-fluoro-2-methylpropyl trifluoromethanesulfonate (1.28 g, 5.7 mmol, 1.10 equiv). The resulting solution was stirred at 70° C. overnight. The reaction was quenched by the addition of water (30 mL) and the mixture was extracted with ethyl acetate (30 mL×3). The combined organic layer was washed with brine (30 mL×3), dried over anhydrous sodium sulfate and concentrated under vacuum. The residue was purified by silica gel column with ethyl acetate/petroleum ether (1:4) as eluent to afford [1-(5-fluoro-1H-indol-3-yl)propan-2-yl](2-fluoro-2-methylpropyl)amine (610 mg, 44%) as a brown solid.

Step 4. Synthesis of 13-4

To a solution of [1-(5-fluoro-1H-indol-3-yl)propan-2-yl](2-fluoro-2-methylpropyl)amine (510 mg, 1.92 mmol, 1.00 equiv) in toluene (20 mL) were added acetic acid (460 mg, 7.67 mmol, 4.00 equiv) and 2,6-difluoro-4-iodobenzaldehyde (514 mg, 1.92 mmol, 1.00 equiv). The resulting solution was stirred at 80° C. overnight. The reaction was quenched by the addition of water (15 mL) and the mixture was extracted with ethyl acetate (20 mL×3), the combined organic layer was washed with brine (20 mL×3), dried over anhydrous sodium sulfate and concentrated under vacuum. The residue was purified by silica gel column with ethyl acetate/petroleum ether (1:50) as eluent to afford 1-(2,6-difluoro-4-iodophenyl)-6-fluoro-2-(2-fluoro-2-methylpropyl)-3-methyl-1H,2H,3H,4H,9H-pyrido[3,4-b]indole (800 mg, 81%) as a light yellow solid.

Step 5. Synthesis of 13-5

To a solution of 1-(2,6-difluoro-4-iodophenyl)-6-fluoro-2-(2-fluoro-2-methylpropyl)-3-methyl-1H,2H,3H,4H,9H-pyrido[3,4-b]indole (680 mg, 1.32 mmol, 1.00 equiv) in ethylene glycol (20 mL) under $N_2$ protection were added cesium carbonate (859 mg, 2.64 mmol, 2.00 equiv) and cuprous iodide (126 mg, 0.66 mmol, 0.50 equiv) was added. The resulting solution was stirred overnight at 100° C. and the reaction was cooled to room temperature. Then the reaction was quenched by the addition of water (20 mL) and the mixture was extracted with ethyl acetate (30 mL×3). The combined organic layer was washed with brine (40 mL×3), dried over anhydrous sodium sulfate and concentrated under vacuum. The residue was applied onto a silica gel column with ethyl acetate/petroleum ether (1:1) as eluent to afford 2-[3,5-difluoro-4-[6-fluoro-2-(2-fluoro-2-methylpropyl)-3-methyl-1H,2H,3H,4H,9H-pyrido[3,4-b]indol-1-yl]phenoxy]ethan-1-ol (600 mg, 101%) as light yellow oil.

Step 6. Synthesis of 13-6

To a solution of 2-[3,5-difluoro-4-[6-fluoro-2-(2-fluoro-2-methylpropyl)-3-methyl-1H,2H,3H,4H,9H-pyrido[3,4-b]indol-1-yl]phenoxy]ethan-1-ol (550 mg, 1.22 mmol, 1.00 equiv) in dichloromethane (16 mL) were added triethylamine (247 mg, 2.44 mmol, 2.00 equiv) and N,N-dimethylaminopyridine (15 mg, 0.12 mmol, 0.10 equiv) under $N_2$. 4-methylbenzene-1-sulfonyl chloride (280 mg, 1.45 mmol, 1.20 equiv) was added at 0° C. The resulting solution was stirred at room temperature for 2 hours. The reaction was quenched by the addition of water (15 mL) and the mixture was extracted with dichloromethane (20 mL×3). The combined organic layer was washed with brine (30 mL×3), dried over anhydrous sodium sulfate and concentrated under vacuum. The residue was applied onto a silica gel column with ethyl acetate/petroleum ether (1:5) as eluent to afford 2-[3,5-difluoro-4-[6-fluoro-2-(2-fluoro-2-methylpropyl)-3-methyl-1H,2H,3H,4H,9H-pyrido[3,4-b]indol-1-yl]phenoxy]ethyl 4-methylbenzene-1-sulfonate (400 mg, 54%) as light yellow oil.

Step 7. Synthesis of 13

To a solution of 2-[3,5-difluoro-4-[6-fluoro-2-(2-fluoro-2-methylpropyl)-3-methyl-1H,2H,3H,4H,9H-pyrido[3,4-b]indol-1-yl]phenoxy]ethyl 4-methylbenzene-1-sulfonate (300 mg, 0.49 mmol, 1.00 equiv) in acetonitrile (18 mL) was added cesium carbonate (1.13 g, 3.48 mmol, 7.00 equiv) under $N_2$. 3-(fluoromethyl)azetidine trifluoroacetyl (462 mg, 2.48 mmol, 5.00 equiv) was then added at 0° C. The resulting solution was stirred at 80° C. overnight. The reaction mixture was cooled to room temperature and the reaction was quenched by the addition of water (20 mL), the mixture was extracted with ethyl acetate (20 mL×3). The combined organic layer was washed with brine (30 mL×3), dried over anhydrous sodium sulfate and concentrated under vacuum. The crude product was purified by prep-HPLC [Column, Xbridge, RP18, 19*150 mm; mobile phase, A: $NH_4CO_3$ (aq) (5 mmol/L), B: acetonitrile (70%-90% in 8 min); rate, 25 mL/min; Detector, 254 nm] to afford compound 111 (100 mg, 38%) as a white solid. Compound 111 was resolved by chiral preparative HPLC [Chiral Column, IA-3, 250 mm×20 mm, 5 um; mobile phase, A: hexane (91%), B: ethanol (9%); rate, 20 mL/min; Detector, 254 nm] to afford 13A (retention time: 13.91 min) and 13B (retention time: 22.37 min).

13A 13.9 mg, white solid. Chiral HPLC [Column: IA, 100 mm, 4.6 mm, 0.6 mL/min, Mobile Phase: hexane (0.1% DEA)/IPA; Gradient: 10% IPA; Detector: 254 nm], Retention time=7.22 min. LCMS (ES, m/z) [M+H]+: 522.40. $^1$HNMR (300 MHz, $CD_3OD$, ppm) δ 7.13 (dd, J=4.5 Hz, J=8.7 Hz, 1H), 7.07 (dd, J=2.4 Hz, 6.9 Hz, 1H), 6.76 (td, J=2.4 Hz, 9.0 Hz, 1H), 6.58-6.53 (m, 2H), 5.19 (s, 1H), 4.58 (d, J=7.2 Hz, 1H), 4.42 (d, J=7.2 Hz, 1H), 4.01 (t, J=6.8 Hz, 2H), 3.71-3.65 (m, 1H), 3.55 (t, J=10.0 Hz, 2H), 3.24 (t, J=10.0

Hz, 2H), 3.06-2.99 (m, 1H), 2.91-2.86 (m, 3H), 2.57 (dd, J=2.7 Hz, J=14.7 Hz, 1H), 2.40 (dd, J=15.0 Hz, J=26.4 Hz, 1H), 1.23-1.10 (n, 9H).

13B 17.8 mg, white solid. Chiral HPLC [Column: IA, 100 mm, 4.6 mm, 0.6 mL/min, Mobile Phase: hexane (0.1% DEA)/IPA; Gradient: 10% IPA; Detector: 254 nm], Retention time=12.34 min. LCMS (ES, m/z) [M+H]+: 522.40. $^1$HNMR (300 MHz, CD$_3$OD, ppm) δ 7.13 (dd, J=4.2 Hz, J=8.7 Hz, 1H), 7.07 (dd, J=2.4 Hz, 6.9 Hz, 1H), 6.77 (td, J=2.4 Hz, 9.0 Hz, 1H), 6.58-6.53 (m, 2H), 5.19 (s, 1H), 4.58 (d, J=5.4 Hz, 1H), 4.42 (d, J=5.7 Hz, 1H), 4.01 (t, J=5.7 Hz, 2H), 3.71-3.65 (m, 1H), 3.56 (t, J=7.8 Hz, 2H), 3.24 (t, J=7.8 Hz, 2H), 3.06-2.99 (m, 1H), 2.91-2.86 (m, 3H), 2.57 (dd, J=2.7 Hz, J=14.7 Hz, 1H), 2.40 (dd, J=15.0 Hz, J=26.4 Hz, 1H), 1.23-1.10 (n, 9H).

Using the similar procedures described above, the following additional compounds of the invention were prepared.

TABLE 2

Exemplary Derivatives of Compound 13B

| Example No. | Compound | [M + H]+ | HNMR |
|---|---|---|---|
| 14A | (structure, trans) | 553.2 | Chiral HPLC [Column: AD, 100 mm, 4.6 mm, 0.6 mL/min, Mobile Phase: hexane (0.1% TFA)/IPA; Gradient: 30% IPA; Detector: 254 nm], Retention time = 2.70 min. $^1$HNMR (300 MHz, DMSO-d$_6$, ppm): δ10.39 (s, 1 H), 7.14-7.10 (m, 3 H), 6.90 (d, J = 2.4 Hz, 1 H), 6.83-6.76 (m, 1 H), 5.47 (s, 1 H), 4.58 (d, J = 6.3 Hz, 1 H), 4.42 (d, J = 6.0 Hz, 1 H), 4.08-3.95 (m, 2 H), 3.72-3.68 (m, 1 H), 3.35-3.26 (m, 4 H), 3.04-2.91 (m, 3 H), 2.76-2.56 (m, 3 H), 2.29-2.14 (m, 1 H), 1.16-1.09 (m, 9 H). |
| 14B | (structure, trans) | 553.2 | Chiral HPLC [Column: AD, 100 mm, 4.6 mm, 0.6 mL/min, Mobile Phase: hexane (0.1% TFA)/IPA; Gradient: 30% IPA; Detector: 254 nm], Retention time = 3.12 min. $^1$HNMR (300 MHz, DMSO-d$_6$, ppm): δ10.40 (s, 1 H), 7.15-7.10 (m, 3 H), 6.90 (d, J = 2.4 Hz, 1 H), 6.83-6.76 (m, 1 H), 5.47 (s, 1 H), 4.58 (d, J = 6.6 Hz, 1 H), 4.42 (d, J = 6.0 Hz, 1 H), 4.05-3.93 (m, 2 H), 3.72-3.65(m, 1 H), 3.04 (s, 1 H), 3.35-3.26 (m, 4 H), 3.09-2.86 (m, 3 H), 2.73-2.56 (m, 3 H), 2.29-2.14 (m, 1 H), 1.16-1.04 (m, 9 H). |
| 15A | (structure, trans) | 534.3 | Chiral HPLC [Column: IA, 100 mm, 4.6 mm, 0.6 mL/min, Mobile Phase: hexane (0.1% TFA)/ethanol; Gradient: 30% EtOH; Detector: 254 nm], Retention time = 3.53 min. $^1$HNMR (300 MHz, CDCl3, ppm) δ 7.38 (d, J = 9.3 Hz, 1H), 6.78-6.74 (m, 2H), 6.39 (d, J = 10.2 Hz, 2H), 5.15 (s, 1 H), 4.65-4.38 (m, 2H), 4.12-3.96 (m, 2H), 3.81 (s, 3H), 3.73-3.18 (m, 4H), 3.17-2.70 (m, 6 H), 2.63-2.23 (m, 2H), 1.28-1.04 (m, 9H). |

TABLE 2-continued
Exemplary Derivatives of Compound 13B
| Example No. | Compound | [M + H]⁺ | HNMR |
|---|---|---|---|
| 15B | 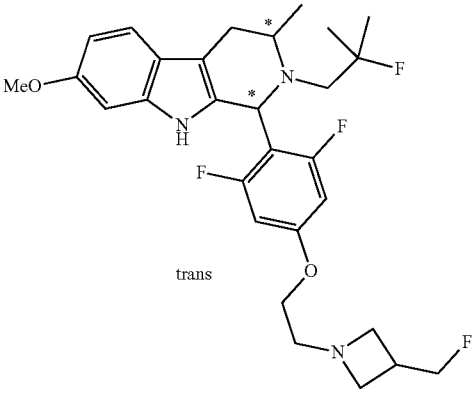 [SMILES: COc1ccc2c3c([nH]c2c1)C(c1c(F)cc(OCCN2CC(CF)C2)cc1F)N(CC(C)(C)F)C(C)C3] trans | 534.3 | Chiral HPLC [Column: IA, 100 mm, 4.6 mm, 0.6 mL/min, Mobile Phase: hexane (0.1% TFA)/ethanol; Gradient: 30% EtOH; Detector: 254 nm], Retention time = 4.77 min. ¹HNMR: (300 MHz, CDCl3, ppm): δ 7.38 (d, J = 9.3 Hz, 1H), 6.81-6.72 (m, 2H), 6.39 (d, J = 10.5 Hz, 2H), 5.15 (s, 1 H), 4.67-4.39 (m, 2H), 4.25-3.95 (m, 2H), 3.81 (s, 3H), 3.73-3.22 (m, 4 H), 3.19-2.74 (m, 6 H), 2.59-2.30 (m, 2H), 1.31-1.06 (m, 9H). |
Example 3: Synthesis of Compound 16B
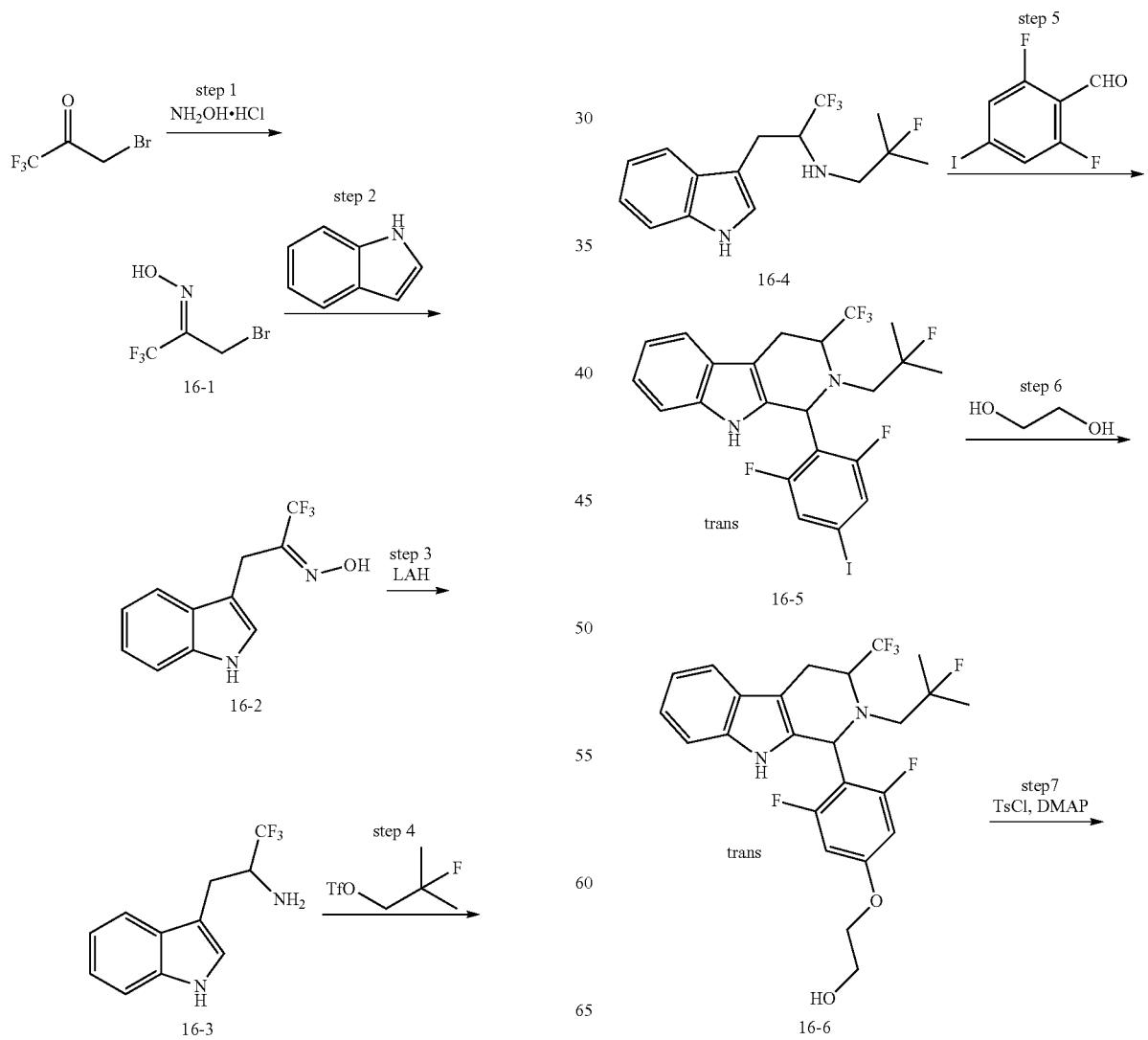

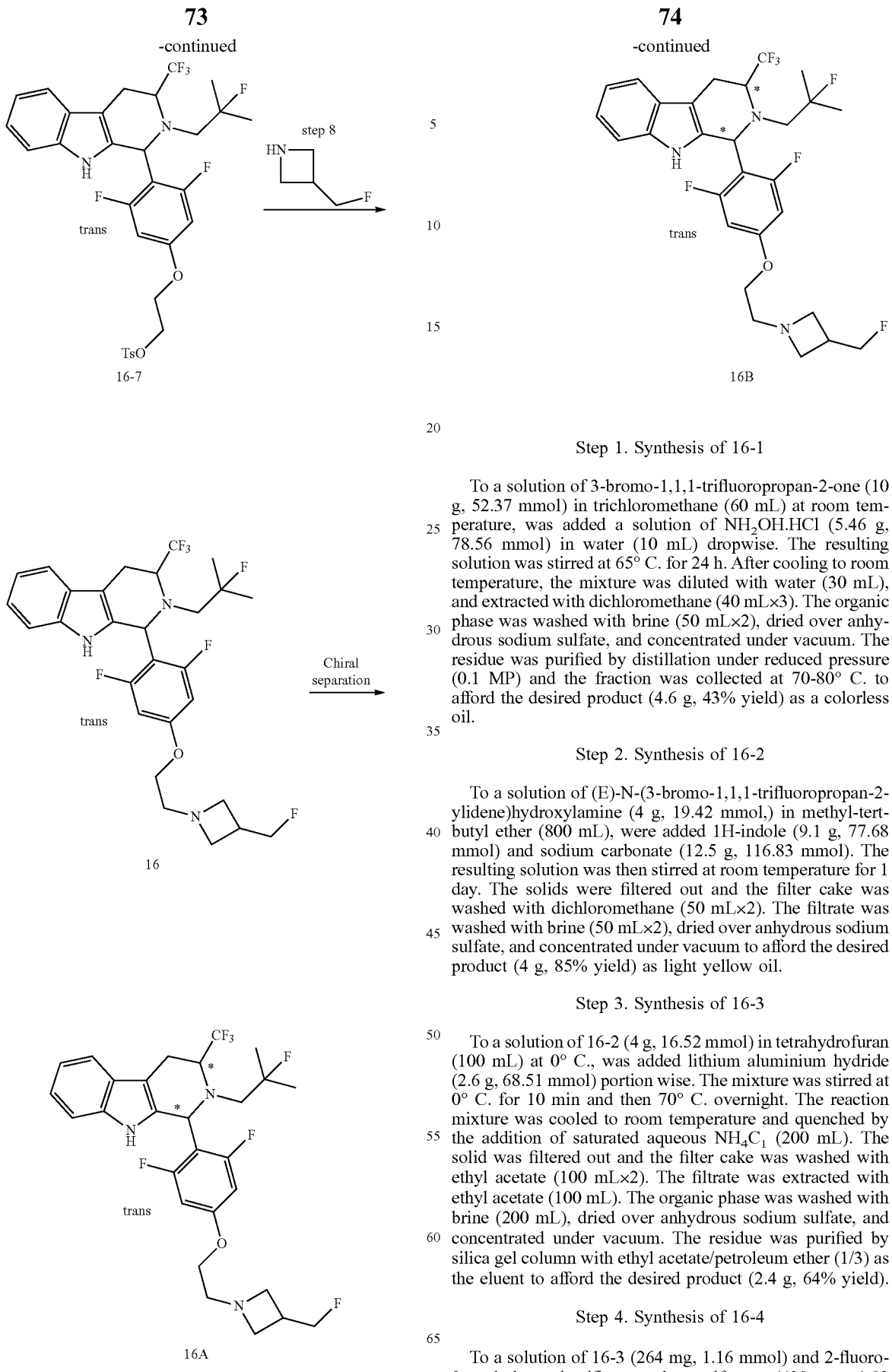

Step 1. Synthesis of 16-1

To a solution of 3-bromo-1,1,1-trifluoropropan-2-one (10 g, 52.37 mmol) in trichloromethane (60 mL) at room temperature, was added a solution of $NH_2OH \cdot HCl$ (5.46 g, 78.56 mmol) in water (10 mL) dropwise. The resulting solution was stirred at 65° C. for 24 h. After cooling to room temperature, the mixture was diluted with water (30 mL), and extracted with dichloromethane (40 mL×3). The organic phase was washed with brine (50 mL×2), dried over anhydrous sodium sulfate, and concentrated under vacuum. The residue was purified by distillation under reduced pressure (0.1 MP) and the fraction was collected at 70-80° C. to afford the desired product (4.6 g, 43% yield) as a colorless oil.

Step 2. Synthesis of 16-2

To a solution of (E)-N-(3-bromo-1,1,1-trifluoropropan-2-ylidene)hydroxylamine (4 g, 19.42 mmol,) in methyl-tert-butyl ether (800 mL), were added 1H-indole (9.1 g, 77.68 mmol) and sodium carbonate (12.5 g, 116.83 mmol). The resulting solution was then stirred at room temperature for 1 day. The solids were filtered out and the filter cake was washed with dichloromethane (50 mL×2). The filtrate was washed with brine (50 mL×2), dried over anhydrous sodium sulfate, and concentrated under vacuum to afford the desired product (4 g, 85% yield) as light yellow oil.

Step 3. Synthesis of 16-3

To a solution of 16-2 (4 g, 16.52 mmol) in tetrahydrofuran (100 mL) at 0° C., was added lithium aluminium hydride (2.6 g, 68.51 mmol) portion wise. The mixture was stirred at 0° C. for 10 min and then 70° C. overnight. The reaction mixture was cooled to room temperature and quenched by the addition of saturated aqueous $NH_4C_1$ (200 mL). The solid was filtered out and the filter cake was washed with ethyl acetate (100 mL×2). The filtrate was extracted with ethyl acetate (100 mL). The organic phase was washed with brine (200 mL), dried over anhydrous sodium sulfate, and concentrated under vacuum. The residue was purified by silica gel column with ethyl acetate/petroleum ether (1/3) as the eluent to afford the desired product (2.4 g, 64% yield).

Step 4. Synthesis of 16-4

To a solution of 16-3 (264 mg, 1.16 mmol) and 2-fluoro-2-methylpropyl trifluoromethanesulfonate (430 mg, 1.92 mmol) in 1,4-dioxane (1 mL), were added 18-crown-6 (422 mg, 1.60 mmol) and N,N-diisopropylethylamine (620 mg, 4.80 mmol). The resulting solution was then stirred at 110° C. for 26 h. After cooling to room temperature, the reaction was concentrated under vacuum. The residue was dissolved in dichloromethane (50 mL), and washed with brine (30 mL×2). The organic phase was dried over anhydrous sodium sulfate and concentrated under vacuum. The residue was purified by Flash-Prep-HPLC with the following conditions [Column: C18 silica gel; Mobile phase: MeCN/$H_2O$ (0.1% TFA)), 25%-70% MeCN; Detector: 254 nm] to afford the desired product (270 mg).

Step 5. Synthesis of 16-5

To a solution of 16-4 (600 mg, 1.98 mmol) in toluene (6 mL), were added 2,6-difluoro-4-iodobenzaldehyde (590 mg, 2.20 mmol) and acetic acid (0.2 mL). The reaction mixture was then stirred at 80° C. for 16 h. After cooled down, the mixture was concentrated under vacuum. The residue was purified by silica gel column with ethyl acetate/petroleum ether (1/29) as the eluent to afford the desired product (600 mg, 55% yield).

Step 6. Synthesis of 16-6

To a solution of 16-5 (600 mg, 1.09 mmol) in ethane-1,2-diol (12 mL), were added 1,10-phenanthroline (20 mg, 0.11 mmol), CuI (105 mg, 0.55 mmol), and cesium carbonate (711 mg, 2.18 mmol). The reaction mixture was stirred at 100° C. for 2 h. After cooled down, the mixture was diluted with water (100 mL), and extracted with ethyl acetate (100 mL×2). The organic phase was washed with brine (100 mL×2), dried over anhydrous sodium sulfate, and concentrated under vacuum. The residue was purified by silica gel column with ethyl acetate/petroleum ether (1:2) as the eluent to afford the desired product (270 mg, 51% yield).

Step 7. Synthesis of 16-7

To a solution of 16-6 (270 mg, 0.56 mmol) in tetrahydrofuran (10 mL), were added p-toluenesulfonyl chloride (128 mg, 0.67 mmol), 4-dimethylaminopyridine (13 mg, 0.11 mmol), and triethylamine (68 mg, 0.67 mmol). The reaction mixture was stirred at 30° C. for 16 h before concentrated under vacuum. The residue was purified by silica gel column with ethyl acetate/petroleum ether (2:1) as the eluent to afford the desired product (120 mg, 34% yield).

Step 8. Synthesis of 16

To a solution of 3-(fluoromethyl)azetidine (261 mg, 1.39 mmol) in acetonitrile (10 mL), were added cesium carbonate (1.02 g, 3.13 mmol) and 16-7 (100 mg, 0.16 mmol). The reaction mixture was stirred at 80° C. for 16 h. After cooled down, the solids were filtered out and the filtrate was concentrated under vacuum. The residue was purified by Flash-Prep-HPLC [Column, C18 silica gel; Mobile phase (A: $H_2O$ (0.05% $NH_4HCO_3$), B:MeCN), 40% MeCN to 69% MeCN in 10 min; rate: 80 mL/min; Detector, UV 254 nm]. The crude product was then purified by Prep-HPLC [Column, Xbridge RP C18, 19×150 nm; Mobile phase (A: $H_2O$ (0.05% $NH_4HCO_3$), B: MeCN), MeCN=50% to MeCN=80% in 8 min, rate: 25 mL/min; Detector, UV 254 nm] to afford the desired product as racemate (25 mg, 29% yield).

The racemic product 16 was resolved by Chiral-Prep-HPLC [Column, IA; Mobile phase, 12% ethanol/hexane (0.1% diethylamine); 20 mL/min; 18 min; Detector, 254 nm] to afford the desired products.

Compound 16A: Retention time=7.7 min. LCMS (ES, m/z): 558.20 [M+H]+; $^1$HNMR (300 MHz, $CD_3OD$, ppm): δ 7.45 (d, J=6.9 Hz, 1H), 7.19 (d, J=6.9 Hz, 1H), 7.06-6.96 (m, 2H), 6.56 (d, J=11.1 Hz, 2H), 5.52 (s, 1H), 4.55 (d, J=5.4 Hz, 1H), 4.39 (d, J=5.4 Hz, 1H), 4.28-4.16 (m, 1H), 4.01-3.98 (m, 2H), 3.63-3.47 (m, 2H), 3.37-3.22 (m, 4H), 3.19-3.02 (m, 2H), 2.91-2.59 (m, 3H), 1.28-1.09 (m, 6H).

Compound 16B: Retention time=14.5 min. LCMS (ES, m/z): 558.20 [M+H]+; $^1$H-NMR (300 MHz, $CD_3OD$, ppm): δ 7.44 (d, J=6.9 Hz, 1H), 7.20 (d, J=7.2 Hz, 1H), 7.05-6.96 (m, 2H), 6.56 (d, J=13.8 Hz, 2H), 5.52 (s, 1H), 4.55 (d, J=5.4 Hz, 1H), 4.40 (d, J=5.4 Hz, 1H), 4.28-4.02 (m, 1H), 4.01-3.98 (m, 2H), 3.58-3.53 (m, 2H), 3.34-3.25 (m, 4H), 3.13-3.10 (m, 2H), 2.92-2.88 (m, 2H), 2.73-2.59 (m, 1H), 1.28-1.09 (m, 6H).

Example 4: Synthesis of Compounds 17A and 17B and Derivatives Thereof

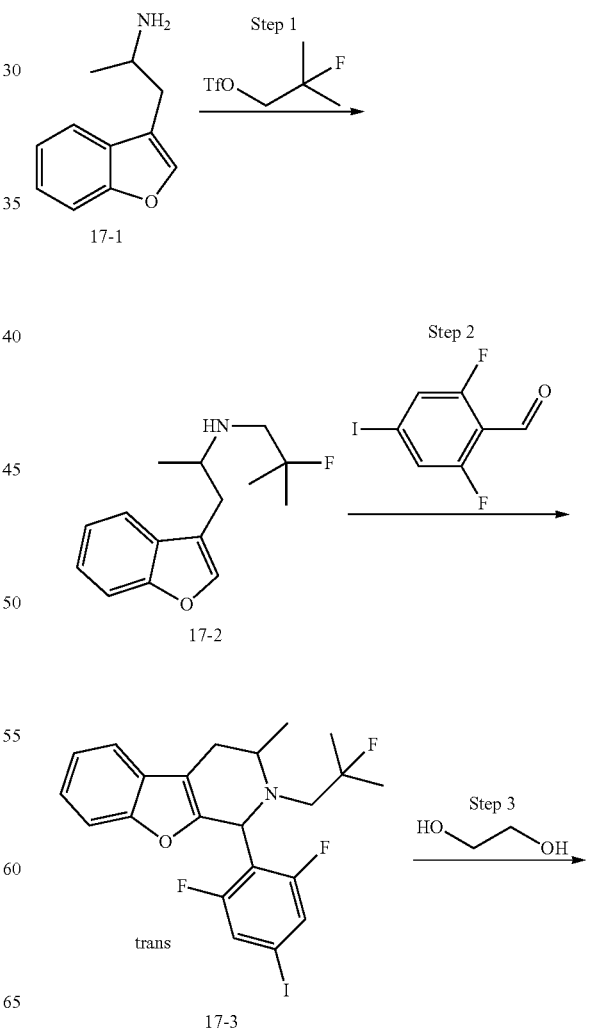

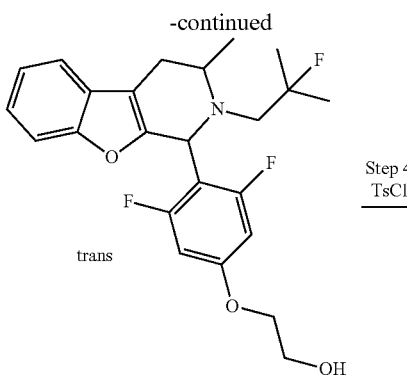

17-4

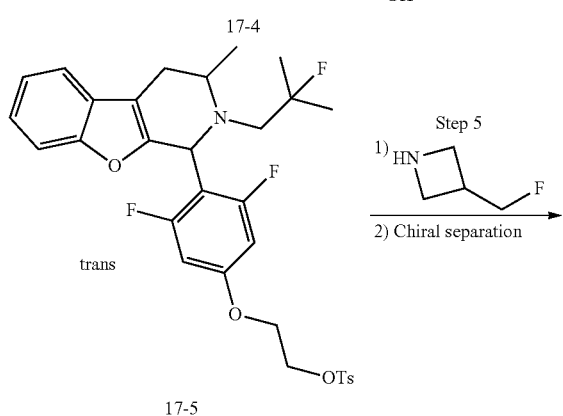

17-5

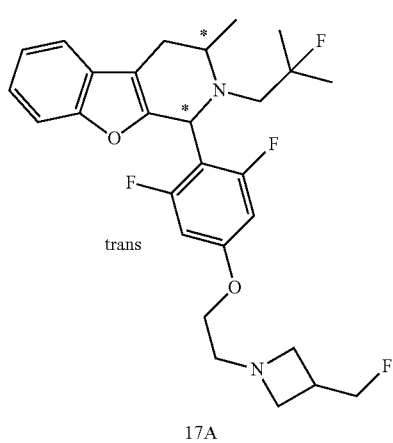

17A

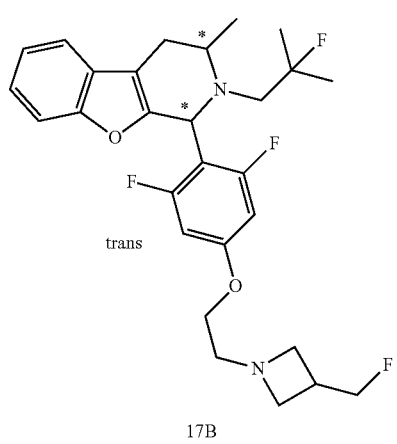

17B

Step 1. Synthesis of 17-2

To a solution of 1-(1-benzofuran-3-yl)propan-2-amine (1.2 g, 6.85 mmol) in 1,4-Dioxane (40 mL), were added N,N-diisopropylethylamine (2.6 g, 20.12 mmol) and 2-fluoro-2-methylpropyl trifluoromethanesulfonate (1.54 g, 6.87 mmol). The resulting solution was stirred at 75° C. for 16 h. After cooled down, the mixture was diluted with icy water (100 mL), and extracted with ethyl acetate (100 mL×3). The organic phase was washed with brine (100 mL×2), dried over anhydrous sodium sulfate, and concentrated under vacuum to afford the desired product (1.5 g, 88% yield).

Step 2. Synthesis of 17-3

To a mixture of 17-2 (820 mg, 3.29 mmol) in toluene (30 mL), were added acetic acid (593 mg, 9.88 mmol) and 2,6-difluoro-4-iodobenzaldehyde (883 mg, 3.29 mmol). The resulting solution was stirred at 100° C. for 2 days. After cooled down, the mixture was diluted with icy water (100 mL), and extracted with ethyl acetate (50 mL×3). The organic phase was washed with brine (50 mL×2), dried over anhydrous sodium sulfate, and concentrated under vacuum to afford the desired product (0.3 g, 18% yield).

Step 3. Synthesis of 17-4

To a mixture of 17-3 (300 mg, 0.60 mmol) in ethane-1, 2-diol (10 mL), were added cesium carbonate (585 mg, 1.80 mmol) and copper(I) iodide (114.2 mg). The resulting solution was stirred at 100° C. overnight. After cooled down, the mixture was diluted with saturated ammonium chloride solution (30 mL), and extracted with ethyl acetate (30 mL×3). The organic phase was washed with brine (30 mL×2), dried over anhydrous sodium sulfate, and concentrated under vacuum to afford the desired product (150 mg, 58% yield).

Step 4. Synthesis of 17-5

To a solution of 17-4 (150 mg, 0.35 mmol) in dichloromethane (10 mL), were added triethylamine (35 mg, 0.35 mmol), 4-methylbenzene-1-sulfonyl chloride (79 mg, 0.41 mmol) and 4-dimethylaminopyridine (5 mg, 0.04 mmol). The resulting solution was stirred at room temperature overnight. The reaction was then quenched by water (30 mL). The resulting solution was extracted with dichloromethane (20 mL×3). The organic phase was washed with brine (20 mL×2), dried over anhydrous sodium sulfate, and concentrated under vacuum. The residue was purified by silica gel column with ethyl acetate/petroleum ether (1:3) as the eluent to afford the desired product (0.17 g, 84% yield).

Step 5. Synthesis of 17A and 17B

To a solution of 17-5 (170 mg, 0.29 mmol) in acetonitrile (10 mL) were added 3-(fluoromethyl)azetidine (103 mg, 1.16 mmol) and cesium carbonate (376 mg, 1.14 mmol). The resulting solution was stirred at 80° C. overnight. After cooled down, the mixture was diluted with icy water (30 mL), and extracted with ethyl acetate (30 mL×3). The organic phase was washed with brine (20 mL×2), dried over anhydrous sodium sulfate, and concentrated under vacuum. The residue was purified by Prep-HPLC [Column: C18; Mobile Phase: $CH_3CN/H_2O$ (0.05% $NH_4HCO_3$); Gradient:

70%-86% MeCN, 8 min; Detected: 254 nm] to afford the racemate 17 (30 mg, 21% yield) as a white solid.

The racemate of 17 was resolved by Prep-Chiral-HPLC [Column: AD-H; Mobile Phase: Hex/EtOH; Gradient: 13% EtOH, 18 min; Rate: 20 mL/min; Detector: 254 nm] to afford the desired products.

Compound 17A: Chiral HPLC [Column: AD, 100 mm, 4.6 mm, 0.6 mL/min, Mobile Phase: hexane (0.1% TFA)/ethanol; Gradient: 15% EtOH; Detector: 254 nm], Retention time=3.03 min. LC-MS (ES, m/z): 505.4 [M+H]+; $^1$HNMR (300 MHz, CD$_3$OD, ppm): δ 7.49-7.46 (m, 1H), 7.32-7.29 (m, 1H), 7.21-7.18 (m, 2H) 6.54 (d, J=10.8 Hz, 2H), 5.14 (s, 1H), 4.55 (d, J=5.7 Hz, 1H), 4.40 (d, J=5.4 Hz, 1H), 4.01-3.98 (m, 2H), 3.90 (d, J=5.4 Hz, 1H), 3.69-3.51 (m, 2H), 3.32-3.19 (m, 2H), 2.97-2.86 (m, 5H), 2.86-2.57 (m, 1H), 2.53-2.38 (m, 1H), 1.28-1.10 (min, 9H).

Compound 17B: Chiral HPLC [Column: AD, 100 mm, 4.6 mm, 0.6 mL/min, Mobile Phase: hexane (0.1% TFA)/ethanol; Gradient: 15% EtOH; Detector: 254 nm], Retention time=5.20 min. LC-MS (ES, m/z): 505.4 [M+H]+; $^1$HNMR (300 MHz, CD$_3$OD, ppm): δ 7.47 (s, 1H), 7.30-7.19 (m, 3H), 6.54 (d, J=11.1 Hz, 2H), 5.14 (s, 1H), 4.55 (d, J=5.1 Hz, 1H), 4.40 (d, J=4.8 Hz, 1H), 4.06 (s, 2H), 3.68 (s, 1H), 3.56-3.51 (m, 2H), 3.31-3.20 (m, 2H), 3.07-2.88 (m, 5H), 2.67-2.33 (m, 2H), 1.63-1.40 (min, 9H).

Using the similar procedures described above, the following additional compounds of the invention were prepared.

TABLE 3

Exemplary Derivatives of Compound 17A and Compound 17B

| Example No. | Compound | [M + H]+ | HNMR |
|---|---|---|---|
| 18 | 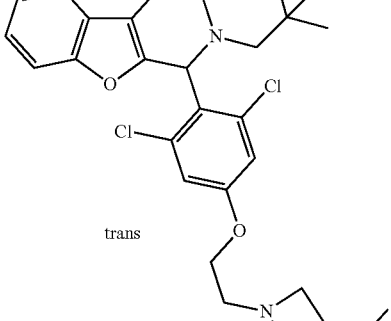 trans | 537.5 | $^1$H-NMR (300 MHz, CD$_3$OD, ppm) δ 7.47-7.44 (m, 1 H), 7.30-7.27 (m, 1 H), 7.19-7.17 (m, 2 H), 7.07 (s, 1H), 6.89 (s, 1 H), 5.59 (s, 1 H), 4.57 (d, J = 5.4 Hz, 1 H), 4.4 (d, J = 5.4 Hz, 1 H)), 4.03-4.00 (m, 2 H), 3.87-3.84 (m, 1 H), 3.56-3.51 (m, 2 H), 3.30-3.20 (m, 2 H), 3.11-3.07 (m, 1 H), 3.04-2.90(m, 1 H), 2.88-2.78 (m, 3 H), 2.59 (d, J = 15.3 Hz, 1 H), 2.36-2.22 (m, 1 H), 1.37-0.90 (m, 9 H). |
| 19A | 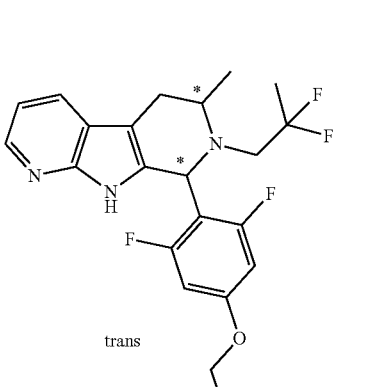 trans | 509.4 | Chiral HPLC [Column: AD, 100 mm, 4.6 mm, 0.6 mL/min, Mobile Phase: hexane (0.1% TFA)/IPA; Gradient: 70% IPA; Detector: 254 nm], Retention time = 12.27 min.<br>$^1$HNMR (300 MHz, CDCl3, ppm) δ 8.79 (s, 1H), 8.12 (d, J = 1.5 Hz, 1H), 7.81 (d, J = 7.5, 1H), 7.07-7.03 (m, 1H), 6.44 (d, J = 10.5 Hz, 2H), 5.25 (s, 1H), 4.60 (s, 1H), 4.44 (s, 1H), 4.26-3.90 (m, 4H), 3.68-3.58 (m, 3H), 3.24 (s, 2H), 3.09-3.00 (m, 2H), 2.67-2.57 (m, 2H), 1.45 (t, J = 18.6 Hz, 3H), 1.14 (d, J = 6.3 Hz, 3H). |

TABLE 3-continued

Exemplary Derivatives of Compound 17A and Compound 17B

| Example No. | Compound | [M + H]+ | HNMR |
|---|---|---|---|
| 19B | 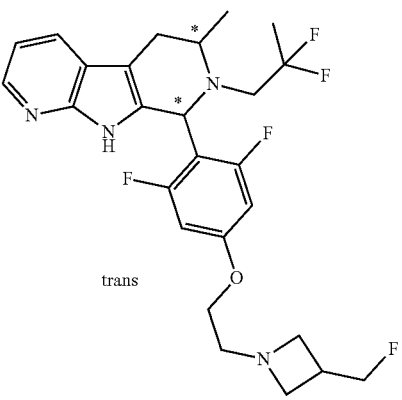 [SMILES: CC1Cc2c([nH]c3ncccc23)C(c2c(F)cc(OCCN3CC(CF)C3)cc2F)N1CC(C)(F)F]<br>trans | 509.4 | Chiral HPLC [Column: AD, 100 mm, 4.6 mm, 0.6 mL/min, Mobile Phase: hexane (0.1% TFA)/IPA; Gradient: 70% IPA; Detector: 254 nm], Retention time = 16.92 min.<br>$^1$HNMR (300 MHz, CDCl3, ppm) δ 8.86 (s, 1H), 8.12 (d, J = 1.5 Hz, 1H), 7.80 (d, J = 7.5 Hz, 1H), 7.06-7.02 (m, 1H), 6.43 (d, J = 10.5 Hz, 2H), 5.24 (s, 1H), 4.60 (s, 1H), 4.43 (d, J = 3.9 Hz, 1H), 4.26-3.95 (m, 4H), 3.63-3.59 (m, 3H), 3.24-3.00 (m, 4H), 2.72-2.17 (m, 2H), 1.44 (t, J = 18.6 Hz, 3H), 1.14 (d, J = 6.3 Hz, 3H). |

Example 5: Synthesis of Compound 20

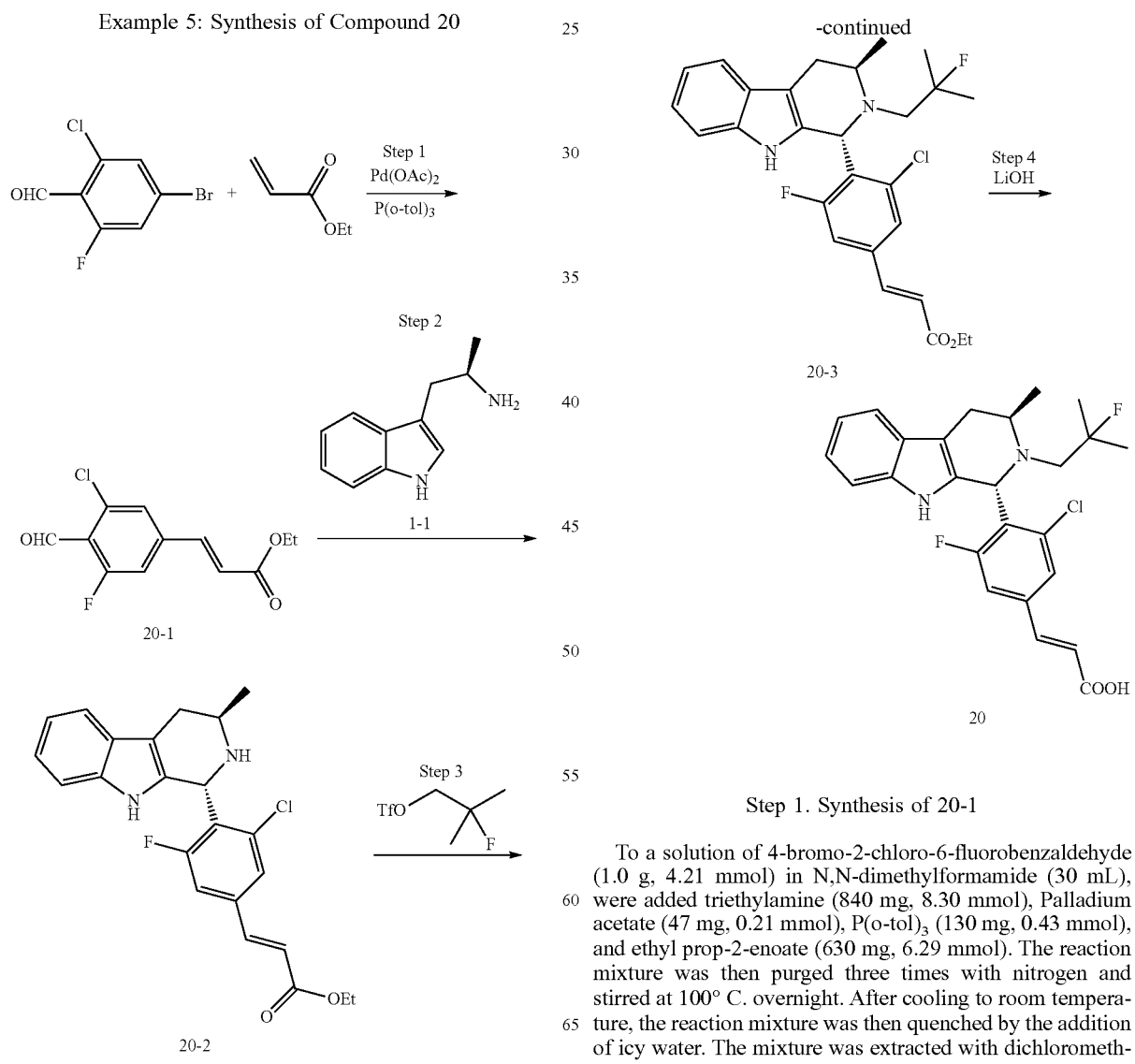

Step 1. Synthesis of 20-1

To a solution of 4-bromo-2-chloro-6-fluorobenzaldehyde (1.0 g, 4.21 mmol) in N,N-dimethylformamide (30 mL), were added triethylamine (840 mg, 8.30 mmol), Palladium acetate (47 mg, 0.21 mmol), P(o-tol)$_3$ (130 mg, 0.43 mmol), and ethyl prop-2-enoate (630 mg, 6.29 mmol). The reaction mixture was then purged three times with nitrogen and stirred at 100° C. overnight. After cooling to room temperature, the reaction mixture was then quenched by the addition of icy water. The mixture was extracted with dichloromethane (50 mL×3). The organic phase was washed with brine (30 mL×2), dried over anhydrous sodium sulfate, and concentrated under vacuum. The residue was purified by silica gel column with ethyl acetate/petroleum ether (1/5) as the eluent to afford the desired product (0.8 g, 74% yield).

Step 2. Synthesis of 20-2

To a solution of (2R)-1-(1H-indol-3-yl)propan-2-amine (340 mg, 1.95 mmol) in toluene (10 mL), were added ethyl (2E)-3-(3-chloro-5-fluoro-4-formylphenyl)prop-2-enoate (600 mg, 2.34 mmol) and acetic acid (230 mg, 3.83 mmol). The reaction mixture was stirred at 80° C. overnight, then cooled to room temperature, and concentrated under vacuum. The residue was purified by silica gel column with ethyl acetate/petroleum ether (2/5) to afford the desired product (0.7 g, 87% yield).

Step 3. Synthesis of 20-3

To a solution of ethyl 20-2 (700 mg, 1.70 mmol) in 1,4-dioxane (20 mL), were added N,N-diisopropylethylamine (1.09 g, 8.43 mmol) and 2-fluoro-2-methylpropyl trifluoromethanesulfonate (1.14 g, 5.09 mmol). The reaction mixture was stirred at 120° C. overnight, then cooled to room temperature, and concentrated under vacuum. The residue was purified by Prep-HPLC [Column: SunFire Prep C18, 5 um, 19*150 mm; Mobile Phase: MeCN/Water (0.1% FA); Gradient: 71%-86% MeCN, 6 min, 25 mL/min; Detector: 220 nm] to afford the desired product (0.25 g, 30% yield).

Step 4. Synthesis of 20

To a solution of ethyl 20-3 (250 mg, 0.51 mmol) in tetrahydrofuran (30 mL) and water (3 mL), was added lithium hydroxide (25 mg, 1.04 mmol). The reaction mixture was stirred at room temperature overnight, and then concentrated under vacuum. The pH of the residue was adjusted to 5-6 with hydrogen chloride (1 N). The reaction was extracted with dichloromethane (30 mL×3). The organic phase was dried over anhydrous sodium sulfate, and concentrated under vacuum. The residue was dissolved in MeCN/H$_2$O and dried by lyphilization to afford the desired product (75.4 mg, 32% yield). LCMS (ES, m/z): 459.16 [M+H]+; $^1$HNMR: (300 MHz, DMSO-d$_6$, ppm): δ 12.55 (br s, 1H), 10.44 (s, 1H), 7.70 (s, 1H), 7.59-7.52 (m, 2H), 7.41 (d, J=7.2 Hz, 1H), 7.17 (d, J=6.9 Hz, 1H), 7.01-6.92 (m, 2H), 6.69 (d, J=15.9 Hz, 1H), 5.35 (s, 1H), 3.68-3.61 (m, 1H), 3.08-2.90 (m, 2H), 2.64-2.59 (m, 1H), 2.50-2.20 (m, 1H), 1.16-1.05 (m, 9H).

Example 6: Synthesis of Compound 21

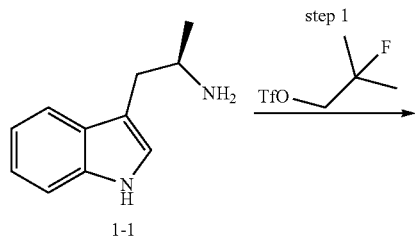

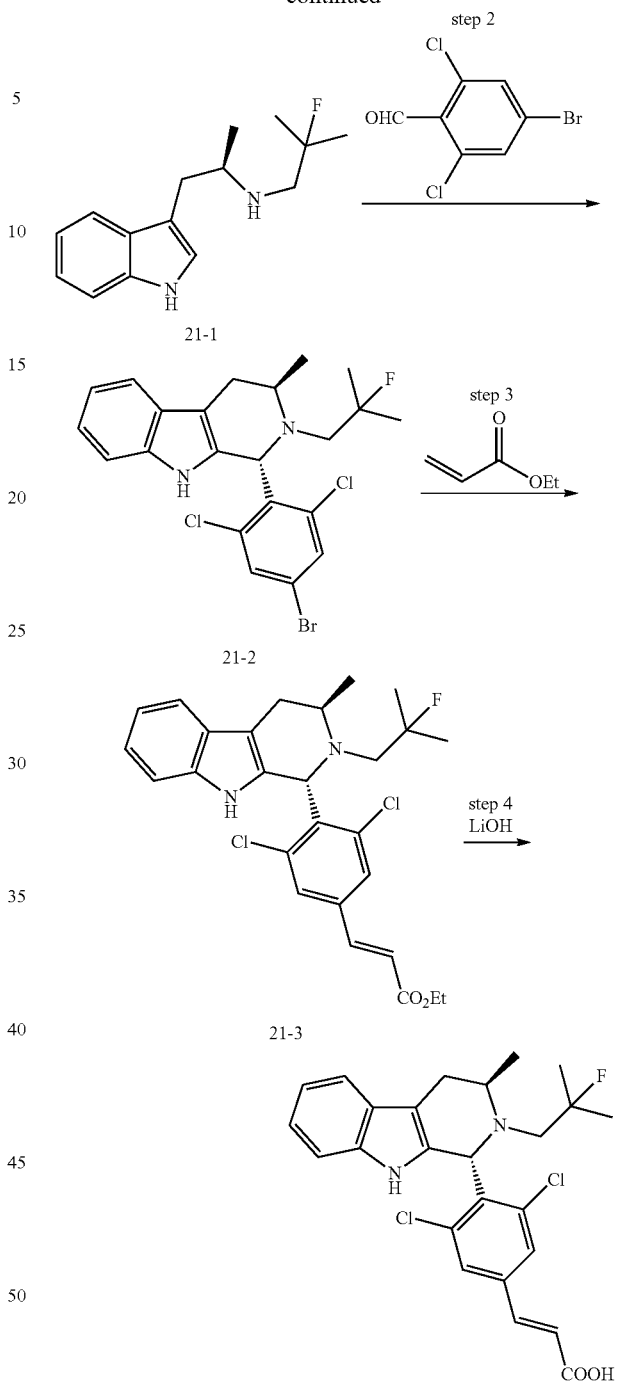

Step 1. Synthesis of 21-1

To a solution of (2R)-1-(1H-indol-3-yl)propan-2-amine (700 mg, 4.02 mmol) and 2-fluoro-2-methylpropyl trifluoromethanesulfonate (1.082 g, 4.80 mmol) in 1,4-dioxane (10 mL), was added N,N-diisopropylethylamine (1.56 g, 12.06 mmol). The resulting solution was stirred at 70° C. overnight. After cooling to room temperature, the mixture was diluted with water (50 mL), and extracted with ethyl acetate (100 mL×2). The organic phase was washed with brine (50 mL), dried over anhydrous sodium sulfate, and concentrated under vacuum to afford the desired product (830 mg, 83% yield).

Step 2. Synthesis of 21-2

A solution of 21-1 (830 mg, 3.34 mmol), 4-bromo-2,6-dichlorobenzaldehyde (710 mg, 2.80 mmol) and acetic acid (350 mg, 5.83 mmol) in toluene (10 mL) was stirred at 80° C. overnight. The mixture was then cooled to room temperature, diluted with water (50 mL), and extracted with ethyl acetate (100 mL×2). The organic phase was washed with brine (50 mL), dried over anhydrous sodium sulfate, and concentrated under vacuum to afford the desired product (1 g, 74% yield).

Step 3. Synthesis of 21-3

A solution of 21-2 (100 mg, 0.21 mmol), ethyl prop-2-enoate (31 mg, 0.31 mmol), Pd(OAc)$_2$ (95 mg, 0.42 mmol), Ph$_3$P (110 mg), and triethylamine (42 mg, 0.42 mmol) in N,N-dimethylformamide (5 mL) was stirred at 100° C. for 48 h. After cooling to room temperature, the mixture was diluted with water (50 mL), and extracted with ethyl acetate (100 mL×2). The organic phase was washed with brine (50 mL), dried over anhydrous sodium sulfate, and concentrated under vacuum. The residue was dissolved in DMF and purified by Prep-HPLC with the following condition [Column: X Bridge Shield RP18 OBD, 5 um, 19×150 mm; Mobile phase A: Water (0.05% NH$_4$HCO$_3$), Mobile Phase B: MeCN; Gradient: 25% MeCN to 54% in 8 min; Detector: UV 254 nm] to afford the desired product (76 mg, 73% yield).

Step 4. Synthesis of 21

To a solution of 21-3 (76 mg, 0.15 mmol) in tetrahydrofuran (5 mL) and water (1 mL) was added lithium hydroxide (13 mg, 0.31 mmol). The resulting solution was stirred at 25° C. for 15 h. The mixture was then diluted with water (20 mL). The pH of the solution was adjusted to 6 with hydrogen chloride (1 N), and extracted with ethyl acetate (50 mL×2). The organic phase was washed with brine (20 mL), dried over anhydrous sodium sulfate, and concentrated under vacuum. The residue was diluted with acetonitrile/water and dried by lyophilization to afford the desired product (15.6 mg, 22% yield). LCMS (ES, m/z): 476.38 [M+H]$^+$. $^1$HNMR (300 MHz, CD$_3$OD-d$_4$, ppm): δ 7.66 (s, 1H), 7.44-7.34 (m, 3H), 7.17 (dd, J=1.8, 6.6 Hz, 1H), 7.00-6.92 (m, 2H), 6.54 (d, J=15.9 Hz, 1H), 5.71 (s, 1H), 3.87-3.83 (m, 1H), 3.22-3.19 (m, 1H), 3.16-2.97 (m, 1H), 2.68-2.64 (m, 1H), 2.37-2.22 (m, 1H), 1.14-1.11 (m, 6H), 1.09 (d, J=10.2 Hz, 3H).

Example 7: Synthesis of Compound 22

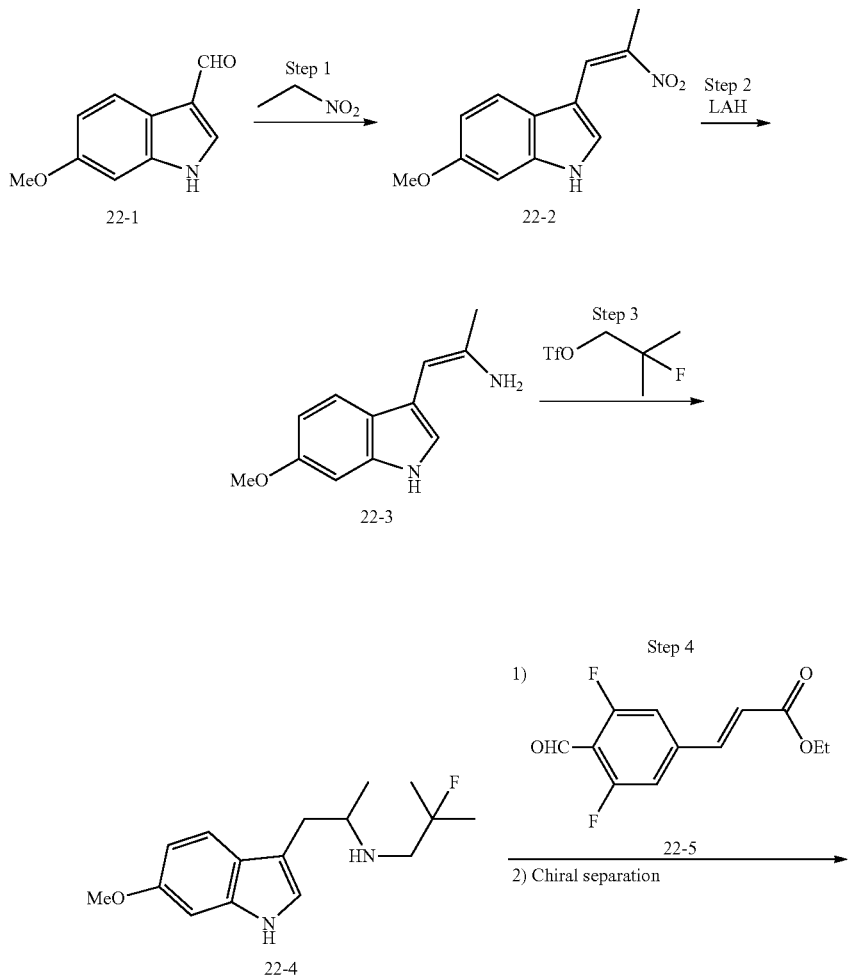

87

-continued

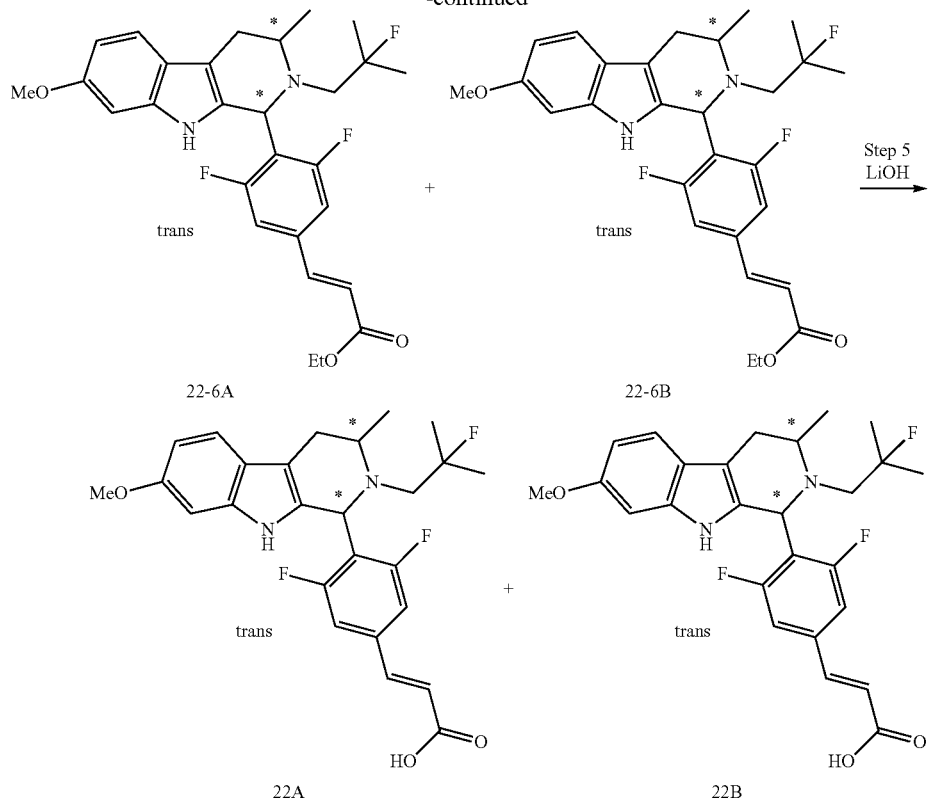

Step 1. Synthesis of 22-2

To a solution of 6-methoxy-1H-indole-3-carbaldehyde (2 g, 11.42 mmol) in toluene (20 mL), were added acetic acid (4.4 g, 57.08 mmol) and nitroethane (10 mL). The resulting solution was stirred at 130° C. for 6 h. After cooling to room temperature, the mixture was concentrated under vacuum. The resulting solution was diluted with ethyl acetate (100 mL). The mixture was washed with water (100 mL), dried over anhydrous sodium sulfate, and concentrated under vacuum to afford the desired product (2.5 g, crude).

Step 2. Synthesis of 22-3

To a solution of 22-2 (2.5 g, 10.76 mmol) in tetrahydrofuran (100 mL) was added lithium aluminium hydride (1.63 g, 42.95 mmol) portion wise at 0° C. The resulting solution was then stirred at 65° C. for 4 h. After cooling to room temperature, the reaction was then quenched by the addition of icy water (100 mL), and extracted with ethyl acetate (100 mL×3). The organic phase was washed with water (100 mL), dried over anhydrous sodium sulfate, and concentrated under vacuum to afford the desired product (1.5 g, crude).

Step 3. Synthesis of 22-4

A mixture of 1-(6-methoxy-1H-indol-3-yl)propan-2-amine (1.5 g, 7.34 mmol), 2-fluoro-2-methylpropyl trifluoromethanesulfonate (1.8 g, 8.03 mmol), and N,N-diisopropylethylamine (1.05 g, 8.08 mmol) in dioxane (20 mL) was stirred at 70° C. for 12 h. After cooling to room temperature, the mixture was diluted with water (50 mL), and extracted with ethyl acetate (50 mL×3). The organic phase was washed with brine (100 mL), dried over anhydrous sodium sulfate, and concentrated under vacuum. The residue was purified by silica gel column eluting with ethyl acetate/petroleum ether (1/10-1/1) to afford the desired product (1 g, 49% yield).

Step 4. Synthesis of 22-6A and 22-6B

A mixture of (2-fluoro-2-methylpropyl)[1-(6-methoxy-1H-indol-3-yl)propan-2-yl]amine (1 g, 3.59 mmol), ethyl (2E)-3-(3,5-difluoro-4-formylphenyl)prop-2-enoate (860 mg, 3.58 mmol), and acetic acid (1 mL) in toluene (10 mL) was stirred at 80° C. for 12 h. After cooling to room temperature, the mixture was diluted with water (50 mL), and extracted with ethyl acetate (50 mL×3). The organic phase was concentrated under vacuum. The residue was purified by silica gel column eluting with ethyl acetate/petroleum ether (1/100-1/10) to afford the desired product as a racemate (750 mg). The racemate was separated by Chiral-Prep-HPLC [Column, IA; Mobile phase: Hex:EtOH=80:20, 20 mL/min; Detector: UV=254 nm] to afford 22-6A (RT=4.45 min) as a white solid and 22-6B (RT=9.27 min) as a white solid.

Step 5. Synthesis of 22A and 22B

To a solution of 22-6A (30 mg, 0.06 mmol) in tetrahydrofuran (2 mL) and water (0.5 mL) was added lithium hydroxide (4.32 mg, 0.18 mmol). The resulting solution was stirred at room temperature for 12 h, then diluted with water (5 mL). The pH of the solution was adjusted to 6 with hydrogen chloride (1 N), and extracted with ethyl acetate (5 mL×3). The organic phase was dried over anhydrous sodium sulfate and concentrated under vacuum to afford the desired product 22A (12.5 mg, 44% yield). LCMS (ES, m/z): 473.2 [M+H]+. 1HNMR (300 MHz, CD3OD, ppm): δ7.57 (d, J=16.2 Hz, 1H), 7.29 (m, 3H), 6.75 (d, J=2.4 Hz, 1H), 6.65 (dd, J=2.1, 8.4 Hz, 1H), 6.54 (d, J=15.9 Hz, 1H), 5.31 (s, 1H), 3.76 (s, 3H), 3.69-3.67 (m, 1H), 3.05-2.98 (m, 2H), 2.62-2.38 (m, 2H), 1.20-1.11 (m, 9H).

In a similar manner, hydrolysis of 22-6B to obtain 22B. LCMS (ES, m/z): 473.2 [M+H]+. 1HNMR (300 MHz, CD3OD, ppm): δ7.57 (d, J=16.2 Hz, 1H), 7.29-7.18 (m, 3H), 6.75 (d, J=2.4 Hz, 1H), 6.65 (dd, J=2.1, 8.4 Hz, 1H), 6.54 (d, J=15.9 Hz, 1H), 5.31 (s, 1H), 3.76 (s, 3H), 3.69-3.67 (m, 1H), 3.05-2.98 (m, 2H), 2.62-2.38 (m, 2H), 1.20-1.11 (m, 9H).

Example 8: Synthesis of Compound 23

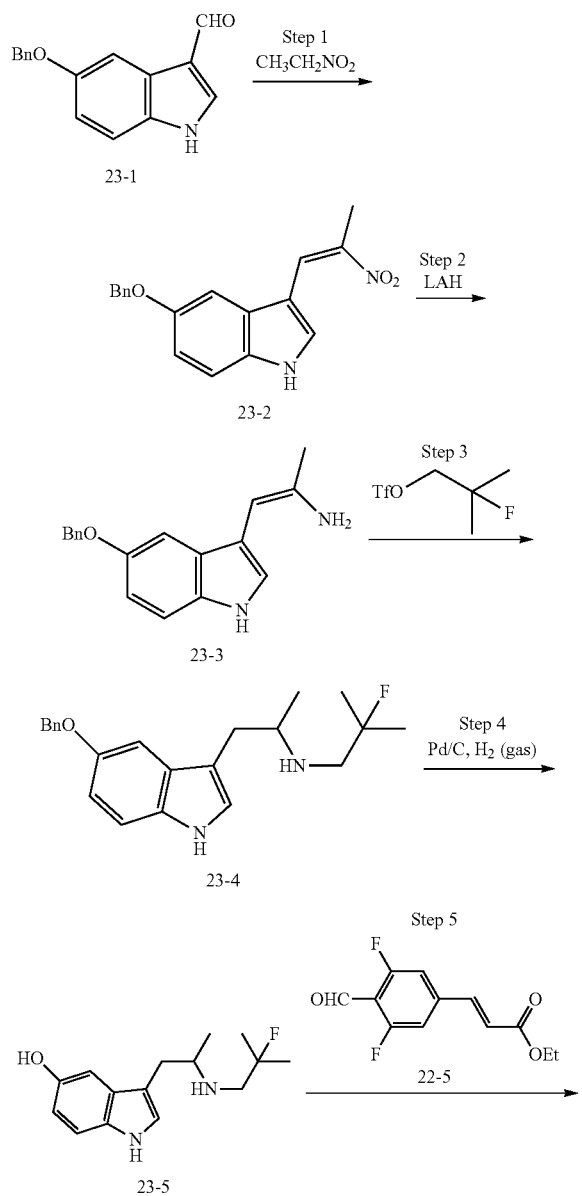

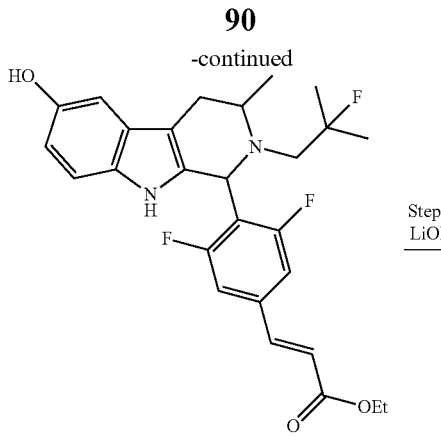

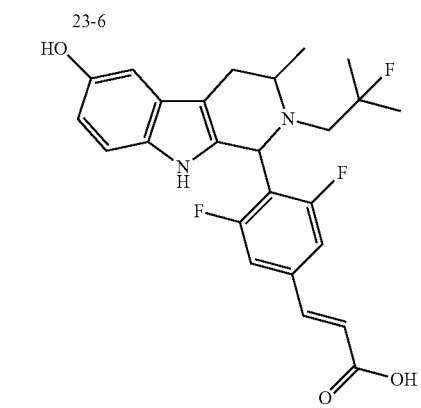

Step 1. Synthesis of 23-2

To a solution of 5-(benzyloxy)-1H-indole-3-carbaldehyde (2 g, 7.96 mmol) in toluene (20 mL), were added nitroethane (24 mL) and ammonium acetate (600 mg, 8.00 mmol). The mixture was then stirred at 130° C. for 4 h. After cooling to room temperature, the mixture was diluted with water (100 mL), and extracted with ethyl acetate (50 mL×3). The organic phase was washed with brine (50 mL×2), dried over anhydrous sodium sulfate, and concentrated under vacuum to afford the desired product (2.45 g, crude).

Step 2. Synthesis of 23-3

To a solution of lithium aluminum hydride (1.2 g, 31.62 mmol) in tetrahydrofuran (30 mL), was added 5-(benzyloxy)-3-[(1Z)-2-nitroprop-1-en-1-yl]-1H-indole (2.45 g, 7.95 mmol) in tetrahydrofuran (20 mL) dropwise. The mixture was stirred at 0° C. for 30 min, and then stirred at 65° C. for 5 h. After cooling to room temperature, the mixture was diluted with icy water (100 mL), and extracted with ethyl acetate (100 mL×3). The organic phase was washed with brine (100 mL×2), dried over anhydrous sodium sulfate, filtered, and concentrated under vacuum to afford the desired product (2.2 g, crude).

Step 3. Synthesis of 23-4

To a solution of 1-[5-(benzyloxy)-1H-indol-3-yl]propan-2-amine (1.2 g, 4.28 mmol) in 1,4-dioxane (30 mL), were added 2-fluoro-2-methylpropyl trifluoromethanesulfonate (960 mg, 4.28 mmol) and N,N-diisopropylethylamine (770 mg). The mixture was then stirred at 70° C. overnight. After cooling to room temperature, the mixture was diluted with water (100 mL), and extracted with ethyl acetate (50 mL×3). The organic phase was washed with brine (50 mL×2), dried over anhydrous sodium sulfate, and concentrated under vacuum. The residue was applied onto a silica gel column with ethyl acetate/petroleum ether (2/3) as the eluent to afford the desired product (430 mg, 28% yield).

Step 4. Synthesis of 23-5

To a solution of [1-[5-(benzyloxy)-1H-indol-3-yl]propan-2-yl](2-fluoro-2-methylpropyl)amine (430 mg, 1.21 mmol) in methanol (20 mL) was added palladium on carbon (100 mg). The mixture was stirred at room temperature for 2 h under hydrogen atmosphere (1 atm). The mixture was filtered through Celite and the filtrate was concentrated under vacuum to afford the desired product (280 mg, 87% yield).

Step 5. Synthesis of 23-6

To a solution of 3-[2-[(2-fluoro-2-methylpropyl)amino]propyl]-1H-indol-5-ol (280 mg, 1.06 mmol) in toluene (30 mL), were added ethyl (2E)-3-(3,5-difluoro-4-formylphenyl)prop-2-enoate (250 mg, 1.04 mmol) and acetic acid (200 mg, 3.33 mmol). The mixture was then stirred at 80° C. overnight. After cooling to room temperature, the mixture was diluted with water (100 mL), and extracted with ethyl acetate (50 mL×3). The organic phase was washed with brine (50 mL×2), dried over anhydrous sodium sulfate, and concentrated under vacuum. The residue was applied onto a silica gel column with ethyl acetate/petroleum ether (1:3) as the eluent to afford the desired product (180 mg, 36% yield).

Step 6. Synthesis of 23

To a solution of 23-6 (100 mg, 0.21 mmol) in tetrahydrofuran (5 mL) and water (1 mL), was added lithium hydroxide (10 mg, 0.42 mmol). The mixture was then stirred at room temperature overnight, then diluted with water (20 mL). The pH of the solution was adjusted to 6 with hydrogen chloride (1 N), and extracted with ethyl acetate (20 mL×3). The organic phase was washed with brine (20 mL×2), dried over anhydrous sodium sulfate, and concentrated under vacuum to afford the desired product (11.9 mg, 13% yield). LCMS (ES, m/z): 459.18 [M+H]+; $^1$HNMR: (300 MHz, CD$_3$OD, ppm): δ7.53 (d, J=16.2 Hz, 1H), 7.18 (d, J=9.9 Hz, 2H), 6.99 (d, J=8.7 Hz, 1H), 6.81 (d, J=2.4 Hz, 1H), 6.59-6.50 (m, 2H), 5.26 (s, 1H), 3.69-3.63 (m, 1H), 3.08-2.87 (m, 2H), 2.56-2.50 (m, 1H), 2.46-2.32 (m, 1H), 1.32-1.09 (m, 9H).

Example 9: Synthesis of Compound 24 and Derivatives Thereof

Step 1. Synthesis of 24-1

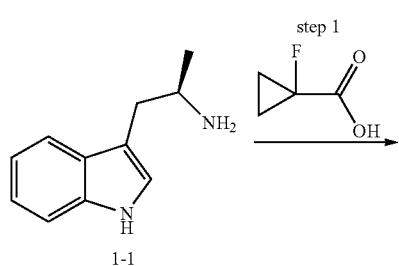

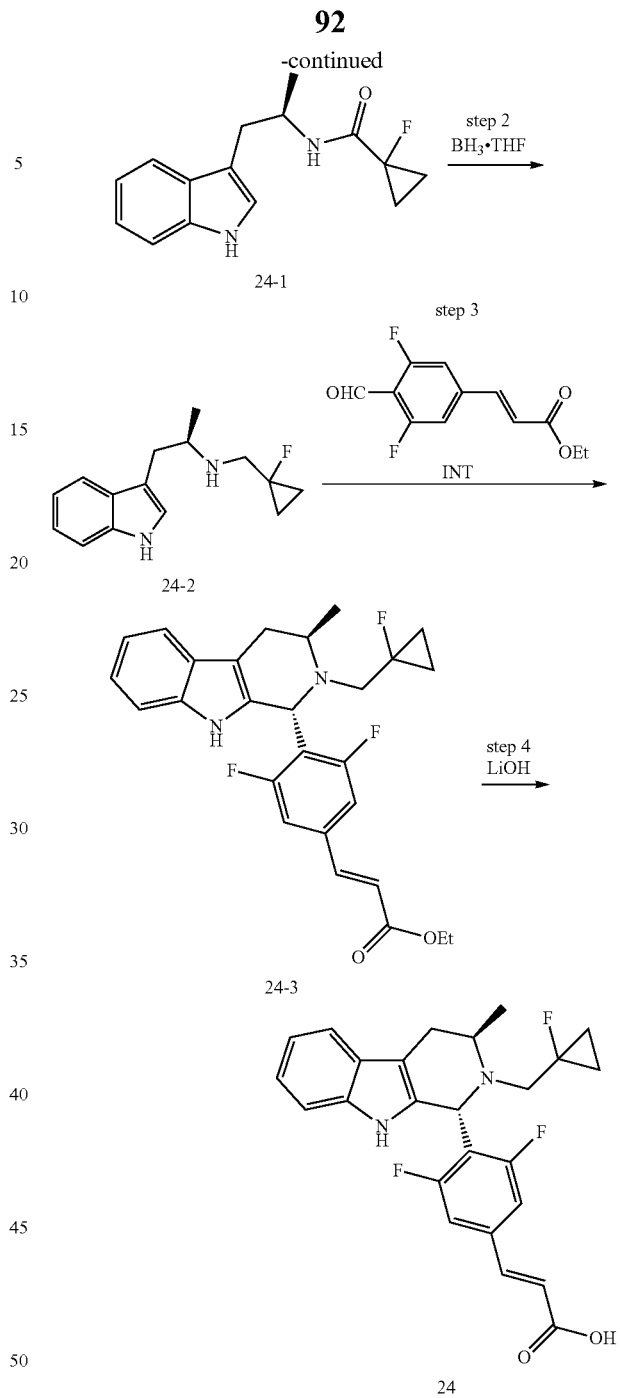

To a solution of 1-fluorocyclopropane-1-carboxylic acid (700 mg, 6.73 mmol) in N,N-dimethylformamide (10 mL), were added N,N-diisopropylethylamine (1.5 g, 11.61 mmol), HATU (2.4 g, 6.32 mmol), and (2R)-1-(1H-indol-3-yl)propan-2-amine (1 g, 5.74 mmol). After stirring at room temperature overnight, the mixture was then quenched by the addition of icy water (20 mL). The mixture was extracted with ethyl acetate (20 mL×3). The organic phase was washed with brine (20 mL×3), dried over anhydrous sodium sulfate, and concentrated under vacuum. The residue was purified on a silica gel column with ethyl acetate/petroleum ether (1:3) as the eluent to afford the desired product (600 mg, 40% yield).

Step 2. Synthesis of 24-2

A solution of 24-1 (600 mg, 2.30 mmol) in BH$_3$.THF (1 M) (20 mL) was heated to reflux overnight. After cooling to room temperature, the mixture was concentrated under vacuum, the residue was dissolved in methanol (20 mL), then heated to reflux overnight. After cooling to room temperature, the mixture was concentrated under vacuum. The residue was diluted with water (100 mL), and extracted with ethyl acetate (100 mL×3). The organic phase was washed with brine (100 mL), dried over anhydrous sodium sulfate, and concentrated under vacuum. The crude mixture was purified on a silica gel column with ethyl acetate/petroleum ether (1:2) as the eluent to afford the desired product (350 mg, 62% yield).

Step 3. Synthesis of 24-3

To a solution of (R)—N-((1-fluorocyclopropyl)methyl)-1-(1H-indol-3-yl)propan-2-amine (350 mg, 1.42 mmol) and ethyl (2E)-3-(3,5-difluoro-4-formylphenyl)prop-2-enoate (341.5 mg, 1.42 mmol) in toluene (5 mL), was added acetic acid (1 drop). After stirring at 80° C. for 2 h, the reaction mixture was cooled to room temperature, and concentrated under vacuum. The residue was purified on a silica gel column with ethyl acetate/petroleum ether (1:2) as the eluent to afford the desired product (120 mg, 18% yield).

Step 4. Synthesis of 24

To a solution of 24-3 (120 mg, 0.26 mmol) in tetrahydrofuran (0.9 mL) and water (0.1 mL), was added lithium hydroxide (12.3 mg, 0.51 mmol). The resulting solution was stirred at room temperature overnight. The pH of the solution was adjusted to 6 with hydrogen chloride (1 N), and the mixture was extracted with ethyl acetate (20 mL×3). The organic phase was washed with brine (20 mL), dried over anhydrous sodium sulfate, and concentrated under vacuum. The residue was purified on a silica gel column with ethyl acetate/petroleum ether (1:1) as the eluent to afford the desired product (49.9 mg, 44% yield). LRMS (ES, m/z): 441.30[M+H]$^+$. $^1$HNMR: (300 MHz, DMSO-d6, ppm): δ12.50 (br s, 1H), 10.59 (s, 1H), 7.56-7.40 (m, 4H), 7.19 (d, J=5.7 Hz, 1H), 700-7.6.95 (m, 2H), 6.67 (d, J=12 Hz, 1H), 5.23 (s, 1H), 3.58-3.56 (m, 1H), 3.09-2.88 (m, 2H), 2.67-2.63 (m, 2H), 1.07 (d, J=5.1 Hz, 3H) 0.94-0.89 (m, 2H), 0.56-0.51 (n, 2H).

Using the similar procedures described above, the following additional compounds of the invention were prepared.

TABLE 4

Exemplary Derivatives of Compound 24

| Example No. | Compound | [M + H]$^+$ | HNMR and Chiral HPLC |
|---|---|---|---|
| 25 | | 479.3 | $^1$HNMR (300 MHz, CDCl$_3$, ppm) δ 7.65-7.50 (m, 3 H), 7.42 (s, 1 H), 7.21 (s, 2 H), 7.15-7.08 (m, 2 H), 6.47 (d, J = 15.9 Hz, 1 H), 5.76 (s, 1 H), 3.76-3.69 (m, 1 H), 3.25-3.07 (m, 2 H), 2.72 (d, J = 15.0 Hz, 1 H), 2.69-2.47 (m, 1 H), 1.45 (t, J = 18.9 Hz, 3 H), 1.16 (d, J = 6.6 Hz, 3 H). |
| 26A | | 477.9 | Chiral HPLC [Column: IA, 100 mm, 4.6 mm, 0.6 mL/min, Mobile Phase: hexane (0.1% TFA)/ethanol; Gradient: 20% EtOH; Detector: 254 nm], Retention time = 3.70 min.<br>$^1$HNMR (300 MHz, CD$_3$OD, ppm): δ 7.47-7.42 (m, 2 H), 7.26 (d, J = 11.1 Hz, 1 H), 7.12-7.03 (m, 2 H), 6.77-6.71 (m, 1 H), 6.54 (d, J = 8.1 Hz, 1 H), 5.44 (s, 1 H), 3.81-3.77 (m, 1 H), 3.16-3.10 (m, 1 H), 3.07-2.95 (m, 1 H), 2.59 (d, J = 14.7 Hz, 1 H), 2.40-2.25 (m, 1 H), 1.16 (s, 3 H), 1.11-1.09 (m, 6H) |

TABLE 4-continued

Exemplary Derivatives of Compound 24

| Example No. | Compound | [M + H]⁺ | HNMR and Chiral HPLC |
|---|---|---|---|
| 26B | (structure, trans) | 477.9 | Chiral HPLC [Column: IA, 100 mm, 4.6 mm, 0.6 mL/min, Mobile Phase: hexane (0.1% TFA)/ethanol; Gradient: 20% EtOH; Detector: 254 nm], Retention time = 3.17 min. $^1$HNMR (300 MHz, CDCl$_3$, ppm): δ 7.70-7.58 (m, 1 H), 7.36 (s, 1 H), 7.17-7.08 (m, 3 H), 6.91-6.82 (m, 1 H), 6.43 (d, J = 16.5 Hz, 1 H), 5.43 (s, 1 H), 3.76-3.66 (m, 1 H), 3.21-3.16 (m, 1 H), 3.02-2.88 (m, 1 H), 2.59 (d, J = 14.4 Hz, 1 H), 2.35-2.14 (m, 1 H), 1.25 (s, 3 H), 1.19-1.09 (m, 6 H). |
| 27A | (structure, trans) | 493.3 | Chiral HPLC [Column: AD, 100 mm, 4.6 mm, 0.6 mL/min, Mobile Phase: hexane (0.1% TFA)/IPA; Gradient: 10% IPA; Detector: 254 nm], Retention time = 4.19 min. $^1$HNMR (300 MHz, CD$_3$OD, ppm): δ 7.64 (s, 1 H), 7.42 (s, 1 H), 7.37-7.32 (d, J = 15.6 Hz, 1 H), 7.12-7.02 (m, 2 H), 6.73 (dt, J = 2.4, 9.0 Hz, 1 H), 6.55 (d, J = 15.6 Hz, 1 H), 5.69(s, 1 H), 3.86-3.82 (m, 1 H), 3.18-2.96 (m, 2 H), 2.60 (d, J = 14.4 Hz, 1 H), 2.36-2.21 (m, 1 H), 1.20-1.07 (m, 9H). |
| 27B | (structure, trans) | 493.3 | Chiral HPLC [Column: AD, 100 mm, 4.6 mm, 0.6 mL/min, Mobile Phase: hexane (0.1% TFA)/IPA; Gradient: 10% IPA; Detector: 254 nm], Retention time = 11.72 min. $^1$HNMR (300 MHz, CD$_3$OD, ppm): δ 7.65 (s, 1 H), 7.43 (s, 1 H), 7.35 (d, J = 15.9 Hz, 1 H), 7.12-7.02 (m, 2 H), 6.73 (dt, J = 2.4, 9.0 Hz, 1 H), 6.55(d, J = 15.9 Hz, 1 H), 5.70(s, 1 H), 3.86-3.82 (m, 1 H), 3.17-2.96 (m, 2 H), 2.62 (d, J = 14.7 Hz, 1 H), 2.36-2.21 (m, 1 H), 1.21-1.08 (m, 9 H). |
| 28A | (structure, trans) | 497.3 | Chiral HPLC [Column: AD, 100 mm, 4.6 mm, 0.6 mL/min, Mobile Phase: hexane (0.1% TFA)/ethanol; Gradient: 10% EtOH; Detector: 254 nm], Retention time = 5.21 min. $^1$HNMR (300 MHz, CD$_3$OD, ppm) δ 7.80 (s, 1 H), 7.62-7.56 (m, 2H), 7.14 (dd, J = 4.2 Hz, J = 8.7 Hz, 1H), 7.09 (dd, J = 2.7 Hz, J = 9.9 Hz, 1H), 6.78 (td, J = 2.4 Hz, J = 9.3 Hz, 1H), 6.61 (d, J = 15.9 Hz, 1H), 5.81 (s, 1H), 3.79-3.71 (m, 1H), 3.22-3.14 (m, 2H), 2.72-2.67 (m, 1H), 2.64-2.53 (m, 1H), 1.43 (t, J = 18.9 Hz, 3H), 1.19 (d, J = 6.3 Hz, 3H). |

TABLE 4-continued

Exemplary Derivatives of Compound 24

| Example No. | Compound | [M + H]+ | HNMR and Chiral HPLC |
|---|---|---|---|
| 28B | (structure, trans) | 497.3 | Chiral HPLC [Column: IA, 100 mm, 4.6 mm, 0.6 mL/min, Mobile Phase: hexane (0.1% TFA)/ethanol; Gradient: 10% EtOH; Detector: 254 nm], Retention time = 10.04 min. $^1$HNMR (300 MHz, CD$_3$OD, ppm) δ 7.80 (s, 1 H), 7.62-7.57 (m, 2H), 7.14 (dd, J = 4.5 Hz, J = 8.7 Hz, 1H), 7.09 (dd, J = 2.4 Hz, J = 9.9 Hz, 1H), 6.79 (td, J = 2.7 Hz, J = 9.3 Hz, 1H), 6.61 (d, J = 15.9 Hz, 1H), 5.81 (s, 1H), 3.79-3.71 (m, 1H), 3.22-3.10 (m, 2H), 2.72-2.67 (m, 1H), 2.65-2.54 (m, 1H), 1.43 (t, J = 18.6 Hz, 3H), 1.19 (d, J = 6.9 Hz, 3H). |
| 29A | (structure) | 447.1 | $^1$H-NMR: (300 MHz, DMSO-d6, ppm): δ 12.57 (brs, 1 H), 10.61 (s, 1 H), 7.56-7.40 (m, 4 H), 7.20 (d, J = 7.5 Hz, 1 H), 7.04-6.93 (m, 2 H), 6.67 (d, J = 15.9 Hz, 1 H), 5.25 (s, 1 H), 3.47-3.41 (m, 1 H), 3.18-3.04 (m, 1 H), 2.91-2.86 (m, 1 H), 2.64-2.51 (m, 2H), 1.53-1.41 (m, 3 H), 1.10 (d, J = 6.3 Hz, 3 H). |
| 30 | (structure) | 437.5 | $^1$HNMR (300 MHz, DMSO-d$_6$, ppm): 10.53 (s, 1 H), 7.55-7.39 (m, 4 H), 7.18 (d, J = 7.2 Hz, 1 H), 7.02-6.92 (m, 2 H), 6.67 (d, J = 15.9 Hz, 1 H), 5.12 (s, 1 H), 3.71-3.67 (m, 1 H), 2.97-2.91 (m, 1 H), 2.61-2.57 (m, 1 H), 2.30 (q, J = 12.9 Hz, 2 H), 0.98 (d, J = 6.3 Hz, 3 H), 0.91 (s, 3 H), 0.34-0.29 (m, 2 H), 0.19-0.11 (m, 2 H). |
| 31A | (structure, trans) | 497.4 | Chiral HPLC [Column: AD, 100 mm, 4.6 mm, 0.6 mL/min, Mobile Phase: hexane (0.1% TFA)/ethanol; Gradient: 20% EtOH; Detector: 254 nm], Retention time = 3.67 min. $^1$HNMR (300 MHz, CD$_3$OD, ppm): δ 7.56 (d, J = 16.2 Hz, 1 H), 7.46 (d, J = 6.9 Hz, 1 H), 7.25-7.19 (m, 3 H), 7.07-6.92 (m, 2 H), 6.55 (d, J = 15.9 Hz, 1 H), 5.63 (s, 1 H), 4.22-4.18 (m, 1 H), 3.17-3.13 (m, 2 H), 2.74-2.6 (m, 2 H), 1.4-1.12 (m, 6 H). |

TABLE 4-continued

Exemplary Derivatives of Compound 24

| Example No. | Compound | [M + H]+ | HNMR and Chiral HPLC |
|---|---|---|---|
| 31B | (structure, trans) | 497.4 | Chiral HPLC [Column: AD, 100 mm, 4.6 mm, 0.6 mL/min, Mobile Phase: hexane (0.1% TFA)/ethanol; Gradient: 20% EtOH; Detector: 254 nm], Retention time = 4.03 min.<br>$^1$HNMR (300 MHz, CD$_3$OD, ppm): δ 7.49-7.44(m, 2 H), 7.22-7.19 (m, 3 H), 7.06-6.97 (m, 2 H), 6.55(d, J = 15.9 Hz, 1 H), 5.62 (s, 1 H), 4.26-4.15 (m, 1 H), 3.17-3.08 (m, 2 H), 2.79-2.59 (m, 2 H), 1.44-1.12 (m, 6 H). |
| 32A | (structure, trans) | 444.5 | Chiral HPLC [Column: AD, 100 mm, 4.6 mm, 0.6 mL/min, Mobile Phase: hexane (0.1% TFA)/ethanol; Gradient: 20% EtOH; Detector: 254 nm], Retention time = 8.73 min.<br>$^1$HNMR (300 MHz, DMSO-d$_6$, ppm): δ 8.11-8.09 (m, 1 H), 7.83 (dd, J = 1.5, 7.8 Hz, 1 H), 7.55 (d, J = 15.9 Hz, 1 H), 7.45 (d, J = 10.5 Hz, 2 H), 7.04-6.99 (m, 1 H), 6.67 (d, J = 15.9 Hz, 1 H), 5.25 (s, 1 H), 3.58-3.55 (m, 1 H), 2.93-2.80 (m, 2 H), 2.62-2.32 (m, 2 H), 1.26-1.05(m, 9 H). |
| 32B | (structure, trans) | 444.5 | Chiral HPLC [Column: AD, 100 mm, 4.6 mm, 0.6 mL/min, Mobile Phase: hexane (0.1% TFA)/ethanol; Gradient: 20% EtOH; Detector: 254 nm], Retention time = 11.3 min.<br>$^1$HNMR (300 MHz, DMSO-d$_6$, ppm): δ 8.11-8.09 (m, 1 H), 7.84 (dd, J = 1.5, 7.8 Hz, 1 H), 7.53 (d, J = 16.2 Hz, 1 H), 7.43 (d, J = 10.5 Hz, 2 H), 7.04-6.99 (m, 1 H), 6.68 (d, J = 16.2 Hz, 1 H), 5.25 (s, 1 H), 3.58-3.55 (m, 1 H), 2.93-2.74 (m, 2 H), 2.62-2.28 (m, 2 H), 1.26-1.05 (m, 9 H). |
| 33A | (structure, trans) | 465.4 | Chiral HPLC [Column: IA, 100 mm, 4.6 mm, 0.6 mL/min, Mobile Phase: hexane (0.1% TFA)/ethanol; Gradient: 10% EtOH; Detector: 254 nm], Retention time = 9.26 min.<br>$^1$HNMR (300 MHz, CD$_3$OD, ppm): δ 7.58 (d, J = 15.9 Hz, 1 H), 7.23 (d, J = 10.2 Hz, 2 H), 7.15-7.06 (m, 2 H), 6.81-6.74 (m, 1 H), 6.54 (d, J = 15.9 Hz, 1 H), 5.33 (s, 1 H), 3.58-3.55 (m, 1 H), 3.20-2.95 (m, 2 H), 2.71-2.57 (m, 2 H), 1.50-1.37 (m, 3 H), 1.14 (d, J = 6.6 Hz, 3 H). |

TABLE 4-continued

Exemplary Derivatives of Compound 24

| Example No. | Compound | [M + H]⁺ | HNMR and Chiral HPLC |
|---|---|---|---|
| 33B | (structure, trans) | 465.4 | Chiral HPLC [Column: IA, 100 mm, 4.6 mm, 0.6 mL/min, Mobile Phase: hexane (0.1% TFA)/ethanol; Gradient: 10% EtOH; Detector: 254 nm], Retention time = 9.07 min.<br>¹HNMR (300 MHz, CD₃OD, ppm) δ 7.44 (d, J = 15.9 Hz, 1 H), 7.20-7.05 (m, 4 H), 6.81-6.74 (m, 1 H), 6.54 (d, J = 15.9 Hz, 1 H), 5.31 (s, 1 H), 3.58-3.55 (m, 1 H), 3.20-2.95 (m, 2 H), 2.71-2.57 (m, 2 H), 1.50-1.37 (m, 3 H), 1.14 (d, J = 6.6 Hz, 3 H). |
| 34A | (structure, trans) | 461.3 | Chiral-Prep-HPLC [Column: IA, 100 mm, 4.6 mm, 20 mL/min, Mobile Phase: Hexane/Ethanol; Gradient: 4% EtOH; Rate: 20 mL/min; 20 min; Detector: 254 nm], Retention time = 13.64 min.<br>¹HNMR: (300 MHz, CD₃OD, ppm): δ 7.56 (d, J = 13.8 Hz, 1 H), 7.35 (dd, J = 5.4, 8.4 Hz, 1 H), 7.20 (d, J = 9.9 Hz, 2 H), 6.87 (dd, J = 2.4, 9.9 Hz, 1 H), 6.78-6.71 (m, 1 H), 6.52 (d, J = 16.2 Hz 1 H), 5.27 (s, 1 H), 3.75-3.66 (m, 1 H), 3.06-2.88 (m, 2 H), 2.62-2.56 (m, 1 H), 2.47-2.33 (m, 1 H), 1.20-1.05 (m, 9 H). |
| 34B | (structure, trans) | 461.3 | Chiral-Prep-HPLC [Column: IA, 100 mm, 4.6 mm, 20 mL/min, Mobile Phase: Hexane/Ethanol; Gradient: 4% EtOH; Rate: 20 mL/min; 20 min; Detector: 254 nm], Retention time = 18.38 min.<br>¹HNMR: (300 MHz, CD₃OD, ppm): δ 7.56 (d, J = 13.8 Hz, 1 H), J = 13.8 Hz 1 H), 7.37-7.33 (dd, J = 5.1, 8.4 Hz, 1 H), 7.20 (d, J = 10.2 Hz, 2 H), 6.89-6.85 (dd, J = 2.4, 10.2 Hz, 1 H), 6.78-6.71 (m, 1 H), 6.52 (d, J = 16.2 Hz, 1 H), 5.27 (s, 1 H), 3.75-3.65 (m, 1 H), 3.06-2.88 (m, 2 H), 2.62-2.56 (m, 1 H), 2.47-2.33 (m, 1 H), 1.23-1.09 (m, 9 H). |
| 35A | (structure, trans) | 465.3 | Chiral HPLC [Column: IA, 100 mm, 4.6 mm, 0.6 mL/min, Mobile Phase: hexane (0.1% TFA)/IPA; Gradient: 10% IPA; Detector: 254 nm], Retention time = 7.59 min.<br>¹HNMR (300 MHz, CD₃OD, ppm): δ 7.57(d, J = 15.9 Hz 1 H), 7.36 (dd, J = 2.4, 8.4 Hz, 1 H), 7.23 (d, J = 9.9 Hz, 2 H), 6.89 (dd, J = 2.4, 9.9 Hz, 1 H), 6.79-6.72 (m, 1 H), 6.54 (d, J = 15.9 Hz, 1 H), 5.31 (s, 1 H), 3.58-3.54 (m, 1 H), 3.11-2.96 (m, 2 H), 2.67-2.57 (m, 2 H), 1.49-1.13 (m, 6 H). |

TABLE 4-continued

Exemplary Derivatives of Compound 24

| Example No. | Compound | [M + H]⁺ | HNMR and Chiral HPLC |
|---|---|---|---|
| 35B | (structure, trans) | 465.3 | Chiral HPLC [Column: IA, 100 mm, 4.6 mm, 0.6 mL/min, Mobile Phase: hexane (0.1% TFA)/IPA; Gradient: 10% IPA; Detector: 254 nm], Retention time = 10.89 min.<br>¹HNMR (300 MHz, CD₃OD, ppm): δ 7.57(d, J = 15.9 Hz 1 H), 7.36(dd, J = 2.4, 8.4 Hz, 1 H), 7.23 (d, J = 9.9 Hz, 2 H), 6.89 (dd, J = 2.4, 9.9 Hz, 1 H), 6.79-6.72 (m, 1 H), 6.54 (d, J = 15.2 Hz, 1 H), 5.31 (s, 1 H), 3.58-3.54 (m, 1 H), 3.12-2.96 (m, 2 H), 2.67-2.57 (m, 2 H), 1.49-1.13 (m, 6 H). |
| 36 | (structure, trans) | 459.3 | ¹HNMR (300 MHz, CD₃OD, ppm): δ 7.38 (d, J = 15.6 Hz, 1 H), 7.21 (d, J = 8.4 Hz, 1 H), 7.11 (d, J = 10.2 Hz, 2 H), 6.62 (d, J = 2.1 Hz, 1 H), 6.56-6.49 (m, 2 H), 5.22 (s, 1 H), 3.66-3.63 (m, 1 H), 3.07-2.92 (m, 2 H), 2.57-2.31 (m, 2 H), 1.21-1.08 (m, 9 H). |
| 37A | (structure, trans) | 473.2 | Chiral HPLC [Column: AD, 100 mm, 4.6 mm, 0.6 mL/min, Mobile Phase: hexane (0.1% TFA)/IPA; Gradient: 20% IPA; Detector: 254 nm], Retention time = 7.37 min.<br>¹HNMR (300 MHz, CD₃OD, ppm): δ7.53 (d, J = 15.9 Hz, 1 H), 7.18 (d, J = 10.2 Hz, 2H), 7.06 (d, J = 9 Hz, 1 H), 6.93 (d, J = 2.1 Hz, 1 H), 6.67 (dd, J = 2.4, 8.7 Hz, 1 H), 6.52(d, J = 15.9 Hz, 1 H), 5.34 (s, 1 H), 3.84 (s, 3 H), 3.69-3.67 (m, 1 H), 3.06-2.89 (m, 2 H), 2.62-2.56 (m, 1 H), 2.47-2.03 (m, 1H), 1.32-1.00 (m, 9 H). |
| 37B | (structure, trans) | 473.2 | Chiral HPLC [Column: AD, 100 mm, 4.6 mm, 0.6 mL/min, Mobile Phase: hexane (0.1% TFA)/IPA; Gradient: 20% IPA; Detector: 254 nm], Retention time = 5.54 min.<br>¹HNMR (300 MHz, CD₃OD, ppm): δ7.53 (d, J = 15.9 Hz, 1 H), 7.18 (d, J = 9.9 Hz, 2 H), 7.06 (d, J = 8.4 Hz, 1 H), 6.93 (d, J = 2.1 Hz, 1 H), 6.67 (dd, J = 2.4, 8.7 Hz, 1 H), 6.52 (d, J = 15.9 Hz, 1 H), 5.27 (s, 1 H), 3.88 (s, 3 H), 3.81-3.66 (m, 1 H), 3.06-2.83 (m, 2 H), 2.61-2.55 (m, 1 H), 2.46-2.33 (m, 1H), 1.32-0.90 (m, 9 H). |

TABLE 4-continued

Exemplary Derivatives of Compound 24

| Example No. | Compound | [M + H]+ | HNMR and Chiral HPLC |
|---|---|---|---|
| 38A | (structure, trans) | 477.9 | Chiral HPLC [Column: IA, 100 mm, 4.6 mm, 0.6 mL/min, Mobile Phase: hexane (0.1% TFA)/ethanol; Gradient: 20% EtOH; Detector: 254 nm], Retention time = 3.70 min.<br>¹HNMR (300 MHz, CD₃OD, ppm): δ 7.47-7.42 (m, 2 H), 7.26 (d, J = 11.1 Hz, 1H), 7.12-7.03 (m, 2 H), 6.77-6.71 (m, 1 H), 6.54 (d, J = 8.1 Hz, 1 H), 5.44 (s, 1 H), 3.81-3.77 (m, 1 H), 3.16-3.10 (m, 1 H), 3.07-2.95 (m, 1 H), 2.59 (d, J = 14.7 Hz, 1 H), 2.40-2.25 (m, 1 H), 1.16 (s, 3 H), 1.11-1.09 (m, 6 H). |
| 38B | (structure, trans) | 477.9 | Chiral HPLC [Column: IA, 100 mm, 4.6 mm, 0.6 mL/min, Mobile Phase: hexane (0.1% TFA)/ethanol; Gradient: 20% EtOH; Detector: 254 nm], Retention time = 3.17 min.<br>¹HNMR (300 MHz, CDCl₃, ppm): δ 7.70-7.58 (m, 1 H), 7.36 (s, 2 H), 7.17-7.08 (m, 3 H), 6.91-6.82 (m, 1 H), 6.43 (d, J = 16.5 Hz, 1 H), 5.43 (s, 1 H), 3.76-3.66 (m, 1 H), 3.21-3.16 (m, 1 H), 3.02-2.88 (m, 1 H), 2.59 (d, J = 14.4 Hz, 1 H), 2.35-2.14 (m, 1 H), 1.25 (s, 3 H), 1.19-1.09 (m, 6 H). |
| 39A | (structure, trans) | 443.5 | Chiral HPLC [Column: IA, 100 mm, 4.6 mm, 0.6 mL/min, Mobile Phase: hexane (0.1% TFA)/ethanol; Gradient: 15% EtOH; Detector: 254 nm], Retention time = 9.72 min.<br>¹HNMR (300 MHz, CD₃OD, ppm): δ 7.44 (d, J = 15.9 Hz, 1 H), 7.17-7.04 (m, 4 H), 6.79-6.72 (m, 1 H), 6.53 (d, J = 15.9 Hz, 1 H), 5.18 (s, 1 H), 3.49-3.29 (m, 1 H), 2.94-2.92 (m, 1 H), 2.61-2.46 (m, 2 H), 2.21-2.08 (m, 1H), 1.72-1.69 (m, 1 H), 1.10 (d, J = 6.6 Hz, 3 H), 0.84 (d, J = 6.6 Hz, 3 H), 0.71 (d, J = 6.6 Hz, 3 H). |
| 39B | (structure, trans) | 443.5 | Chiral HPLC [Column: IA, 100 mm, 4.6 mm, 0.6 mL/min, Mobile Phase: hexane (0.1% TFA)/ethanol; Gradient: 15% EtOH; Detector: 254 nm], Retention time = 8.42 min.<br>¹HNMR (300 MHz, CD₃OD, ppm): δ 7.43 (d, J = 15.9 Hz, 1 H), 7.17-7.04 (m, 4 H), 6.79-6.72 (m, 1 H), 6.53 (d, J = 15.9 Hz, 1 H), 5.18 (s, 1 H), 3.51-3.29 (m, 1 H), 2.98-2.92 (m, 1 H), 2.61-2.46 (m, 2 H), 2.21-2.08 (m, 1H), 1.74-1.69 (m, 1 H), 1.10 (d, J = 6.6 Hz, 3 H), 0.84 (d, J = 6.6 Hz, 3 H), 0.71 (d, J = 6.6 Hz, 3 H). |

TABLE 4-continued

Exemplary Derivatives of Compound 24

| Example No. | Compound | [M + H]+ | HNMR and Chiral HPLC |
|---|---|---|---|
| 40A | 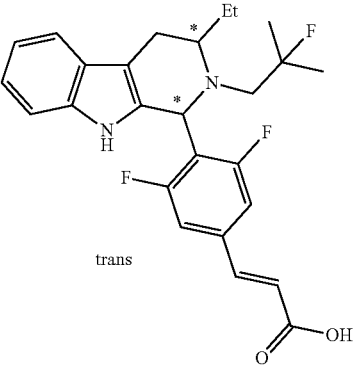 [SMILES: CCC1Cc2c([nH]c3ccccc23)C(c2c(F)cc(/C=C/C(=O)O)cc2F)N1CC(C)(C)F] trans | 457.4 | Chiral HPLC [Column: AD, 100 mm, 4.6 mm, 0.6 mL/min, Mobile Phase: hexane (0.1% TFA)/ethanol; Gradient: 30% EtOH; Detector: 254 nm], Retention time = 3.18 min. $^1$H-NMR (300 MHz, CD$_3$OD, ppm): δ 7.43-7.34 (m, 2 H), 7.20-7.10 (m, 3 H), 7.03-6.94 (m, 2 H), 6.52 (d, J = 15.9 Hz, 1 H), 5.39 (s, 1 H), 3.31-3.24 (m, 1 H), 2.90-2.83 (m, 2 H), 2.75-2.65 (m, 1 H), 2.56-2.49 (m, 1 H), 1.75-1.65 (m, 1 H), 1.45-1.35 (m, 1 H), 1.34-1.10 (m, 6 H), 0.91 (m, 3 H). |
| 40B | 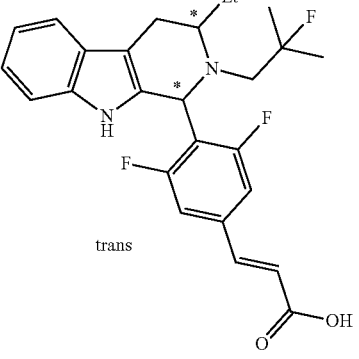 trans | 457.4 | Chiral HPLC [Column: AD, 100 mm, 4.6 mm, 0.6 mL/min, Mobile Phase: hexane (0.1% TFA)/ethanol; Gradient: 30% EtOH; Detector: 254 nm], Retention time = 4.01 min. $^1$H-NMR (300 MHz, CD$_3$OD, ppm): δ 7.43-7.34 (m, 2 H), 7.20-7.10 (m, 3 H), 7.03-6.94 (m, 2 H), 6.52 (d, J = 15.9 Hz, 1 H), 5.39 (s, 1 H), 3.31-3.24 (m, 1 H), 2.90-2.83 (m, 2 H), 2.75-2.65 (m, 1 H), 2.56-2.49 (m, 1 H), 1.75-1.65 (m, 1 H), 1.45-1.35 (m, 1 H), 1.34-1.10 (m, 6 H), 0.91 (m, 3 H). |
| 41 | 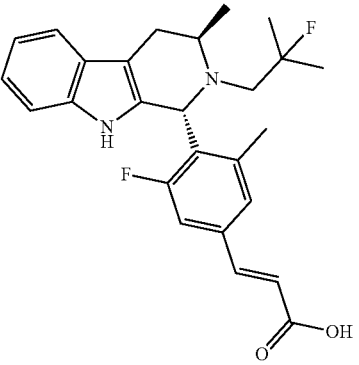 [SMILES: Cc1cc(/C=C/C(=O)O)cc(F)c1[C@@H]1c2[nH]c3ccccc3c2C[C@@H](C)N1CC(C)(C)F] | 439.2 | $^1$HNMR (300 MHz, CD$_3$OD, ppm): δ 7.56 (d, J = 15.9 Hz, 1 H), 7.42-7.39 (m, 1 H), 7.25 (d, J = 11.1 Hz, 1 H), 7.18-7.12 (m, 2 H), 7.02-6.93 (m, 2 H), 6.49 (d, J = 15.9 Hz, 1 H), 5.34 (s, 1 H), 3.86-3.82 (m, 1 H), 3.18-3.12 (m, 1 H), 3.02-2.93 (m, 1 H), 2.69 (d, J = 15 Hz, 1 H), 2.37-2.22 (m, 1 H), 2.01 (s, 3 H), 1.16-1.06 (m, 9 H). |
| 42A | 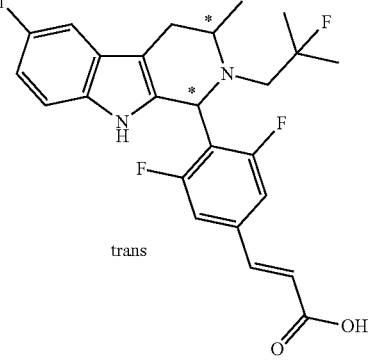 trans | 477.3 | Chiral HPLC [Column: IA, 100 mm, 4.6 mm, 0.6 mL/min, Mobile Phase: hexane (0.1% TFA)/ethanol; Gradient: 10% EtOH; Detector: 254 nm], Retention time = 9.58 min. $^1$HNMR (300 MHz, CDCl$_3$, ppm): δ 7.62 (d, J = 16.2 Hz, 1H), 7.53-7.42 (m, 2H), 7.19-6.98 (m, 4H), 6.42 (d, J = 15.6 Hz, 1H), 5.32 (s, 1 H), 3.75-3.60 (m, 1H), 3.14-2.71 (m, 2H), 2.67-2.25 (m, 2H), 1.39-0.99 (m, 9H). |

TABLE 4-continued

Exemplary Derivatives of Compound 24

| Example No. | Compound | [M + H]⁺ | HNMR and Chiral HPLC |
|---|---|---|---|
| 42B | (structure, trans) | 477.3 | Chiral HPLC [Column: IA, 100 mm, 4.6 mm, 0.6 mL/min, Mobile Phase: hexane (0.1% TFA)/ethanol; Gradient: 10% EtOH; Detector: 254 nm], Retention time = 7.11 min. ¹HNMR (300 MHz, CDCl₃, ppm): δ 7.62 (d, J = 15.9 Hz, 1H), 7.52-7.42 (m, 2H), 7.18-6.98 (m, 4H), 6.42 (d, J = 15.6 Hz, 1H), 5.31 (s, 1 H), 3.75-3.60 (m, 1H), 3.14-2.73 (m, 2H), 2.66-2.27 (m, 2H), 1.35-0.98 (m, 9H). |
| 43A | (structure, trans) | 477.2 | Chiral HPLC [Column: AD, 100 mm, 4.6 mm, 0.6 mL/min, Mobile Phase: hexane (0.1% TFA)/IPA; Gradient: 30% IPA; Detector: 254 nm], Retention time = 3.15 min. ¹HNMR (300 MHz, CDCl₃, ppm): δ 7.61 (d, J = 16.2 Hz, 1 H), 7.47 (s, 1 H), 7.42 (d, J = 8.4 Hz, 1 H), 7.21 (s, 1 H), 7.09-7.01 (m, 3 H), 6.42 (d, J = 15.9 Hz, 1 H), 5.30 (s, 1 H), 3.64-3.54 (m, 1 H), 3.08-3.01 (m, 1 H), 2.92-2.80 (m, 1 H), 2.62-2.56 (m, 1 H), 2.47-2.34 (m, 1 H), 1.22 (t, J = 22.5 Hz, 6 H), 1.10 (d, J = 6.3 Hz, 3 H). |
| 43B | (structure, trans) | 477.2 | Chiral HPLC [Column: AD, 100 mm, 4.6 mm, 0.6 mL/min, Mobile Phase: hexane (0.1% TFA)/IPA; Gradient: 30% IPA; Detector: 254 nm], Retention time = 2.72 min. ¹HNMR (300 MHz, CDCl₃, ppm): δ 7.61 (d, J = 15.9 Hz, 1 H), 7.47 (s, 1 H), 7.42 (d, J = 8.1 Hz, 1 H), 7.21 (s, 1 H), 7.09-7.01 (m, 3 H), 6.42 (d, J = 15.9 Hz, 1 H), 5.30 (s, 1 H), 3.64-3.54 (m, 1 H), 3.08-3.01 (m, 1 H), 2.92-2.80 (m, 1 H), 2.62-2.56 (m, 1 H), 2.47-2.34 (m, 1 H), 1.22 (t, J = 22.2 Hz, 6 H), 1.11 (d, J = 6.6 Hz, 3 H). |
| 44A | (structure, trans) | 448.5 | Chiral HPLC [Column: AD, 100 mm, 4.6 mm, 0.6 mL/min, Mobile Phase: hexane (0.1% TFA)/ethanol; Gradient: 15% EtOH; Detector: 254 nm], Retention time = 4.48 min. ¹HNMR (300 MHz, CD₃OD, ppm): δ 7.57 (d, J = 15.9 Hz, 1 H), 7.55-7.51 (m, 1 H), 7.50-7.49 (m, 1 H), 7.35-7.32 (m, 1 H), 7.30-7.19 (m, 3 H), 6.56 (d, J = 16.2 Hz, 1 H), 5.29 (s, 1 H), 3.62-3.56 (m, 1 H), 3.15-3.14 (m, 1 H), 3.11-2.95 (m, 1 H), 2.69-2.60 (m, 2 H), 1.44 (t, J = 18.6 Hz, 3 H), 1.18 (d, J = 6.6 Hz, 3 H). |

TABLE 4-continued

Exemplary Derivatives of Compound 24

| Example No. | Compound | [M + H]+ | HNMR and Chiral HPLC |
|---|---|---|---|
| 44B | 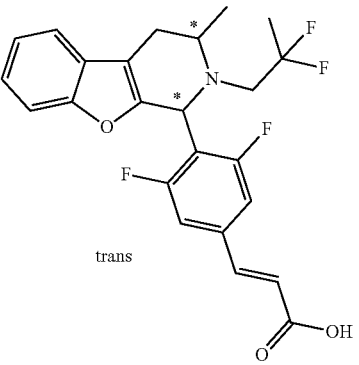 [SMILES: CC1Cc2c(oc3ccccc23)C(c2c(F)cc(/C=C/C(=O)O)cc2F)N1CC(C)(F)F] trans | 448.5 | Chiral HPLC [Column: AD, 100 mm, 4.6 mm, 0.6 mL/min, Mobile Phase: hexane (0.1% TFA)/ethanol; Gradient: 15% EtOH; Detector: 254 nm], Retention time = 3.69 min. $^1$HNMR (300 MHz, CD$_3$OD, ppm): δ 7.57 (d, J = 15.9 Hz, 1 H), 7.55-7.51 (m, 1 H), 7.50-7.49 (m, 1 H), 7.35-7.32 (m, 1 H), 7.30-7.19 (m, 3 H), 6.56 (d, J = 16.2 Hz, 1 H), 5.29 (s, 1 H), 3.62-3.56 (m, 1 H), 3.15-3.14 (m, 1 H), 3.11-2.95 (m, 1 H), 2.69-2.60 (m, 2 H), 1.44 (t, J = 18.6 Hz, 3 H), 1.18 (d, J = 6.6 Hz, 3 H). |
| 45 | 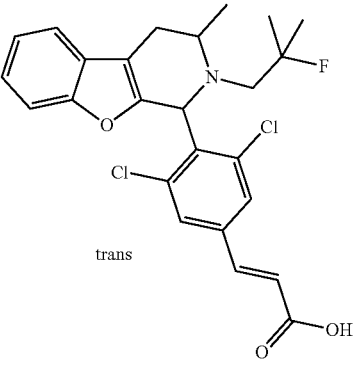 [SMILES: CC1Cc2c(oc3ccccc23)C(c2c(Cl)cc(/C=C/C(=O)O)cc2Cl)N1CC(C)(C)F] trans | 476.4 | $^1$HNMR (300 MHz, CD$_3$OD, ppm) δ 7.75-7.65 (m, 1 H), 7.49-7.41 (m, 2 H), 7.39-7.31 (m, 1 H), 7.29-7.22 (m, 1 H), 7.20-7.15 (m, 2 H), 6.56 (d, J = 15.6 Hz, 1 H), 5.69 (s, 1H), 3.90-3.86 (m, 1 H), 3.16-2.99 (m, 2 H), 2.62 (d, J = 15.3 Hz, 1 H), 2.36-2.21 (m, 1H), 1.24-1.09 (m, 9 H). |
| 46A | 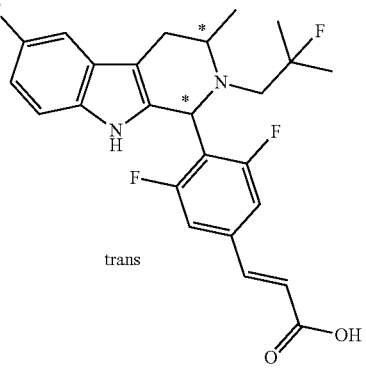 trans | 461.3 | Chiral HPLC [Column: AD, 100 mm, 4.6 mm, 0.6 mL/min, Mobile Phase: hexane (0.1% TFA)/ethanol; Gradient: 10% EtOH; Detector: 254 nm], Retention time = 9.39 min. $^1$HNMR (300 MHz, CD$_3$OD, ppm) δ 7.58 (d, J = 15.9 Hz, 1 H), 7.20 (d, J = 9.9 Hz, 2 H), 7.12-7.01 (m, 2 H), 6.79 (dt, J = 2.7, 9.3 Hz, 1 H), 6.53 (d, J = 16.2 Hz, 1 H), 5.29 (s, 1 H), 3.70-3.65 (m, 1 H), 3.05-2.88 (m, 2 H), 2.65-2.55 (m, 1 H), 2.47-2.34 (m, 1 H), 1.29-1.09 (m, 9 H). |
| 46B | 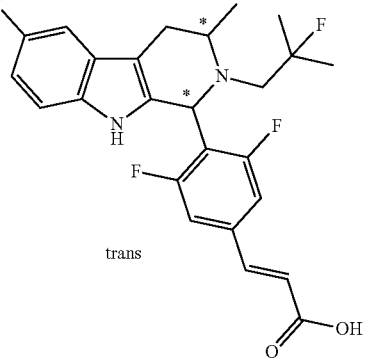 trans | 461.3 | Chiral HPLC [Column: IA, 100 mm, 4.6 mm, 0.6 mL/min, Mobile Phase: hexane (0.1% TFA)/ethanol; Gradient: 10% EtOH; Detector: 254 nm], Retention time = 8.20 min. $^1$HNMR (300 MHz, CD$_3$OD, ppm) 7.57 (d, J = 23.7 Hz, 1 H), 7.20-7.05 (m, 4 H), 6.76 (dt, J = 2.1, 9.3, 1 H), 6.53 (d, J = 16.2 Hz, 1 H), 5.28 (s, 1 H), 3.69-3.67 (m, 1 H), 3.05-2.88 (m, 2 H), 2.60-2.33 (m, 2 H), 1.40-1.10 (m, 9 H). |

TABLE 4-continued

Exemplary Derivatives of Compound 24

| Example No. | Compound | [M + H]+ | HNMR and Chiral HPLC |
|---|---|---|---|
| 47A | | 444.4 | Chiral HPLC [Column: IA, 100 mm, 4.6 mm, 0.6 mL/min, Mobile Phase: hexane (0.1% TFA)/ethanol; Gradient: 5% EtOH; Detector: 254 nm], Retention time = 5.58 min. ¹H NMR (300 MHz, DMSO-d₆, ppm): δ7.59 (d, J = 4.2 Hz, 1 H), 7.57-7.44 (m, 4 H), 7.28-7.23 (m, 2 H), 6.68 (d, J = 15.9 Hz, 1 H), 5.21 (s, 1 H), 3.51-343 (m, 1 H), 2.98-2.85 (m, 2 H), 2.62-2.57 (m, 1 H), 2.51-2.44 (m, 1 H), 1.29-1.09 (m, 9 H). |
| 47B | | 444.4 | Chiral HPLC [Column: IA, 100 mm, 4.6 mm, 0.6 mL/min, Mobile Phase: hexane (0.1% TFA)/ethanol; Gradient: 5% EtOH; Detector: 254 nm], Retention time = 6.17 min. ¹H NMR (300 MHz, DMSO-d₆, ppm): δ7.58-7.43 (m, 5 H), 7.28-7.21 (m, 2 H), 6.68 (d, J = 15.9 Hz, 1 H), 5.21 (s, 1 H), 3.53-3.51 (m, 1 H), 2.98-2.85 (m, 2 H), 2.62-2.57 (m, 1 H), 2.52-2.36 (m, 1 H), 1.25-1.09 (m, 9 H). |
| 48A | | 460.3 | Chiral HPLC [Column: AD, 100 mm, 4.6 mm, 0.6 mL/min, Mobile Phase: hexane (0.1% TFA)/ethanol; Gradient: 30% EtOH; Detector: 254 nm], Retention time = 3.37 min. ¹HNMR: (300 MHz, CD₃OD, ppm): δ 7.72 (d, J = 7.8 Hz, 1 H), 7.66 (d, J = 7.8 Hz, 1 H), 7.39-7.24 (m, 3 H), 7.13 (d, J = 10.2 Hz, 2 H), 6.53 (d, J = 15.9 Hz, 1 H), 5.34 (s, 1 H), 3.80-3.78 (m, 1 H), 3.20-2.91 (m, 2 H), 2.78-2.72 (m, 1 H), 2.45-2.31 (m, 1 H), 1.19-1.11 (m, 9 H). |
| 48B | | 460.3 | Chiral HPLC [Column: AD, 100 mm, 4.6 mm, 0.6 mL/min, Mobile Phase: hexane (0.1% TFA)/ethanol; Gradient: 30% EtOH; Detector: 254 nm], Retention time = 2.66 min. ¹HNMR (300 MHz, CD₃OD, ppm): δ 7.72 (d, J = 7.8 Hz, 1 H), 7.66 (d, J = 7.8 Hz, 1 H), 7.38-7.25 (m, 3 H), 7.12 (d, J = 10.2 Hz, 2 H), 6.53 (d, J = 15.9 Hz, 1 H), 5.34 (s, 1 H), 3.81-3.77 (m, 1 H), 3.20-2.91 (m, 2 H), 2.78-2.72 (m, 1 H), 2.45-2.31 (m, 1 H), 1.19-1.11 (m, 9 H). |

TABLE 4-continued

Exemplary Derivatives of Compound 24

| Example No. | Compound | [M + H]+ | HNMR and Chiral HPLC |
|---|---|---|---|
| 49 | (structure) | 463.1 | $^1$H NMR (300 MHz, DMSO-$d_6$, ppm): δ 12.59 (s, 1H), 10.52 (s, 1H), 7.73 (s, 1H), 7.67-7.51 (m, 2H), 7.42 (dd, J = 7.1, 1.6 Hz, 1H), 7.23-7.13 (m, 1H), 7.03-6.93 (m, 2H), 6.71 (d, J = 16.0 Hz, 1H), 5.42 (s, 1H), 3.67-3.48 (m, 1H), 3.23-2.95 (m, 2H), 2.72-2.53 (m, 2H), 1.39 (t, J = 19.1 Hz, 3H), 1.09 (d, J = 6.3 Hz, 3H). |

Biological Assays of the Exemplary Compounds Described Herein

Example 9. MCF-7 ER Degradation Assay

The level of ER degradation by SERD described in this patent was analyzed by cell based high content imaging method. Briefly, human ER+ breast cancer MCF-7 cells were seeded into Grenier 96-well plates at a density of 5000 cells per well and grown in RPMI 1640 supplemented with 10% FBS (Gibco) at 37° C. with 5% $CO_2$ for 48 hours. Then, 1 μL of compound solution (in DMSO) was added to the cells to make a final concentration of 1 nM per each well of treated cells. DMSO at the same final concentration (%) per each well was used to serve as negative control on each plate. After 4 hours or 24 hours of treatment at 37° C. with 5% $CO_2$, the cells were fixed and permeabilized. Media from each well was aspirated and cells were gently washed with 1×PBS for 5 minutes and the wash procedure was repeated 3 times. Cells was then fixed with 4% formaldehyde freshly made in 1×PBS at room temperature for 20 minutes, followed by gentle washing with 1×PBS, 3 times for 5 minute each. The assay plate was incubated with 200 μl of 1×PBS containing 0.2% Triton-X100 for 5 minutes at room temperature, cells were then washed again with 1×PBS 3 times for 5 minutes each. After this, cells were incubated with the blocking buffer (1×PBS with 5% BSA) at room temperature for 1 hour. For immunostaining, blocking buffer was removed and primary anti-ER antibody (ER1D5, Santa Cruz) diluted in blocking buffer (1:400) was added to each well and cells were incubated overnight at 4° C. The next day, cells were washed with 1×PBS for 3 times with 5 minute each. Fluorochrome-labeled secondary antibody (goat anti-mouse IgG antibody, Alexa Fluor 488 conjugate, ThermoFisher, Cat #: A-11001) diluted in 1% BSA in 1×PBS (1:1000) was added to each well and incubated with the cells for 45 min at 37° C. in a moist environment in the dark. Cells were washed with 1×PBS for 3 times with 5 minute each time. Cells were incubated with DAPI (Beyotime; 1 g/ml) for 10 minutes and washed with 1×PBS for 3 times with 5 minute each time. For high content imaging analysis, plates were read on Cellomics ArrayScan™ XTI High Content Platform (ASN00002P) with excitation at 485 nm and imaging data was collected with minimum of 1000 cells per well. SERD induced ER degradation in the MCF-7 cells were measured using DMSO negative control as the baseline.

TABLE 6

ER Degradation in MCF-7 cells

| Compound | MCF7 ER Degradation at 4 hr (%) | MCF7 ER Degradation at 24 hr (%) |
|---|---|---|
| Fulvestrant | 29 | 15 |
| AZD9496 | 17 | 23 |
| 20 | 25 | 21 |
| 34A | 21 | 20 |
| 46A | 25 | 20 |

Example 10. MCF-7 Cell Growth Study

Compound activity was analyzed using celltiter-glo luminescent viability assay (Promega #G7572) in breast cancer cell line MCF-7. Cells grown in log phase are trypsinized and seeded into a 96-well cell culture plate at a density of $2\times10^3$ per well and incubated overnight at 37° C. with 5% $CO_2$ in humidified culture chamber. The next day, compounds were prepared in 100% DMSO and were serially diluted and added into cells in the following final concentrations: 316, 100, 31.6, 10, 3.16, 1, 0.32, 0.1, 0.03, 0.01, 0.003 and 0.001 nM. As a control, same volume and concentration of DMSO vehicle control solution was added to the control wells in each plate. The cells were incubated with compounds at 37° C. culture chamber for 6 days. Promega's celltiter-glo kit was used to analyze the cell viability, according to manufacture's instruction. Briefly, fifty microliter of celltiter-glo reagent was added to each well, plate (covered with aluminum foil) was gently vibrated for 10 min to induce cell lysis at room temperature. Luminescence was measured using a SPECTRAmax i3 reader. Cell growth inhibition $IC_{50}$ is calculated using GraphPad Prism V5.0 software. % inhibition=(1−(max signal/min signal))*100%

TABLE 5

Inhibitory Activity of Representative Compounds

| Compound | IC$_{50}$ (nM) | Compound | IC$_{50}$ (nM) |
|---|---|---|---|
| Fulvestrant | 0.4 | AZD9496 | 0.4 |
| GDC-0810 | 8.5 | 1 | 0.3 |
| 2 | 0.9 | 3 | 0.6 |
| 4 | 0.9 | 5 | 0.3 |
| 6 | 0.4 | 7 | 0.8 |
| 8 | 1 | 9 | 3.1 |
| 10 | 3.2 | 11 | 0.4 |
| 12 | 0.26 | 13A | 0.5 |
| 14B | 2.6 | 15A | 1.8 |
| 16A | 0.6 | 17A | 0.8 |
| 18 | 8.9 | 19A | 3.1 |
| 20 | 0.3 | 21 | 0.5 |
| 22A | 2.6 | 23 | 4.2 |
| 24 | 1.9 | 25 | 0.8 |
| 26A | 0.6 | 27B | 0.7 |
| 28 | 1.3 | 29 | 0.9 |
| 30 | 1 | 31A | 0.4 |
| 32A | 1.9 | 33A | 1.2 |
| 34A | 0.4 | 35A | 2.5 |
| 36 | 16 | 37A | 2.9 |
| 38A | 0.6 | 39A | 2.6 |
| 40A | 0.9 | 40B | >100 |
| 41 | 0.6 | 42A | 1.9 |
| 42B | >100 | 43B | 0.8 |
| 44A | 7.9 | 45 | 8.9 |
| 46A | 0.4 | 46B | >100 |
| 47A | >100 | 47B | 0.6 |
| 48A | 4.7 | 49 | 0.5 |

Example 11. Human Hepatocyte Clearance Study

The in vitro hepatocyte clearance of compound described here was studied using pooled human hepatocytes purchased from BioreclamationIVT (Westbury, N.Y., Cat #X008001, Lot #TQJ). Assay was conducted according to manufacture's instruction. Briefly, 10 mM tock solutions of test compound and positive control (Verapamil) were prepared in 100% DMSO. Thawing media (50 mL) used in the study consists of: 31 mL Williams E medium (GIBCO Cat #12551-032); 15 mL isotonic percoll (GE Healthcare Cat #17-0891-09); 500 uL 100×GlutaMax (GIBCO Cat #35050); 750 uL HEPES (GIBCO Cat #15630-080); 2.5 mL FBS (Corning Cat #35-076-CVR); 50 uL human insulin (GIBCO Cat #12585-014) and 5 uL dexamethasone (NICPBP). Incubation media is made of Williams E medium supplemented with 1×GlutaMax. Thawing medium and supplement incubation medium (serum-free) were placed in a 37° C. water bath for at least 15 minutes prior to use. Compound stock solutions were diluted to 100 µM by combining 198 µL of 50% acetonitrile/50% water and 2 µL of 10 mM stock solution. Verapamil was use as positive control in the assay. Vials of cryopreserved hepatocytes were removed from storage and thawed in a 37° C. water bath with gentle shaking. Contents of the vial were poured into the 50 mL thawing medium conical tube. Vials were centrifuged at 100 g for 10 minutes at room temperature. Thawing medium was aspirated and hepatocytes were re-suspended with serum-free incubation medium to yield ~1.5×10$^6$ cells/mL. Hepatocyte viability and density were counted using a Trypan Blue exclusion, and then cells were diluted with serum-free incubation medium to a working cell density of 0.5×10$^6$ viable cells/mL. Then, a portion of the hepatocytes at 0.5×10$^6$ viable cells/mL was boiled for 5 min prior to adding to the plate as negative control to eliminate the enzymatic activity so that little or no substrate turnover should be observed. The boiled hepatocytes were used to prepare negative samples. Aliquots of 198 µL hepatocytes were dispensed into each well of a 96-well non-coated plate. The plate was placed in the incubator on an orbital shaker at 500 rpm for approximately 10 minutes. Aliquots of 2 µL of the 100 µM test compound or positive control were added into respective wells of the non-coated 96-well plate to start the reaction. This assay was performed in duplicate. The plate was incubated in the incubator on an orbital shaker at 500 rpm for the designed time points. Twenty-five microliter of contents were transferred and mixed with 6 volumes (150 µL) of cold acetonitrile with IS (200 nM imipramine, 200 nM labetalol and 200 nM diclofenac) to terminate the reaction at time points of 0, 15, 30, 60, 90 and 120 minutes. Samples were centrifuged at 3,220 g for 25 minutes and aliquots of 150 µL of the supernatants was used for LC-MS/MS analysis. For data analysis, all calculations were carried out using Microsoft Excel. Peak areas were determined from extracted ion chromatograms. The in vitro half-life ($t_{1/2}$) of parent compound was determined by regression analysis of the percent parent disappearance vs. time curve. The in vitro half-life (in vitro $t_{1/2}$) was determined from the slope value: in vitro $t_{1/2}$=0.693/k. Conversion of the in vitro $t_{1/2}$ (in min) into the scale-up unbound intrinsic clearance (Scaled-up unbound CL$_{int}$, in mL/min/kg) was done using the following equation (mean of duplicate determinations): Scaled-up unbound CL$_{int}$=kV/N×scaling factor, where V=incubation volume (0.5 mL); N=number of hepatocytes per well (0.25×10$^6$ cells). Scaling factors for in vivo intrinsic clearance prediction using human hepatocytes are listed as: liver weight (g liver/kg body weight): 25.7; hepatocyte concentration (10$^6$ cells/g liver): 99; scaling factor: 2544.3.

TABLE 7

Human Hepatocyte Clearance of Selected SERD

| Compound | Human Hepatocyte Remaining Percentage @ 120 min (%) | Human In vitro T$_{1/2}$ (min) | Human In vitro Cl$_{int}$ (µL/min/10$^6$ cells) | Human Scale-up Cl$_{int}$ (mL/min/kg) |
|---|---|---|---|---|
| Fulvestrant | 12 | 42 | 33 | 86 |
| GDC-0810 | 24 | 56 | 24.6 | 63 |
| AZD9496 | 58 | 153 | 9.0 | 23 |
| 1 | 88 | 853 | 1.6 | 4.1 |
| 11 | 83 | 664 | 2.0 | 5.3 |
| 20 | 70 | 246 | 5.6 | 14 |
| 21 | 84 | 586 | 2.4 | 6 |
| 29 | 83 | 571 | 2.4 | 6.2 |

Example 12. Mouse PK Studies

Mouse PK study (iv 3 mpk, and po 30 mpk) was conducted using male CD1 mice (25-33 g) obtained from SLAC Laboratory Animal Co., LTD of Shanghai). Compound is prepared with the following formulation: 5% DMSO, 5% Solutol HS 15 and 9% HPBCD in water. For intravenous (iv) dose at 3 mpk and oral (po) dose at 30 mpk, the compound is formulated at the concentration 0.2 mg/mL and 1 mg/mL, respectively. Compound formulation is freshly made prior to dosing in the morning. Oral dosing is via the use of oral gavage at 10 mL/kg, while iv dosing is via tail vein at 5 mL/kg. Three mice are used for each dosing route per compound per dose. Serial blood sample (30 uL whole blood at each time point) is collected into the K$_2$EDTA tubes via facial vein at the following time points: 5 min (for iv route only), 30 min, 1, 2, 4, 6, 8, 12 and 24 hours. For each blood sample collected, immediately transfer 20 uL blood sample and mix well with 60 uL water in a 96-well plate (whole blood:water=1:3 v/v). Diluted blood samples are stored at −80 C freezer until analysis. For analysis, an aliquot of 20 μL sample was added with 200 μL IS (Glipizide, 100 ng/mL) in ACN. The mixture was vortexed for 2 min and centrifuged at 5800 rpm for 10 min. An aliquot of 2 μL supernatant was injected for LC-MS/MS analysis. Compound at 2.0-3000 ng/mL in CD1 mouse diluted blood is used for calibration curve. Pharmacokinetic data are obtained and described in the table below:

TABLE 8

PK Data of Selected SERD Compounds

| Compound | Mouse IV 3 mpk CL (L/hr/kg) | Mouse PO 30 mpk T½ (hr) | Mouse PO 30 mpk AUC last (uM · hr) |
| --- | --- | --- | --- |
| GDC-0810 | 0.92 | 2.9 | 80 |
| AZD9496 | 1.14 | 3.5 | 85 |
| 21 | 0.11 | 9.2 | 412 |
| 25 | 0.08 | 62 | 658 |

Example 13. Human Breast Cancer xMCF-7 Xenograft Efficacy Study in Mouse

To investigate the in vivo efficacy of SERD compounds described in this application, female nude mice were inoculated with human ER+ breast cancer cells xMCF-7. xMCF-7 cells are derived from MCF-7 (ATCC) tumor grown in the nude mice. Briefly, female balb/c mice (age 6-7 wk) were first inoculated subcutaneously on the back with estrogen pellet (0.5 mg, 60-day release from Innovative Research of America, Cat #SE-121). Two days later, each mouse was inoculated with 5 million xMCF-7 cells, prepared as 0.2 ml cell suspension in 1:1 mix of Eagle's MEM to cell culture media and Matrigel (Corning Cat #354234) for each injection. After tumor size reached ~235 mm$^3$, mice with xMCF-7 xenograft tumor are randomized to 10 mice per group and started receiving drug treatment. Each compound was prepared in dosing vehicle (5% DMSO, 5% Solutol HS15 and 10% HPBCD in water) and given orally at 5 mg/kg or 30 mg/kg, once a day for 28 days, except fulvestrant was prepared in peanut oil and given at 250 mg/kg subcutaneously, once a day for 28 days. In this study, drug treatment resulted in almost complete tumor growth inhibition, with compound 25 shown to be more efficacious in vivo than fulvestrant, GDC-0810 and AZD9496 (FIG. 1).

Figure 2:
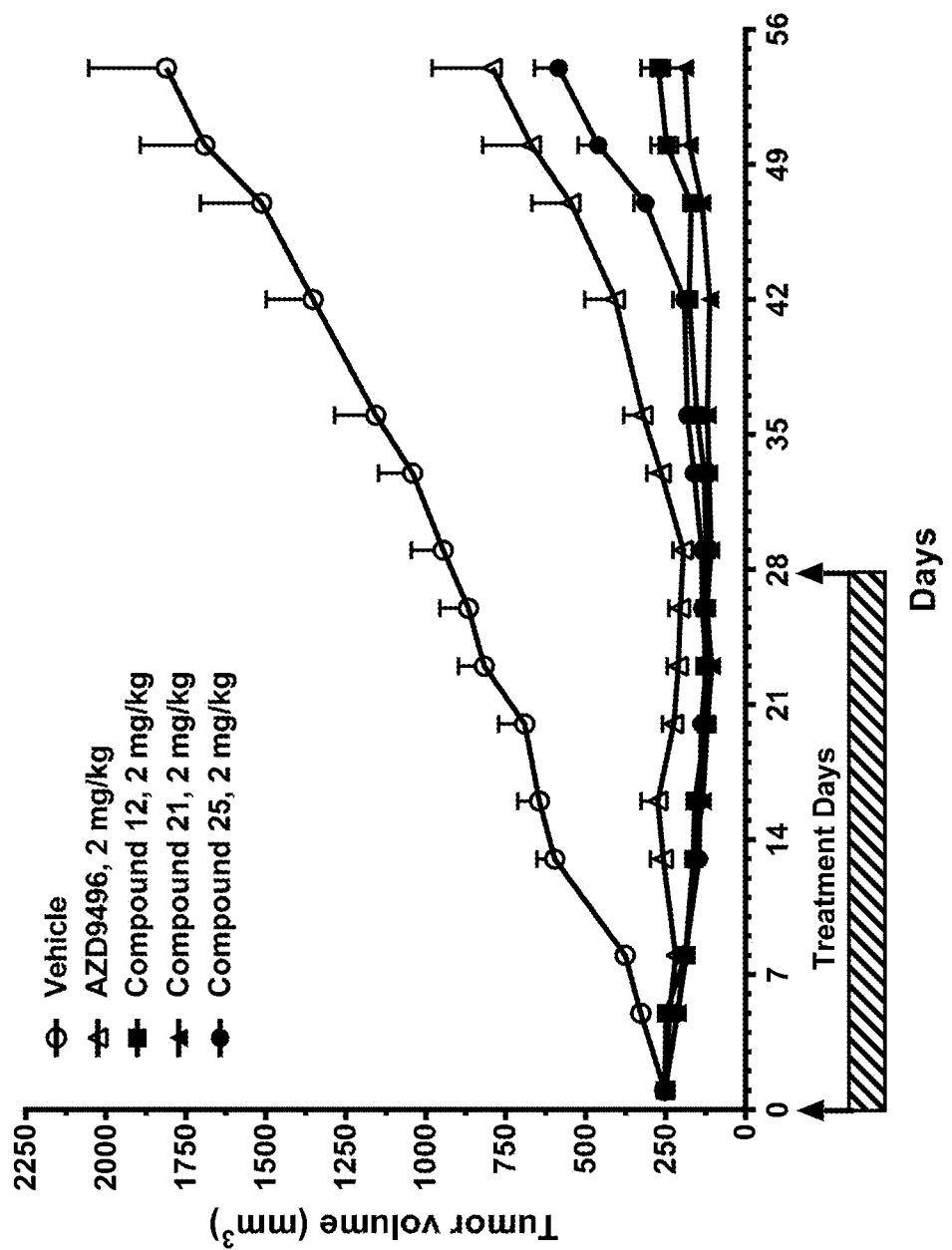
FIG. 2 is a chart showing the tumor volume change in a human breast cancer xMCF-7 xenograph efficacy study in a mouse model, under treatment by exemplary compounds 12, 21 and 25, compared with AZD9496.

In another xMCF-7 study, treatment initiated when tumor reached ~250 mm$^3$. Each drug was given at 2 mg/kg orally, once daily for 28 days. Significant tumor growth inhibition and tumor regression was observed and compounds 12, 21 and 25 were shown to be more efficacious than AZD9496 (FIG. 2).

Figure 3:
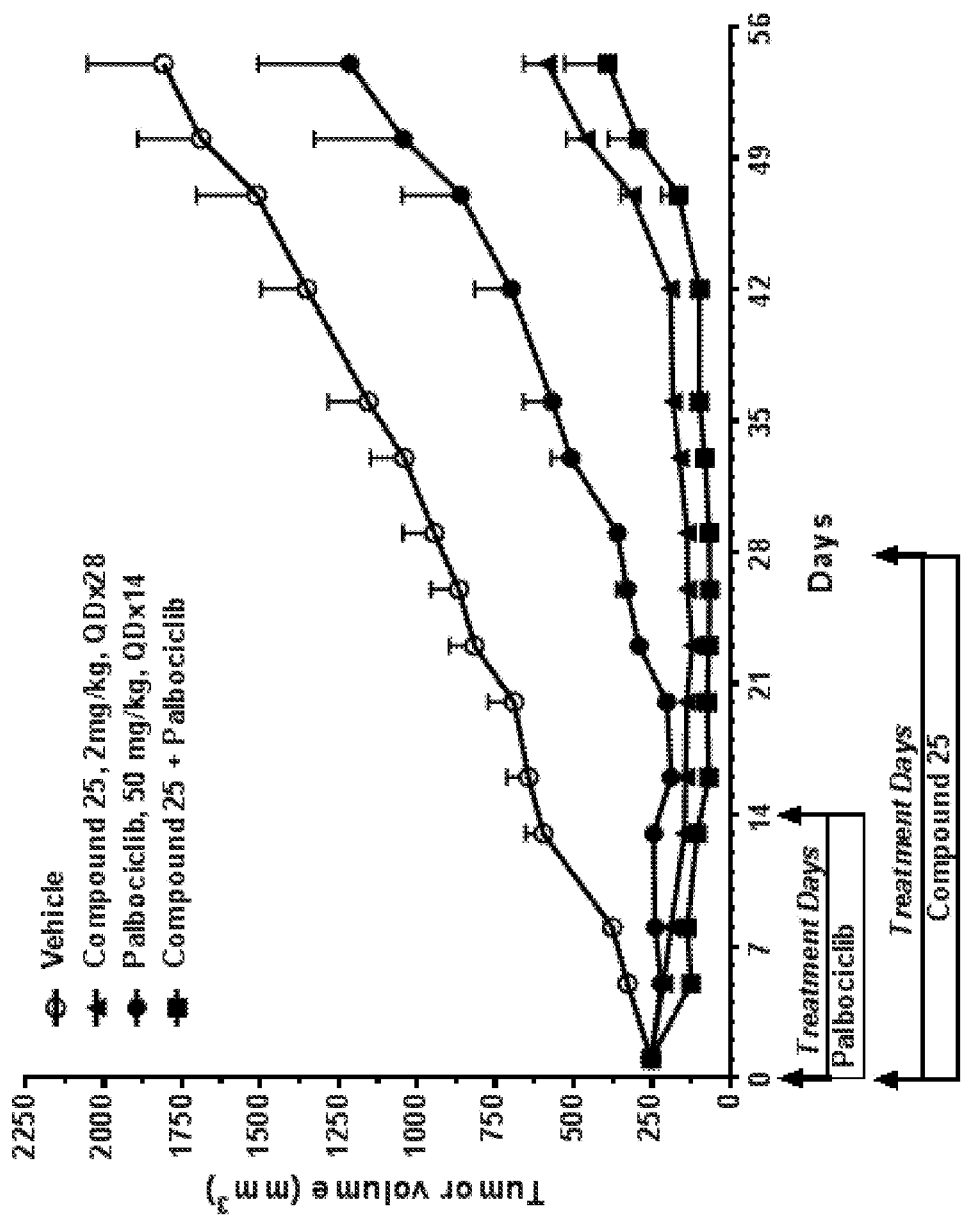
FIG. 3 is a chart showing the effect of treatment with a combination of exemplary compound 25 with CDK4/6 inhibitor palbocilib in the tumor volume change in a human breast cancer xMCF-7 xenograft xenograph efficacy study in a mouse model.

Example 14: Combination of SERD Compound 25 with CDK4/6 Inhibitor Palbocilib in xMCF-7 Xenograft Model CDK4/6 inhibitor such as pabociclib was approved for ER positive, Her2 negative metastatic breast cancer, to investigate if combination of SERD and CDK4 inhibitor would further increase the efficacy in ER positive breast cancer, we tested SERD compound 25 in combination with CDK4/6 inhibitor palbociclib in xMCF-7 human breast cancer xenograft model. In this study, when xMCF-7 tumor reached ~250 mm$^3$, compound 25 was given orally, once daily for 28 days and palbociclib was given orally at 50 mg/kg, once daily for 14 day. As shown in FIG. 3, combination of palbociclib and compound 25 results in better tumor growth regression than either palbociclib or compound 25 used alone.

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

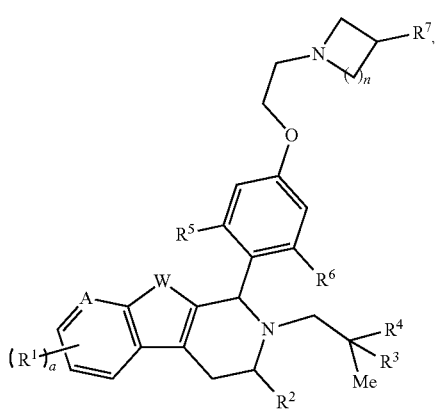

or a pharmaceutically acceptable salt thereof,
wherein:
  A is —CR$^A$= or —N=, as valency permits;
  W is —NH—, —O—, or —S—;
  a is 1, 2, or 3;
  n is 1, 2, 3, or 4;
  each instance of R$^1$ is independently hydrogen, halogen, substituted or unsubstituted alkyl, —OR$^A$, or —CN;
  R$^2$ is hydrogen, substituted or unsubstituted alkyl, substituted or unsubstituted carbocyclyl;
  R$^3$ is hydrogen, halogen, substituted or unsubstituted alkyl, substituted or unsubstituted carbocyclyl, substituted or unsubstituted heterocyclyl, substituted or unsubstituted aryl, or substituted or unsubstituted heteroaryl, —OR$^A$, or —N(R$^B$)$_2$;
  R$^4$ is hydrogen, halogen, substituted or unsubstituted alkyl, substituted or unsubstituted carbocyclyl, substituted or unsubstituted heterocyclyl, substituted or unsubstituted aryl, or substituted or unsubstituted heteroaryl, —OR$^A$ or —N(R$^B$)$_2$;
  R$^5$ is fluorine or chlorine;
  R$^6$ is chlorine;
  R$^7$ is hydrogen, halogen, substituted or unsubstituted alkyl, —OR$^A$ or —N(R$^B$)$_2$;
  R$^A$ is hydrogen or substituted or unsubstituted alkyl, or oxygen protecting group; and
  R$^B$ is hydrogen or substituted or unsubstituted alkyl, nitrogen protecting group, or optionally two R$^B$ are taken together with the intervening atoms to form substituted or unsubstituted heterocyclyl or substituted or unsubstituted heteroaryl.

2. A compound of the formula:

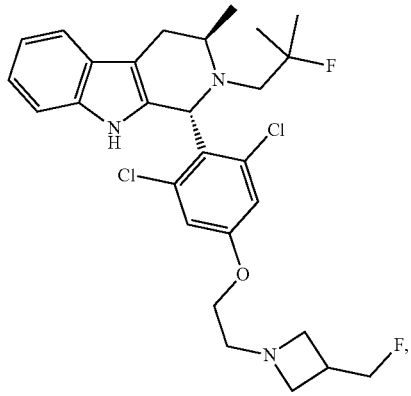

9

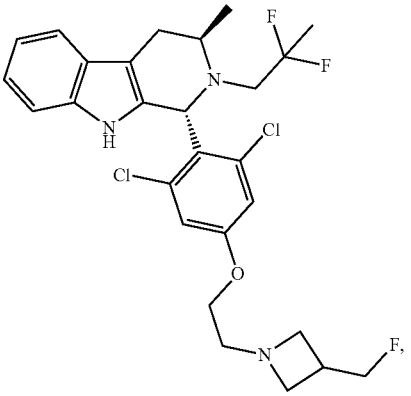

10

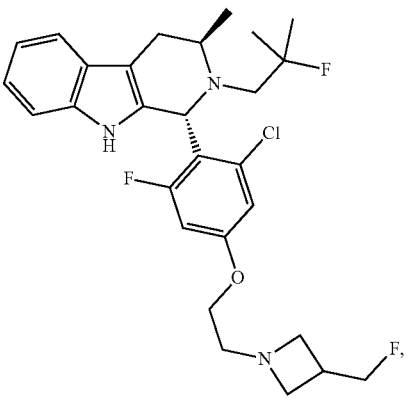

11

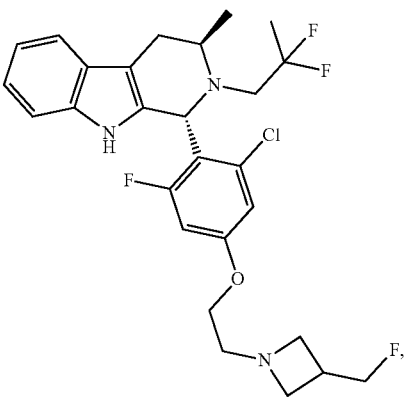

12

14 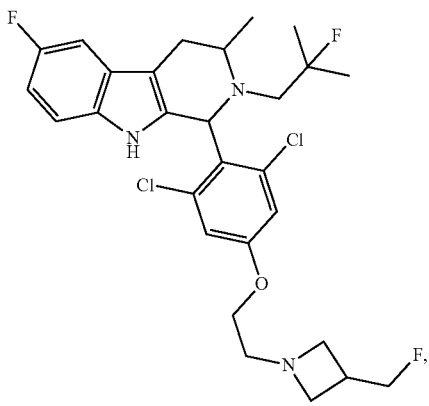

16 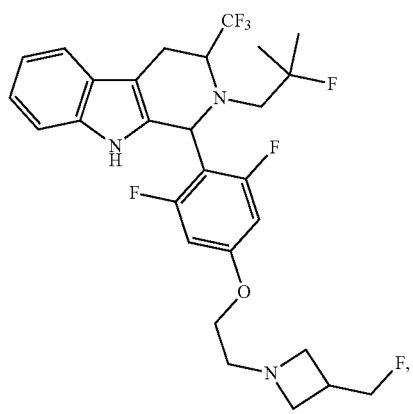

17 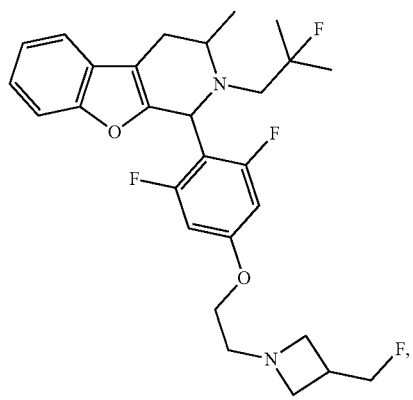

18 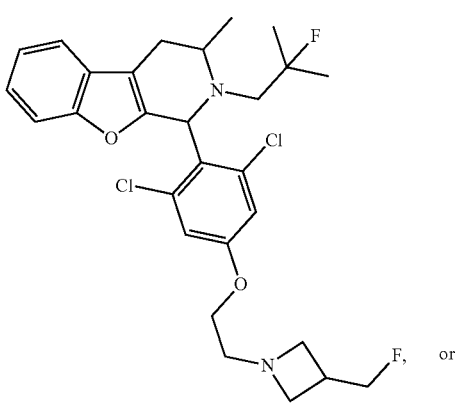

19 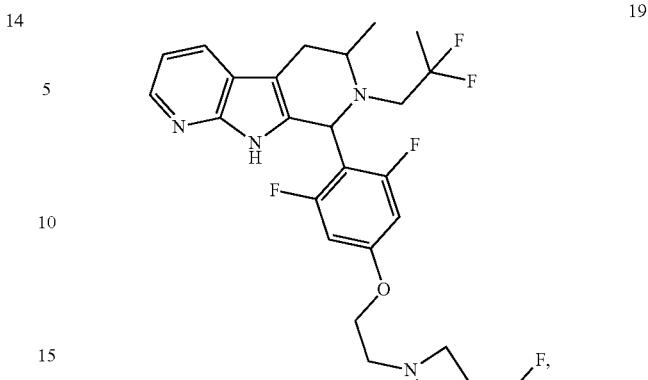

or or a pharmaceutically acceptable salt thereof.

3. A pharmaceutical composition comprising a compound of claim 1, or a pharmaceutically acceptable salt thereof, and a pharmaceutically acceptable excipient.

4. A method of treating breast cancer, the method comprising administering to a subject in need thereof an effective amount of a pharmaceutical composition of claim 3.

5. The method of claim 4, wherein the breast cancer is ER+ breast cancer.

6. The compound of claim 1, wherein the compound is of the formula (IA):

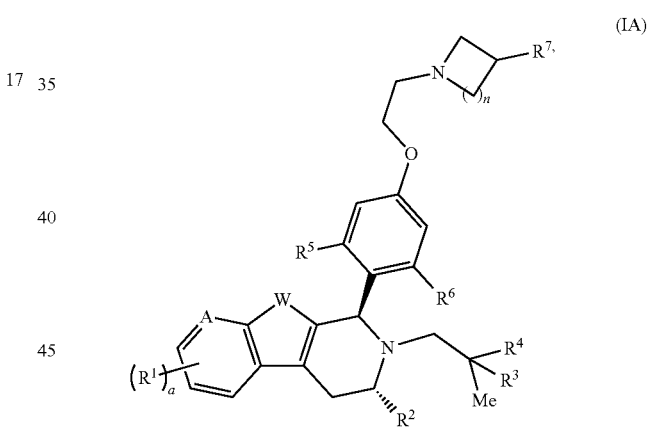

or a pharmaceutically acceptable salt thereof.

7. The compound of claim 1, or a pharmaceutically acceptable salt thereof, wherein A is —CH=.

8. The compound of claim 1, or a pharmaceutically acceptable salt thereof, wherein W is —NH—.

9. The compound of claim 1, or a pharmaceutically acceptable salt thereof, wherein a is 1.

10. The compound of claim 9, or a pharmaceutically acceptable salt thereof, wherein $R^1$ is —OMe, —$CF_3$, or —CN.

11. The compound of claim 1, or a pharmaceutically acceptable salt thereof, wherein n is 1.

12. The compound of claim 1, or a pharmaceutically acceptable salt thereof, wherein $R^2$ is methyl or —$CF_3$.

13. The compound of claim 1, or a pharmaceutically acceptable salt thereof, wherein $R^3$ is fluorine or methyl.

14. The compound of claim 13, or a pharmaceutically acceptable salt thereof, wherein $R^4$ is fluorine or methyl.

15. The compound of claim 1, or a pharmaceutically acceptable salt thereof, wherein $R^7$ is —$CH_2F$.

16. A pharmaceutical composition comprising a compound of claim 2, or a pharmaceutically acceptable salt thereof, and a pharmaceutically acceptable excipient.

17. A method of treating breast cancer, the method comprising administering to a subject in need thereof an effective amount of a pharmaceutical composition of claim 16.

18. The method of claim 17, wherein the breast cancer is ER+ breast cancer.

* * * * *